(12) United States Patent
Han et al.

(10) Patent No.: US 12,208,289 B2
(45) Date of Patent: Jan. 28, 2025

(54) ANTI-CD79b ANTIBODIES, DRUG CONJUGATES, AND APPLICATIONS THEREOF

(71) Applicant: NewBio Therapeutics, Inc., Shanghai (CN)

(72) Inventors: Nianhe Han, Shanghai (CN); Liwei Song, Shanghai (CN); Deqiang An, Shanghai (CN); Di Zeng, Shanghai (CN); Huali Li, Shanghai (CN); Chun Yang, Shanghai (CN)

(73) Assignee: NewBio Therapeutics, Inc., Shanghai (CN)

( * ) Notice: Subject to any disclaimer, the term of this patent is extended or adjusted under 35 U.S.C. 154(b) by 941 days.

(21) Appl. No.: 17/286,759

(22) PCT Filed: Oct. 31, 2019

(86) PCT No.: PCT/CN2019/114676
§ 371 (c)(1),
(2) Date: Apr. 19, 2021

(87) PCT Pub. No.: WO2020/088587
PCT Pub. Date: May 7, 2020

(65) Prior Publication Data
US 2021/0388082 A1 Dec. 16, 2021

(30) Foreign Application Priority Data
Nov. 1, 2018 (CN) .......................... 201811296100.8

(51) Int. Cl.
| | | |
|---|---|---|
| *A61K 47/68* | (2017.01) | |
| *A61K 39/00* | (2006.01) | |
| *A61P 35/00* | (2006.01) | |
| *A61P 35/02* | (2006.01) | |
| *C07K 16/28* | (2006.01) | |

(52) U.S. Cl.
CPC .... *A61K 47/6849* (2017.08); *A61K 47/68031* (2023.08); *A61K 47/68033* (2023.08); *A61P 35/00* (2018.01); *A61P 35/02* (2018.01); *C07K 16/2803* (2013.01); *A61K 2039/505* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 4,892,538 A | 1/1990 | Aebischer et al. |
| 5,283,187 A | 2/1994 | Aebischer et al. |
| 5,648,237 A | 7/1997 | Carter |
| 5,789,199 A | 8/1998 | Joly et al. |
| 5,840,523 A | 11/1998 | Simmons et al. |
| 9,845,355 B2 * | 12/2017 | Chen .................. C07K 16/3061 |
| 2014/0030280 A1 * | 1/2014 | Polakis .............. A61K 47/6849 435/375 |
| 2014/0030282 A1 * | 1/2014 | Polakis .............. A61K 47/6809 435/375 |
| 2016/0053007 A1 * | 2/2016 | Siegel ................ C07K 16/2875 536/23.53 |
| 2016/0159906 A1 * | 6/2016 | Sun ........................ A61P 37/02 424/139.1 |

FOREIGN PATENT DOCUMENTS

| | | |
|---|---|---|
| AU | 2012204069 A1 | 7/2012 |
| AU | 2016273960 A1 | 1/2017 |
| CN | 103933575 A | 7/2014 |
| CN | 107652219 A | 2/2018 |
| WO | 9607321 A1 | 3/1996 |
| WO | 9824893 A2 | 6/1998 |
| WO | 2009012256 A1 | 1/2009 |
| WO | 2009012268 A1 | 1/2009 |
| WO | 2014011519 A1 | 1/2014 |
| WO | 2016090210 A1 | 6/2016 |
| WO | 2016192527 A1 | 12/2016 |

OTHER PUBLICATIONS

Clackson et al., Making Antibody Fragments Using Phage Display Libraries, Nature, 1991, 352(6336):624-628.
Ducry et al., Antibody—Drug Conjugates: Linking Cytotoxic Payloads to Monoclonal Antibodies, Bioconjugate Chemistry, 2010, 21(1):5-13.
Kohler et al., Continuous Cultures of Fused Cells Secreting Antibody of Predefined Specificity, Nature, 1975, 256 (5517):495-497.
Svedhem et al., Synthesis of a Series of Oligo (ethylene glycol)-Terminated Alkanethiol Amides Designed to Address Structure and Stability of Biosensing Interfaces, Journal of Organic Chemistry, 2001, 66(13):4494-4503.
PCT International Search Report and Written Opinion, PCT/CN2019/114676, Jan. 10, 2020, 8 pages.
European Patent Office, Extended European Search Report, Application No. 19878515.6, Jun. 29, 2022, 6 pages.

(Continued)

*Primary Examiner* — Juliet C Switzer
*Assistant Examiner* — Katherine Ann Holtzman
(74) *Attorney, Agent, or Firm* — Quarles & Brady LLP

(57) ABSTRACT

Disclosed herein is an anti-CD79b antibody or antigen-binding fragment thereof, a drug conjugate thereof and use thereof. The anti-CD79b antibody or antigen-binding fragment thereof herein comprises: HCDR1 comprising the amino acid sequence of SEQ ID NO: 1; HCDR2 comprising the amino acid sequence of SEQ ID NO: 2; HCDR3 comprising the amino acid sequence of SEQ ID NO: 3; LCDR1 comprising the amino acid sequence of SEQ ID NO: 4; LCDR2 comprising the amino acid sequence of SEQ ID NO: 5; and LCDR3 comprising the amino acid sequence of SEQ ID NO: 6.

22 Claims, 4 Drawing Sheets
Specification includes a Sequence Listing.

(56) References Cited

OTHER PUBLICATIONS

Intellectual Property India, First Examination Report, Application No. 202117017699, Nov. 23, 2022, 6 pages.
Japanese Patent Office, Notice of Reasons for Refusal, Application No. 2021-523617, Oct. 4, 2023, 10 pages.

* cited by examiner

```
                        SEQUENCE LISTING

<160> NUMBER OF SEQ ID NOS: 39

<210> SEQ ID NO 1
<211> LENGTH: 10
<212> TYPE: PRT
<213> ORGANISM: Artificial Sequence
<220> FEATURE:
<223> OTHER INFORMATION: Synthetic - HCDR1

<400> SEQUENCE: 1

Gly Asn Thr Phe Thr Ser Tyr Gly Ile Asn
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Synthetic - HCDR2

<400> SEQUENCE: 2

Gly Glu Ile Phe Pro Arg Ser Gly Asn Ile Tyr Tyr Asn Glu Lys Phe
1               5                   10                  15

Lys Gly
```

```
<210> SEQ ID NO 3
<211> LENGTH: 10
<212> TYPE: PRT
<213> ORGANISM: Artificial Sequence
<220> FEATURE:
<223> OTHER INFORMATION: Synthetic - HCDR3

<400> SEQUENCE: 3

Ala Lys Gly Gly Thr Gly Asp Phe Asp Tyr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic - LCDR1

<400> SEQUENCE: 4

Arg Ser Ser Gln Asn Ile Val His Ser Asp Gly Asn Thr Tyr Leu Glu
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic - LCDR2

<400> SEQUENCE: 5

Lys Val Ser Phe Arg Leu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic - LCDR3

<400> SEQUENCE: 6

Phe Gln Gly Ser His Val Pro Trp Thr
1               5

<210> SEQ ID NO 7
<211> LENGTH: 117
<212> TYPE: PRT
<213> ORGANISM: Artificial Sequence
<220> FEATURE:
<223> OTHER INFORMATION: Synthetic - Amino acid sequence of mVH

<400> SEQUENCE: 7

Gln Val Gln Leu Gln Gln Ser Gly Ser Glu Leu Ala Arg Pro Gly Ala
1               5                   10                  15

Ser Val Lys Leu Ser Cys Lys Thr Ser Gly Asn Thr Phe Thr Ser Tyr
                20                  25                  30

Gly Ile Asn Trp Val Lys Gln Arg Thr Gly Gln Gly Leu Glu Trp Ile
            35                  40                  45

Gly Glu Ile Phe Pro Arg Ser Gly Asn Ile Tyr Tyr Asn Glu Lys Phe
        50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95
```

```
Ala Lys Gly Gly Thr Gly Asp Phe Asp Tyr Trp Gly Gln Gly Thr Thr
                100                 105                 110

Leu Thr Val Ser Ser
        115

<210> SEQ ID NO 8
<211> LENGTH: 112
<212> TYPE: PRT
<213> ORGANISM: Artificial Sequence
<220> FEATURE:
<223> OTHER INFORMATION: Synthetic - Amino acid sequence of mVL

<400> SEQUENCE: 8

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Phe Arg Leu Ser Gly Val Pro
    50                  55                  60

Asp Arg Phe Ser Gly Ser Gly Ser Gly Thr Asp Phe Thr Leu Lys Ile
65                  70                  75                  80

Arg Arg Val Glu Ala Glu Asp Leu Gly Thr Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 9
<211> LENGTH: 121
<212> TYPE: PRT
<213> ORGANISM: Artificial Sequence
<220> FEATURE:
<223> OTHER INFORMATION: Synthetic - AGC78785.1 immunoglobulin heavy
      chain variable region

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Ser Gly Val Gly Leu His Phe Gly Tyr Phe Asp Tyr Trp Gly
            100                 105                 110

Gln Gly Thr Leu Val Thr Val Ser Ser
        115                 120

<210> SEQ ID NO 10
<211> LENGTH: 277
<212> TYPE: PRT
<213> ORGANISM: Artificial Sequence
<220> FEATURE:
<223> OTHER INFORMATION: Synthetic - BAC01734.1 immunoglobulin kappa
``` light chain variable region

<400> SEQUENCE: 10

Met Lys Tyr Leu Leu Pro Thr Ala Ala Ala Gly Leu Leu Leu Leu Ala
1               5                   10                  15

Ala Gln Pro Ala Met Ala Asp Val Val Met Thr Gln Ser Pro Leu Ser
            20                  25                  30

Leu Pro Val Thr Leu Gly Gln Pro Ala Ser Ile Ser Cys Arg Ser Ser
        35                  40                  45

Gln Ser Leu Val His Ser Asp Gly Asn Thr Tyr Leu Asn Trp Phe Gln
    50                  55                  60

Gln Arg Pro Gly Gln Ser Pro Arg Arg Leu Ile Tyr Lys Val Ser Asn
65                  70                  75                  80

Arg Asp Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Gly Thr His Trp Pro Leu Thr Phe Gly Gly Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys Ser Ala Arg Gln Ser Thr Pro Phe Val Cys Glu Tyr Gln Gly Gln
                245                 250                 255

Ser Ser Asp Leu Pro Gln Pro Val Asn Ala Gly Gly Ser Gly
            260                 265                 270

Gly Gly Ser Gly Gly
        275

<210> SEQ ID NO 11
<211> LENGTH: 117
<212> TYPE: PRT
<213> ORGANISM: Artificial Sequence
<220> FEATURE:
<223> OTHER INFORMATION: Synthetic - HCDR-grafted VH

<400> SEQUENCE: 11

Gln Val Gln Leu Val Gln Ser Gly Ala Glu Val Lys Lys Pro Gly Ser
1               5                   10                  15

Ser Val Lys Val Ser Cys Lys Ala Ser Gly Asn Thr Phe Thr Ser Tyr
            20                  25                  30

Gly Ile Asn Trp Val Arg Gln Ala Pro Gly Gln Gly Leu Glu Trp Met
        35                  40                  45

Gly Glu Ile Phe Pro Arg Ser Gly Asn Ile Tyr Tyr Asn Glu Lys Phe
    50                  55                  60

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Thr Gly Gly Thr Gly Asp Phe Asp Tyr Trp Gly Gln Gly Thr Leu
            100                 105                 110

Val Thr Val Ser Ser
            115
```

<210> SEQ ID NO 12
<211> LENGTH: 112
<212> TYPE: PRT
<213> ORGANISM: Artificial Sequence
<220> FEATURE:
<223> OTHER INFORMATION: Synthetic - LCDR-grafted VL

<400> SEQUENCE: 12

```
Asp Val Val Met Thr Gln Ser Pro Leu Ser Leu Pro Val Thr Leu Gly
 1               5                   10                  15

Gln Pro Ala Ser Ile Ser Cys Arg Ser Gln Asn Ile Val His Ser
             20                  25                  30

Asp Gly Asn Thr Tyr Leu Glu Trp Phe Gln Gln Arg Pro Gly Gln Ser
             35                  40                  45

Pro Arg Arg Leu Ile Tyr Lys Val Ser Phe Arg Leu Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Trp Thr Phe Gly Gly Gly Thr Lys Val Glu Ile Lys
             100                 105                 110
```

<210> SEQ ID NO 13
<211> LENGTH: 117
<212> TYPE: PRT
<213> ORGANISM: Artificial Sequence
<220> FEATURE:
<223> OTHER INFORMATION: Synthetic - Heavy chain variable region of
      AS11161

<400> SEQUENCE: 13

```
Gln Val Gln Leu Val Gln Ser Gly Ala Glu Val Lys Lys Pro Gly Ser
 1               5                   10                  15

Ser Val Lys Val Ser Cys Lys Thr Ser Gly Asn Thr Phe Thr Ser Tyr
             20                  25                  30

Gly Ile Asn Trp Val Arg Gln Ala Pro Gly Gln Gly Leu Glu Trp Met
             35                  40                  45

Gly Glu Ile Phe Pro Arg Ser Gly Asn Ile Tyr Tyr Asn Glu Lys Phe
 50                  55                  60

Lys Gly Lys Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Lys Gly Gly Thr Gly Asp Phe Asp Tyr Trp Gly Gln Gly Thr Leu
            100                 105                 110

Val Thr Val Ser Ser
            115
```

<210> SEQ ID NO 14
<211> LENGTH: 117
<212> TYPE: PRT
<213> ORGANISM: Artificial Sequence
<220> FEATURE:
<223> OTHER INFORMATION: Synthetic - Heavy chain variable region of AS11164

<400> SEQUENCE: 14

```
Gln Val Gln Leu Val Gln Ser Gly Ala Glu Val Lys Lys Pro Gly Ser
1               5                   10                  15

Ser Val Lys Val Ser Cys Lys Thr Ser Gly Asn Thr Phe Thr Ser Tyr
            20                  25                  30

Gly Ile Asn Trp Val Arg Gln Ala Pro Gly Gln Gly Leu Glu Trp Met
        35                  40                  45

Gly Glu Ile Phe Pro Arg Ser Gly Asn Ile Tyr Tyr Asn Glu Lys Phe
    50                  55                  60

Lys Gly Lys Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Gly Thr Gly Asp Phe Asp Tyr Trp Gly Gln Gly Thr Leu
            100                 105                 110

Val Thr Val Ser Ser
        115
```

<210> SEQ ID NO 15
<211> LENGTH: 117
<212> TYPE: PRT
<213> ORGANISM: Artificial Sequence
<220> FEATURE:
<223> OTHER INFORMATION: Synthetic - Heavy chain variable region of AS11252

<400> SEQUENCE: 15

```
Gln Val Gln Leu Val Gln Ser Gly Ala Glu Val Lys Lys Pro Gly Ser
1               5                   10                  15

Ser Val Lys Leu Ser Cys Lys Thr Ser Gly Asn Thr Phe Thr Ser Tyr
            20                  25                  30

Gly Ile Asn Trp Val Lys Gln Ala Pro Gly Gln Gly Leu Glu Trp Ile
        35                  40                  45

Gly Glu Ile Phe Pro Arg Ser Gly Asn Ile Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Gly Thr Gly Asp Phe Asp Tyr Trp Gly Gln Gly Thr Leu
            100                 105                 110

Val Thr Val Ser Ser
        115
```

<210> SEQ ID NO 16
<211> LENGTH: 117
<212> TYPE: PRT
<213> ORGANISM: Artificial Sequence
<220> FEATURE:
<223> OTHER INFORMATION: Synthetic - Heavy chain variable region of AS11254

-continued

```
<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Thr Ser Gly Asn Thr Phe Thr Ser Tyr
            20                  25                  30

Gly Ile Asn Trp Val Lys Gln Ala Pro Gly Gln Gly Leu Glu Trp Met
        35                  40                  45

Gly Glu Ile Phe Pro Arg Ser Gly Asn Ile Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Gly Thr Gly Asp Phe Asp Tyr Trp Gly Gln Gly Thr Leu
            100                 105                 110

Val Thr Val Ser Ser
        115

<210> SEQ ID NO 17
<211> LENGTH: 117
<212> TYPE: PRT
<213> ORGANISM: Artificial Sequence
<220> FEATURE:
<223> OTHER INFORMATION: Synthetic - Heavy chain variable region of
      AS11259

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Thr Ser Gly Asn Thr Phe Thr Ser Tyr
            20                  25                  30

Gly Ile Asn Trp Val Lys Gln Ala Pro Gly Gln Gly Leu Glu Trp Ile
        35                  40                  45

Gly Glu Ile Phe Pro Arg Ser Gly Asn Ile Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Gly Thr Gly Asp Phe Asp Tyr Trp Gly Gln Gly Thr Leu
            100                 105                 110

Val Thr Val Ser Ser
        115

<210> SEQ ID NO 18
<211> LENGTH: 112
<212> TYPE: PRT
<213> ORGANISM: Artificial Sequence
<220> FEATURE:
<223> OTHER INFORMATION: Synthetic - Light chain variable region of
      AS11161

<400> SEQUENCE: 18

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asp Gly Asn Thr Tyr Leu Glu Trp Tyr Gln Gln Arg Pro Gly Gln Ser
```

```
            35                  40                  45
Pro Arg Leu Leu Ile Tyr Lys Val Ser Phe Arg Leu Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
                100                 105                 110
```

<210> SEQ ID NO 19
<211> LENGTH: 112
<212> TYPE: PRT
<213> ORGANISM: Artificial Sequence
<220> FEATURE:
<223> OTHER INFORMATION: Synthetic - Light chain variable region of
      AS11164

<400> SEQUENCE: 19

```
Asp Val Leu Met Thr Gln Ser Pro Leu Ser Leu Pro Val Thr Leu Gly
 1               5                  10                  15

Gln Pro Ala Ser Ile Ser Cys Arg Ser Ser Gln Asn Ile Val His Ser
                20                  25                  30

Asp Gly Asn Thr Tyr Leu Glu Trp Tyr Gln Gln Arg Pro Gly Gln Ser
            35                  40                  45

Pro Lys Leu Leu Ile Tyr Lys Val Ser Phe Arg Leu Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
                100                 105                 110
```

<210> SEQ ID NO 20
<211> LENGTH: 112
<212> TYPE: PRT
<213> ORGANISM: Artificial Sequence
<220> FEATURE:
<223> OTHER INFORMATION: Synthetic - Light chain variable region of
      AS11252

<400> SEQUENCE: 20

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Asn Ile Val His Ser
                20                  25                  30

Asp Gly Asn Thr Tyr Leu Glu Trp Tyr Gln Gln Arg Pro Gly Gln Ser
            35                  40                  45

Pro Arg Leu Leu Ile Tyr Lys Val Ser Phe Arg Leu Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
                100                 105                 110
```

```
<210> SEQ ID NO 21
<211> LENGTH: 112
<212> TYPE: PRT
<213> ORGANISM: Artificial Sequence
<220> FEATURE:
<223> OTHER INFORMATION: Synthetic - Light chain variable region of
      AS11254

<400> SEQUENCE: 21

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asp Gly Asn Thr Tyr Leu Glu Trp Tyr Gln Gln Arg Pro Gly Gln Ser
        35                  40                  45

Pro Arg Leu Leu Ile Tyr Lys Val Ser Phe Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

<210> SEQ ID NO 22
<211> LENGTH: 112
<212> TYPE: PRT
<213> ORGANISM: Artificial Sequence
<220> FEATURE:
<223> OTHER INFORMATION: Synthetic - Light chain variable region of
      AS11259

<400> SEQUENCE: 22

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asp Gly Asn Thr Tyr Leu Glu Trp Tyr Gln Gln Arg Pro Gly Gln Ser
        35                  40                  45

Pro Arg Leu Leu Ile Tyr Lys Val Ser Phe Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

<210> SEQ ID NO 23
<211> LENGTH: 330
<212> TYPE: PRT
<213> ORGANISM: Artificial Sequence
<220> FEATURE:
<223> OTHER INFORMATION: Synthetic - Heavy chain constant region

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 24
<211> LENGTH: 107
<212> TYPE: PRT
<213> ORGANISM: Artificial Sequence
<220> FEATURE:
<223> OTHER INFORMATION: Synthetic - Light chain constant region

<400> SEQUENCE: 24

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60
```

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 25
<211> LENGTH: 447
<212> TYPE: PRT
<213> ORGANISM: Artificial Sequence
<220> FEATURE:
<223> OTHER INFORMATION: Synthetic - Heavy chain of AS11161

<400> SEQUENCE: 25

```
Gln Val Gln Leu Val Gln Ser Gly Ala Glu Val Lys Lys Pro Gly Ser
1               5                   10                  15

Ser Val Lys Val Ser Cys Lys Thr Ser Gly Asn Thr Phe Thr Ser Tyr
                20                  25                  30

Gly Ile Asn Trp Val Arg Gln Ala Pro Gly Gln Gly Leu Glu Trp Met
            35                  40                  45

Gly Glu Ile Phe Pro Arg Ser Gly Asn Ile Tyr Tyr Asn Glu Lys Phe
 50                  55                  60

Lys Gly Lys Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Lys Gly Gly Thr Gly Asp Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320
```

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 26
<211> LENGTH: 219
<212> TYPE: PRT
<213> ORGANISM: Artificial Sequence
<220> FEATURE:
<223> OTHER INFORMATION: Synthetic - Light chain of AS11161

<400> SEQUENCE: 26

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asp Gly Asn Thr Tyr Leu Glu Trp Tyr Gln Gln Arg Pro Gly Gln Ser
        35                  40                  45

Pro Arg Leu Leu Ile Tyr Lys Val Ser Phe Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 27
<211> LENGTH: 447
```

<212> TYPE: PRT
<213> ORGANISM: Artificial Sequence
<220> FEATURE:
<223> OTHER INFORMATION: Synthetic - Heavy chain of AS11164

<400> SEQUENCE: 27

```
Gln Val Gln Leu Val Gln Ser Gly Ala Glu Val Lys Lys Pro Gly Ser
1               5                   10                  15

Ser Val Lys Val Ser Cys Lys Thr Ser Gly Asn Thr Phe Thr Ser Tyr
            20                  25                  30

Gly Ile Asn Trp Val Arg Gln Ala Pro Gly Gln Gly Leu Glu Trp Met
        35                  40                  45

Gly Glu Ile Phe Pro Arg Ser Gly Asn Ile Tyr Tyr Asn Glu Lys Phe
    50                  55                  60

Lys Gly Lys Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Gly Thr Gly Asp Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 28
<211> LENGTH: 219
<212> TYPE: PRT
<213> ORGANISM: Artificial Sequence
<220> FEATURE:
<223> OTHER INFORMATION: Synthetic - Light chain of AS11164

<400> SEQUENCE: 28

Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asp Gly Asn Thr Tyr Leu Glu Trp Tyr Gln Gln Arg Pro Gly Gln Ser
        35                  40                  45

Pro Lys Leu Leu Ile Tyr Lys Val Ser Phe Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 29
<211> LENGTH: 447
<212> TYPE: PRT
<213> ORGANISM: Artificial Sequence
<220> FEATURE:
<223> OTHER INFORMATION: Synthetic - Heavy chain of AS11252

<400> SEQUENCE: 29

Gln Val Gln Leu Val Gln Ser Gly Ala Glu Val Lys Lys Pro Gly Ser
1               5                   10                  15

Ser Val Lys Leu Ser Cys Lys Thr Ser Gly Asn Thr Phe Thr Ser Tyr
            20                  25                  30

```
Gly Ile Asn Trp Val Lys Gln Ala Pro Gly Gln Gly Leu Glu Trp Ile
            35                  40                  45
Gly Glu Ile Phe Pro Arg Ser Gly Asn Ile Tyr Tyr Asn Glu Lys Phe
    50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Lys Gly Gly Thr Gly Asp Phe Asp Tyr Trp Gly Gln Gly Thr Leu
            100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
            165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
            195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
            435                 440                 445
```

```
<210> SEQ ID NO 30
<211> LENGTH: 219
<212> TYPE: PRT
<213> ORGANISM: Artificial Sequence
<220> FEATURE:
<223> OTHER INFORMATION: Synthetic - Light chain of AS11252

<400> SEQUENCE: 30

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
            20                  25                  30

Asp Gly Asn Thr Tyr Leu Glu Trp Tyr Gln Gln Arg Pro Gly Gln Ser
        35                  40                  45

Pro Arg Leu Leu Ile Tyr Lys Val Ser Phe Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Tyr Tyr Cys Phe Gln Gly
                85                  90                  95

Ser His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 31
<211> LENGTH: 447
<212> TYPE: PRT
<213> ORGANISM: Artificial Sequence
<220> FEATURE:
<223> OTHER INFORMATION: Synthetic - Heavy chain of AS11254

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Thr Ser Gly Asn Thr Phe Thr Ser Tyr
            20                  25                  30

Gly Ile Asn Trp Val Lys Gln Ala Pro Gly Gln Gly Leu Glu Trp Met
        35                  40                  45

Gly Glu Ile Phe Pro Arg Ser Gly Asn Ile Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Lys Gly Gly Thr Gly Asp Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 32
<211> LENGTH: 219
<212> TYPE: PRT
<213> ORGANISM: Artificial Sequence
<220> FEATURE:
<223> OTHER INFORMATION: Synthetic - Light chain of AS11254

<400> SEQUENCE: 32

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
                20                  25                  30

Asp Gly Asn Thr Tyr Leu Glu Trp Tyr Gln Gln Arg Pro Gly Gln Ser
            35                  40                  45

Pro Arg Leu Leu Ile Tyr Lys Val Ser Phe Arg Leu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 33
<211> LENGTH: 447
<212> TYPE: PRT
<213> ORGANISM: Artificial Sequence
<220> FEATURE:
<223> OTHER INFORMATION: Synthetic - Heavy chain of AS11259

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Thr Ser Gly Asn Thr Phe Thr Ser Tyr
                20                  25                  30

Gly Ile Asn Trp Val Lys Gln Ala Pro Gly Gln Gly Leu Glu Trp Ile
            35                  40                  45

Gly Glu Ile Phe Pro Arg Ser Gly Asn Ile Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Gly Thr Gly Asp Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 34
<211> LENGTH: 219
<212> TYPE: PRT
<213> ORGANISM: Artificial Sequence
<220> FEATURE:
<223> OTHER INFORMATION: Synthetic - Light chain of AS11259

<400> SEQUENCE: 34

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val His Ser
                20                  25                  30

Asp Gly Asn Thr Tyr Leu Glu Trp Tyr Gln Gln Arg Pro Gly Gln Ser
            35                  40                  45

Pro Arg Leu Leu Ile Tyr Lys Val Ser Phe Arg Leu Ser Gly Val Pro
        50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 35
<211> LENGTH: 139
<212> TYPE: PRT
<213> ORGANISM: Artificial Sequence
<220> FEATURE:
<223> OTHER INFORMATION: Synthetic - CD79b ECD

<400> SEQUENCE: 35

```
Ala Arg Ser Glu Asp Arg Tyr Arg Asn Pro Lys Gly Ser Ala Cys Ser
1               5                   10                  15

Arg Ile Trp Gln Ser Pro Arg Phe Ile Ala Arg Lys Arg Gly Phe Thr
            20                  25                  30

Val Lys Met His Cys Tyr Met Asn Ser Ala Ser Gly Asn Val Ser Trp
        35                  40                  45

Leu Trp Lys Gln Glu Met Asp Glu Asn Pro Gln Gln Leu Lys Leu Glu
    50                  55                  60

Lys Gly Arg Met Glu Glu Ser Gln Asn Glu Ser Leu Ala Thr Leu Thr
65                  70                  75                  80

Ile Gln Gly Ile Arg Phe Glu Asp Asn Gly Ile Tyr Phe Cys Gln Gln
                85                  90                  95

Lys Cys Asn Asn Thr Ser Glu Val Tyr Gln Gly Cys Gly Thr Glu Leu
            100                 105                 110

Arg Val Met Gly Phe Ser Thr Leu Ala Gln Leu Lys Gln Arg Asn Thr
        115                 120                 125

Leu Lys Asp Val Asp His His His His His
    130                 135
```

<210> SEQ ID NO 36
<211> LENGTH: 1344
<212> TYPE: DNA
<213> ORGANISM: Artificial Sequence
<220> FEATURE:
<223> OTHER INFORMATION: Synthetic - Nucleotide sequence of heavy chain
      of AS11259

<400> SEQUENCE: 36

```
caagttcagc tggttcagtc tggcgccgaa gtgaagaaac tggcagcag cgtgaaggtg      60 tcctgcaaga ccagcggcaa caccttttacc agctacggca tcaactgggt caagcaggcc    120
```

```
cctggacaag gcttggagtg gatcggcgag atcttcccca ggagcggcaa catctactac    180
aacgagaaat tcaagggccg cgtgaccatc accgccgaca gagcacaag caccgcctac    240
atggaactga gcagcctgag aagcgaggac accgccgtgt actattgtgc caagggcggc    300
acaggcgact cgactactg gggacagggc acactggtca cagtgtctag cgcaagcact    360
aaaggacctt ccgtgttccc actggcacca tcctctaaga gcacttccgg aggaaccgcc    420
gctctgggat gtctggtgaa ggactacttc ccagagcccg tcacagtgtc atggaacagc    480
ggggccctga ccagcggagt ccatacattt cctgctgtgc tgcagagttc aggcctgtat    540
agcctgagct ccgtggtcac tgtcccatct agttcactgg ggactcagac ctacatctgc    600
aacgtgaatc acaaaccatc taataccaag gtcgacaaga agtggaaacc caaaagttgt    660
gataagacac atacttgccc accttgtcct gcaccagagc tgctggggag gccaagcgtg    720
ttcctgtttc cacccaaacc taaggacacc ctgatgatta ccgcacacc agaagtcact    780
tgcgtggtcg tggacgtgag ccacgaggat cccgaagtca agtttaactg gtacgtggat    840
ggcgtcgagg tgcataatgc caaaacaaag cccagggagg aacagtataa ctctacatac    900
cgcgtcgtga gtgtcctgac tgtgctgcac caggactggc tgaacggcaa ggaatacaaa    960
tgcaaggtgt ccaacaaggc cctgcccgcc cctatcgaga agaccatttc taaagccaag    1020
gggcagcctc gagaaccaca ggtgtataca ctgcctccaa gccgggacga gctgactaaa    1080
aaccaggtgt ccctgacctg tctggtgaag gggttctacc cctccgatat tgctgtggag    1140
tgggaatcta atggacagcc tgagaacaat tataagacca cccccctgt gctggactcc    1200
gatggatctt tctttctgta ctcaaaactg accgtggata gagccgatg gcagcagggc    1260
aatgtctttt cttgtagtgt gatgcacgag gcactgcaca accactacac ccagaagtca    1320
ctgtcactgt caccaggcaa gtga                                           1344
```

<210> SEQ ID NO 37
<211> LENGTH: 660
<212> TYPE: DNA
<213> ORGANISM: Artificial Sequence
<220> FEATURE:
<223> OTHER INFORMATION: Synthetic - Nucleotide sequence of light chain of AS11259

<400> SEQUENCE: 37

```
gacgtggtca tgacccagtc tccactgagc ctgccagtga cactgggaca gccagccagc    60
atctcctgtc ggagctccca gaacatcgtg cacagcgacg gcaataccta cctggagtgg    120
tatcagcagc ggcctggcca gtccccaaga ctgctgatct acaaggtgtc cttcaggctg    180
tctggagtgc cagaccgctt ttctggcagc ggctccggca ccgatttcac actgaagatc    240
tctcgggtgg aggccgagga tgtgggcgtg tactattgct cccagggcag ccatgtgccc    300
tggacctttg gcggcggcac aaaggtggag atcaagagaa ccgtggccgc ccctagcgtg    360
ttcatctttc cccctagcga cgagcagctg aagagcggca gcctccgt ggtgtgcctg    420
ctgaacaact ctaccctag ggaggccaag gtgcagtgga aggtggataa cgccctgcag    480
tccggcaatt ctcaggagag cgtgaccgag caggactcca aggattctac atatagcctg    540
tctagcaccc tgacactgtc caaggccgac tacgagaagc acaaggtgta tgcatgcgag    600
gtgacccacc agggcctgtc ctctcccgtg acaaagagct ttaaccgcgg cgagtgttag    660
```

<210> SEQ ID NO 38
<211> LENGTH: 351

```
<212> TYPE: DNA
<213> ORGANISM: Artificial Sequence
<220> FEATURE:
<223> OTHER INFORMATION: Synthetic - Nucleotide sequence of mVH

<400> SEQUENCE: 38
caggttcagc tgcagcagtc tggatctgag ctggcgaggc ctggggcttc agtgaagctg        60
tcctgcaaga cttctggcaa caccttcaca agttatggta taaactgggt gaagcagaga       120
actggacagg gccttgagtg gattggagag attttccta gaagtggtaa tatttactac        180
aatgagaagt tcaagggcaa ggccacactg actgcagaca aatcctccag cacagcgtac       240
atggagctcc gcagcctgac atctgaggac tctgcggtct atttctgtgc aaaaggggga       300
actggggact ttgactactg gggccaaggc accactctca cagtctcctc a                351

<210> SEQ ID NO 39
<211> LENGTH: 336
<212> TYPE: DNA
<213> ORGANISM: Artificial Sequence
<220> FEATURE:
<223> OTHER INFORMATION: Synthetic - Nucleotide sequence of mVL

<400> SEQUENCE: 39
gatgttttga tgacccaaac tccactctcc ctgcctgtca gtcttggaga tcaagcctcc        60
atctcttgca gatctagtca gaacattgta catagtgatg gaaacaccta tttagaatgg       120
tacctgcaga aaccaggcca gtctccaaaa ctcctgattt acaaagtttc cttccgactt       180
tctggggtcc cagacaggtt cagtggcagt ggatccggga cagatttcac actcaagatc       240
agaagagtgg aggctgagga tctgggaact tattattgtt ttcaaggttc acatgttccg       300
tggacgttcg gtggaggcac caagctggaa atcaaa                                 336
```

ANTI-CD79b ANTIBODIES, DRUG CONJUGATES, AND APPLICATIONS THEREOF

CROSS-REFERENCE TO RELATED APPLICATIONS

This application represents the U.S. national stage entry of International Application No. PCT/CN2019/114676 filed Oct. 31, 2019, which claims priority to Chinese Patent Application No. 201811296100.8 filed Nov. 1, 2018, the disclosure of which is incorporated herein by reference in its entirety and for all purposes.

REFERENCE TO A SEQUENCE LISTING SUBMITTED VIA EFS-WEB

The content of the ASCII text file of the sequence listing named "850766_00104_ST25.txt" which is 58.7 kb in size was created on Apr. 16, 2021 and electronically submitted via EFS-Web herewith the application is incorporated herein by reference in its entirety.

TECHNICAL FIELD

The present invention relates to anti-CD79b antibodies, drug conjugates, and the uses thereof.

BACKGROUND ART

CD79b (i.e., Igβ or B29) is a signaling component of the B cell receptor and acts by forming a covalent heterodimer with CD79a (i.e., Igα or mb-1). CD79b includes an extracellular immunoglobulin (Ig) domain, a transmembrane domain, and an intracellular signal domain. Surface expression of CD79b has been detected in almost all patients with non-Hodgkin's lymphoma (NHL) and chronic lymphocytic leukemia (CLL) by flow cytometry. In addition to the signaling function, when the B cell receptor is cross-linked, it is targeted to the class II major histocompatibility complex compartment (a lysosomal-like compartment), which is part of class II antigen presentation by B cell.

This characteristic of CD79b biology makes it a target for antibody-drug conjugates (ADCs), because antibodies against CD79b are internalized and delivered to lysosomal compartments which are known to contain proteases that release cytotoxic drugs. Antibody-drug conjugates (ADCs) are capable of targeted delivery of a drug to a tumor and intracellular accumulation occurs therein. Efforts to increase the therapeutic index of ADC (i.e., highest efficacy with minimal toxicity) have been focused on the specificity of polyclonal and monoclonal antibodies as well as drug linkage and drug release profiles.

Various ADCs have been prepared, such as humanized anti-CD79b antibody (humanized SN8) coupled to monomethyl auristatin E (MMAE) by protease cleavable linker, which is clinically effective in the treatment of NHL.

SUMMARY OF THE INVENTION

Provided herein are anti-CD79b antibodies or functional fragments thereof, the pharmaceutical compositions or drug conjugates thereof, and their use in the treatment of hematological tumors.

In one aspect, provided herein is an anti-CD79b antibody or antigen-binding fragment thereof, comprising:

HCDR1 comprising the amino acid sequence set forth in SEQ ID NO: 1;
HCDR2 comprising the amino acid sequence set forth in SEQ ID NO: 2;
HCDR3 comprising the amino acid sequence set forth in SEQ ID NO: 3;
LCDR1 comprising the amino acid sequence set forth in SEQ ID NO: 4;
LCDR2, comprising the amino acid sequence set forth in SEQ ID NO: 5; and
LCDR3, comprising the amino acid sequence set forth in SEQ ID NO: 6.

In one or more embodiments, the anti-CD79b antibody described herein is a monoclonal antibody, a human antibody, a humanized antibody, or a chimeric antibody.

In one or more embodiments, the amino acid sequence of HCDR1 of the anti-CD79b antibody or antigen-binding fragment thereof is set forth in SEQ ID NO: 1; the amino acid sequence of HCDR2 is set forth in SEQ ID NO: 2; the amino acid sequence of HCDR3 is set forth in SEQ ID NO: 3; the amino acid sequence of LCDR1 is set forth in SEQ ID NO: 4; the amino acid sequence of LCDR2 is set forth in SEQ ID NO: 5; and the amino acid sequence of LCDR3 is set forth in SEQ ID NO: 6.

In one or more embodiments, the amino acid sequence of the heavy chain variable region of the anti-CD79b antibody herein is set forth in SEQ ID NO: 7 or 11, and/or the amino acid sequence of the light chain variable region of the anti-CD79b antibody herein is set forth in SEQ ID NO: 8 or 12.

In one or more embodiments, the amino acid sequence of the heavy chain variable region of the anti-CD79b antibody herein is selected from the amino acid sequences set forth in any one of SEQ ID NOs: 13-17, and/or the amino acid sequence of the light chain variable region of the anti-CD79b antibodies herein is selected from the amino acid sequences set forth in any one of SEQ ID NOs: 18-22.

In one or more embodiments, the anti-CD78b antibody herein comprises (a) a heavy chain having at least 90%, preferably at least 95%, more preferably at least 98% sequence homology to SEQ ID NO: 25, 27, 29, 31 or 33, (b) a light chain having at least 90%, preferably at least 95%, more preferably at least 98% sequence homology to SEQ ID NO: 26, 28, 30, 32 or 34, or (c) the heavy chain in (a) and the light chain in (b).

In one or more embodiments, the amino acid sequence of the heavy chain of the anti-CD79b antibody herein is selected from an amino acid sequence having at least 90%, preferably at least 95% of sequence identity with the amino acid sequence set forth in any one of SEQ ID NOs: 25, 27, 29, 31, and 33, and/or the amino acid sequence of the light chain of the anti-CD79b antibody herein is selected from an amino acid sequence having at least 90%, preferably at least 95% of sequence identity with the amino acid sequence set forth in any one of SEQ ID NOs: 26, 28, 30, 32 and 34.

In one or more embodiments, the anti-CD79b antibody herein is selected from the group consisting of the following antibodies:

(1) the amino acid sequence of the heavy chain is set forth in SEQ ID NO: 25, and the amino acid sequence of the light chain is set forth in SEQ ID NO: 26;
(2) the amino acid sequence of the heavy chain is set forth in SEQ ID NO: 27, and the amino acid sequence of the light chain is set forth in SEQ ID NO: 28;
(3) the amino acid sequence of the heavy chain is set forth in SEQ ID NO: 29, and the amino acid sequence of the light chain is set forth in SEQ ID NO: 30;

(4) the amino acid sequence of the heavy chain is set forth in SEQ ID NO: 31, and the amino acid sequence of the light chain is set forth in SEQ ID NO: 32; and (5) the amino acid sequence of the heavy chain is set forth in SEQ ID NO: 33, and the amino acid sequence of the light chain is set forth in SEQ ID NO: 34.

In another aspect, provided herein is an antibody-drug conjugate that is a conjugate of the antibody described herein with a cytotoxic agent.

In one or more embodiments, the cytotoxic agent is a chemotherapeutic drug, a growth inhibitor, a toxin, or a radioisotope.

In another aspect, provided herein is a pharmaceutical composition comprising the antibody or antibody-drug conjugate as described herein, and a pharmaceutically acceptable carrier.

In another aspect, provided herein is an article comprising a container and a composition contained within the container, wherein the composition comprises one or more of the CD79b antibodies described herein. In certain embodiments, the article is a kit comprising a first container containing a composition comprising one or more of the CD79b antibodies described herein; and a second container containing a buffer.

In another aspect, provided herein is the use of the CD79b antibody or antigen-binding fragment thereof described herein in the manufacture of a medicament for the treatment or prevention of a CD79b-mediated disease. In certain embodiments, the disease is hematological tumor, especially a B cell proliferative disorder. In certain embodiments, the disease is lymphoma or leukemia. In certain embodiments, the disease is non-Hodgkin's lymphoma (NHL), aggressive NHL, recurrent aggressive NHL, recurrent painless NHL, refractory NHL, refractory painless NHL, small lymphocytic lymphoma, mantle cell lymphoma, chronic lymphocytic leukemia (CLL), hairy cell leukemia (HCL) or acute lymphocytic leukemia (ALL).

In another aspect, provided herein is a method of inhibiting the growth of a cell expressing CD79b, the method comprising contacting the cell with an antibody or antibody-drug conjugate described herein, thereby causing inhibition of growth of the cell. In certain embodiments, the cell is a B cell.

In another aspect, provided herein is a method of treating a CD79b-mediated disease, the method comprising administering to a mammal in need thereof a therapeutically effective amount of an antibody or antibody-drug conjugate described herein. In certain embodiments, the CD79b-mediated disease is cancer.

In still another aspect, provided herein is a method of determining the presence of CD79b in a sample suspected of containing CD79b, the method comprising exposing the sample to an antibody described herein, and determining the binding of the antibody to CD79b in the sample, wherein the binding of the antibody to CD79b in the sample is indicative of the presence of the protein in the sample.

In a further aspect, provided herein is a method of diagnosing a cell proliferative disorder associated with the increase in cells expressing CD79b, such as B cells. The said method comprises contacting test cells in a biological sample with the antibody described herein; determining the level of antibody bound to the test cells in the sample by testing the binding of the said antibody to CD79b; and comparing with the level of antibody bound to the cells in the control sample, wherein the level of bound antibody is normalized by relating to the number of cells expressing CD79b in test and control samples, and wherein the level of antibody bound in the test sample higher than the control sample indicates the presence of a cell proliferative disorder associated with cells expressing CD79b. In certain embodiments, the biological sample is blood or serum.

DETAILED EMBODIMENTS

Figure 1:
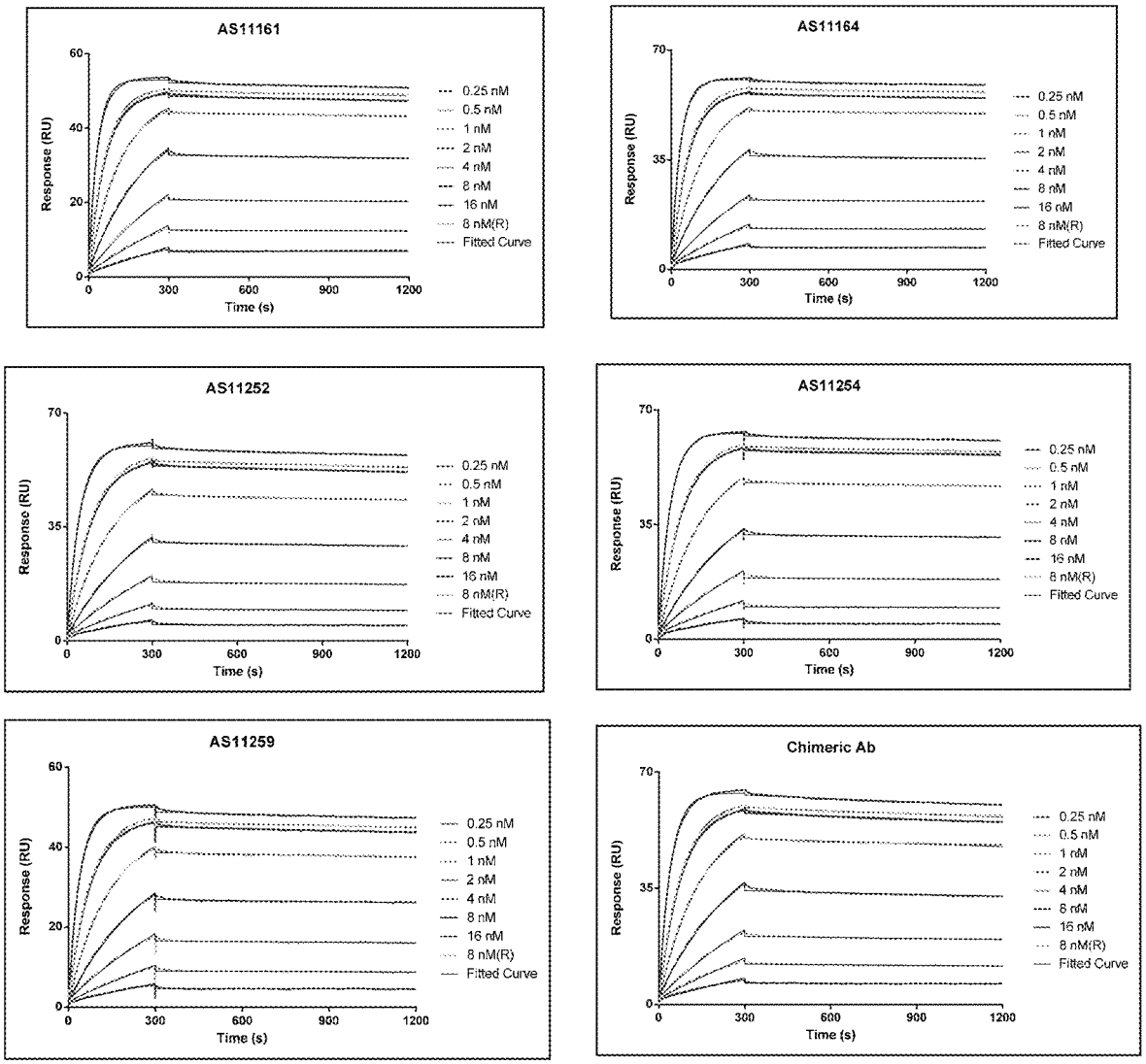
FIG. 1: Affinity test results for humanized antibodies.

It should be understood that within the scope of the present invention, the above mentioned various technical features of the present invention and the technical features specifically described in the following part (such as in the embodiments) may be combined with each other to constitute new technical solutions.

The practice of the present invention will employ, unless otherwise defined, conventional techniques of molecular biology (including recombinant techniques), microbiology, cell biology, biochemistry, and immunology, which are within the skill of the art. These techniques are fully explained in the literature, such as in Molecular Cloning: A Laboratory Manual, Second Edition (Sambrook et al., 1989); Oligonucleotide Synthesis (MJ Gait, ed., 1984); Animal Cell Culture (RI Freshney, ed., 1987); Methods in Enzymology (Academic Press, Inc.); Current Protocols in Molecular Biology (F. M. Ausubel et al., eds. 1987, and regularly updated); PCR: The Polymerase Chain Reaction (PCR: Polymerase Chain Reaction), (Mullis et al., ed., 1994); A Practical Guide to Molecular Cloning (Perbal Bernard V., 1988); Phage Display: A Laboratory Manual (Barbas et al., 2001).

As used herein, an "isolated" antibody refers to an antibody that has been identified and separated from a component of its natural environment. In a preferred embodiment, the antibody is purified to: (1) that the antibody weighs more than 95%, most preferably more than 99%, according to the Lowry method, and (2) the extent that is sufficient to obtain at least 15 residues of N-terminal or internal amino acid sequence by using a rotary cup sequencer, or (3) homogeneity according to SDS-PAGE under reducing or non-reducing conditions and staining with Coomassie Blue or preferably silver.

The term "CD79b" refers to any natural CD79b from any vertebrate source, including mammals, such as primates (e.g., humans, macaques), and rodents (e.g., mice and rats), unless otherwise indicated. The term "CD79b" encompasses "full length", unprocessed CD79b, and any form of CD79b processed from cells. The term also encompasses naturally occurring variants of CD79b, such as splice variants, allelic variants and isoforms. CD79b polypeptides described herein may be isolated from a variety of sources, such as human tissue types or other sources, or prepared by recombinant or synthetic methods. "Native sequence CD79b polypeptide" includes polypeptides having the same amino acid sequence as the one of the corresponding CD79b polypeptide derived from nature. Such native sequence CD79b polypeptide may be isolated from nature or may be prepared by recombination or synthetic methods. The term "native sequence CD79b polypeptide" specifically encompasses a naturally occurring truncated or secreted form of a particular CD79b polypeptide (e.g., an extracellular domain sequence), the naturally occurring variant forms (e.g., alternative splicing forms) and naturally occurring allelic variants of the polypeptide.

The "extracellular domain" or "ECD" of the CD79b polypeptide refers to a form of CD79b polypeptide substantially free of transmembrane and cytoplasmic domains. Typically, the CD79b polypeptide ECD has less than 1% of such transmembrane domains and/or cytoplasmic domains, preferably less than 0.5% of such domains. The precise boundaries of the transmembrane domain may vary, preferably, the extracellular domain of the CD79b polypeptide may comprise about 5 or less than 5 amino acids of either side of the transmembrane domain/extracellular domain boundary identified in the Examples or the specification. In certain embodiments, the amino acid sequence of the CD79b ECD described herein is set forth in SEQ ID NO:35.

The term "antibody" includes monoclonal antibodies (including full length antibodies having immunoglobulin Fc regions), antibody compositions having multi-epitope specificities, multispecific antibodies (e.g., bispecific antibodies), diabody and single chain molecules, as well as antibody fragments (e.g., Fab, F(ab')2, and Fv). The terms "immunoglobulin" (Ig) and "antibody" can be used interchangeably.

The term "CD79b antibody" or alike refers to an antibody that is capable of binding CD79b with sufficient affinity. Preferably, the CD79b antibody binds to irrelevant non-CD79b proteins to a degree less than about 10% of the binding of the antibody to CD79b, as measured, for example, by radioimmunoassay (MA). In certain embodiments, the antibody that binds to CD79b has a dissociation constant (Kd) of ≤10 nM, ≤1 nM, or ≤0.1 nM. In certain embodiments, the anti-CD79b antibody binds to a CD79b epitope that is conserved among CD79bs from different species.

A "variable region" or "variable domain" of an antibody refers to the amino terminal domain of the heavy or light chain of an antibody. The variable domains of the heavy and light chains can be referred to as "VH" and "VL", respectively. These domains are typically the most variable parts of the antibody (relative to other antibodies of the same type) and contain antigen binding sites.

The term "variable" refers to the situation where certain segments of the variable domains differ widely in antibody sequences. A variable domain mediates antigen binding and defines the specificity of a particular antibody to its particular antigen. However, the variability is not evenly distributed across the 110 amino acids spanning the variable domain. In fact, the variable region consists of relatively invariant segments of 15-30 amino acids in length called the framework regions (FRs) and extremely variable shorter regions of the lengths of 9-12 amino acids each that separate the framework regions called "highly variable regions (HVRs)". The variable domains of the native heavy and light chains each comprise four FR regions, most of which adopt a beta-sheet conformation. The HVRs in each chain are held together very closely by the FR regions and together with the HVRs of the other chain contribute to the formation of the antigen binding site of the antibody. The constant domains are not directly involved in the binding of the antibody to the antigen, but exhibit multiple effector functions.

The term "monoclonal antibody" as used herein refers to an antibody obtained from a population of substantially homogeneous antibodies, i.e., except possible naturally occurring mutations and/or post-translational modifications (e.g., isomerization, amidation) that may be present in minor amount, the individual antibodies that make up the population are identical. Monoclonal antibodies are highly specific and target to a single antigenic site. Each monoclonal antibody is directed against a single determinant on the antigen as compared to polyclonal antibody formulations, which typically include different antibodies directed against different epitopes. In addition to their specificity, the advantage of the monoclonal antibodies lies in that they are synthesized by hybridoma culture and are not contaminated by other immunoglobulins. "Monoclonal" indicates that the antibodies are obtained from a substantially homogeneous population of antibodies and should not be construed as requiring any particular method for the production of the antibody. For example, monoclonal antibodies to be used herein can be produced by a variety of techniques including, for example, hybridoma methods (e.g., Kohler and Milstein, Nature, 256:495-97 (1975)), DNA recombination (e.g., U.S. Pat. No. 4,816,567), phage display technology (e.g., Clackson et al, Nature, 352: 624-628 (1991)), and the technique for producing a human or human-like antibody from animal having partial or entire human immunoglobulin loci or genes coding human immunoglobulin sequences (for example, WO1998/24893).

The terms "full length antibody", "intact antibody" or "complete antibody" can be used interchangeably and refer to an antibody comprising an antigen binding site as well as CL and at least the heavy chain constant domains CH1, CH2 and CH3. The constant domain can be a native sequence constant domain (e.g., a human native sequence constant domain) or an amino acid sequence variant thereof. In some cases, an intact antibody can have one or more effector functions.

An "antibody fragment" comprises a portion of an intact antibody, preferably comprising an antigen binding region and/or a variable region of an intact antibody. Examples of antibody fragments include Fab, Fab', F(ab')2 and Fv fragments; diabodies; linear antibodies (see U.S. Pat. No. 5,641,870); single chain antibody (scFv) molecules; and multispecific antibodies formed by antibody fragments. Digestion of the antibody with papain produces two identical antigen-binding fragments called "Fab" fragments, and a residual "Fc" fragment. The Fab fragment consists of the entire light and heavy chain variable domains (VHs) and one heavy chain first constant domain (CH1). Each Fab fragment is monovalent in antigen binding, i.e., it has a single antigen binding site. Pepsin treatment of the antibody produces a larger F(ab')2 fragment that roughly corresponds to two Fab fragments linked by disulfide bonds, which has a different antigen binding activity and is still capable of cross-linking antigen. The Fab' fragment differs from the Fab fragment by the addition of some additional residues at the carboxyl terminus of the CH1 domain, including one or more cysteines from the antibody hinge region. The F(ab')2 antibody fragment was originally produced as a pair of Fab' fragments with a hinge cysteine between the Fab' fragments. Other chemical conjugates of antibody fragments are also known. The Fc fragment comprises the carboxyl terminal portion of two heavy chains held together by a disulfide bond. The effector function of an antibody is determined by the sequence in the Fc region, which is also the region recognized by an Fc receptor (FcR) found on certain types of cells.

An "Fc region" or Fc fragment is used herein to define a C-terminal region of an immunoglobulin heavy chain, including a native sequence Fc region and a variant Fc region. Although the boundaries of the immunoglobulin heavy chain Fc region may vary, the human IgG heavy chain Fc region is generally defined as a segment from the amino acid residue at its Cys226 or Pro230 position to the carboxy terminus. The C-terminal lysine of the Fc region (residue 447, according to the EU numbering system) can be eliminated, for example, during the production or purification of antibody, or by recombination engineering of nucleic acids encoding antibody heavy chains. Thus, a conjugate of an intact antibody can include an antibody conjugate in which all K447 residues are eliminated, an antibody conjugate without any K447 residue eliminated, or mixed antibody conjugates with a K447 residue or without K447 residue. A "functional Fc region" possesses an effector function of the native sequence Fc region. Exemplary effector functions include C1q binding, CDC, Fc receptor binding, ADCC, phagocytosis, downregulation of cell surface receptors (e.g., B cell receptors), and the like. A "native sequence Fc region" comprises an amino acid sequence identical to the amino acid sequence of an Fc region found in nature. The native sequence human Fc region comprises the native sequence human IgG1 Fc region; the native sequence human IgG2 Fc region; the native sequence human IgG3 Fc region; and the native sequence human IgG4 Fc region; and naturally occurring variants thereof. A "variant Fc region" comprises an amino acid sequence that differs from a native sequence Fc region by at least one amino acid modification, preferably one or more amino acid substitutions. Preferably, the variant Fc region has at least one amino acid substitution compared to the native sequence Fc region or to the Fc region of the parent polypeptide, e.g., having in the native sequence Fc region or in the Fc region of the parent polypeptide from about 1 to about 10 amino acid substitutions, preferably from about 1 to about 5 amino acid substitutions. The variant Fc regions preferably have at least about 80% homology to the native sequence Fc region and/or the Fc region of the parent polypeptide, most preferably at least about 90% homology to them, more preferably at least about 95% homology to them.

"Fv" is the minimal antibody fragment that contains the entire antigen recognition and binding site. This fragment consists of a dimer of a heavy chain variable domain and a light chain variable domain that are closely, non-covalently bound. Six hypervariable loops (3 loops for each of the heavy and light chains) are protruded from the folding of these two domains, contributing to the antigen-binding amino acid residues and conferring antigen binding specificity to the antibody. However, even a single variable domain (or half of an Fv comprising only three HVRs specific for an antigen) has the ability to recognize and bind antigen, although the affinity is lower than the intact binding site.

"Single-chain Fv" may also be abbreviated as "scFv", which is an antibody fragment in which the VH and VL domains of an antibody are joined into a single polypeptide chain. Preferably, the scFv polypeptide further comprises polypeptide linker between the VH and VL domains such that the sFv forms the desired antigen binding structure.

"Diabody" refers to an antibody fragment having two antigen binding sites, which comprises a heavy chain variable domain (VH) and a light chain variable domain (VL) linked in the same polypeptide chain (VH-VL). Small antibody fragments are prepared by constructing a scFv fragment using a short linker (about 5-10 residues) between the VH and VL domains, and because of the short linker, the variable domains are subjected to pairing between rather than inside the chains. This results in a bivalent fragment, a fragment having two antigen binding sites. Diabodies can be bivalent or bispecific. A bispecific diabody is a heterodimer of two "crossover" scFv fragments in which the VH and VL domains of both antibodies are present on different polypeptide chains.

A "functional fragment" or "antigen-binding fragment" of an antibody described herein includes a portion of an intact antibody, typically including the antigen binding or variable region of the intact antibody, or Fc region of the antibody retaining or having altered FcR binding ability. Examples of functional fragments of the antibody include linear antibodies, single-chain antibodies (scFv), and multispecific antibodies formed by antibody fragments, especially Fv, scFv, Fab, F(ab')2, Fab', scFv-Fc fragments or diabodies, or any fragment that is capable of increasing half-life by chemical modification or by incorporation into liposomes. The chemical modification includes the addition of poly(alkylene) glycols such as polyethylene glycol, i.e., PEGylation modification (referred to as Fv-PEG, scFv-PEG, Fab-PEG, F(ab') 2-PEG or a PEGylated fragment of Fab'-PEG) with CD79b binding activity.

Preferably, a functional fragment of the antibody described herein consists of or comprises a partial sequence of a heavy chain variable region or a light chain variable region of the antibody from which it is derived, the partial sequence being sufficient to retain the same binding specificity and full affinity as the antibody from which it is derived. Such functional fragments will comprise a minimum of 5 amino acids, preferably 10, 15, 25, 50 and 100 contiguous amino acids of the antibody sequence from which they are derived.

Monoclonal antibodies include "chimeric" antibodies (immunoglobulins) herein. In a chimeric antibody, a portion of a heavy chain and/or a light chain is identical or homologous to a corresponding sequence of the antibody derived from a particular species or belonging to a particular antibody class or subclass, and another portion is identical or homologous to a corresponding sequence of another antibody derived from another particular species or belonging to another particular antibody class or subclass.

A "humanized antibody" is a specific class of "chimeric antibodies". A "humanized" form of a non-human (e.g., rodent) antibody refers to a chimeric antibody that minimally comprises sequences derived from a non-human antibody. To a large extent, humanized antibodies refer to immunoglobulins wherein the hypervariable region residues of human immunoglobulins (recipient antibodies) are replaced by the hypervariable region residues of non-human species (donor antibodies) such as mice, rats, rabbits or non-human primates that have the desired antibody specificity, affinity and ability. In some cases, the framework region (FR) residues of human immunoglobulin are replaced with corresponding non-human residues. Furthermore, a humanized antibody may comprise residues that are not found in the recipient antibody or in the donor antibody. These modifications are made to further improve the performance of the antibody. In general, a humanized antibody will comprise at least one, typically two, substantially entire variable domain, wherein all or substantially all of the hypervariable loops correspond to the hypervariable loops of a non-human immunoglobulin, and all or substantially all FRs are the FR of human immunoglobulin sequences. The humanized antibody optionally will also comprise at least a portion of the immunoglobulin constant region (Fc), typically a constant region of a human immunoglobulin. Humanized antibodies can be obtained from mouse-derived antibodies produced by immunizing mice via computer simulation design in combination of phage display technology.

"Human antibody" refers to an antibody that has an amino acid sequence corresponding to the amino acid sequence of an antibody produced by a human and/or is produced using any technique known in the art for generating human antibodies. Human antibodies specifically exclude humanized antibodies comprising non-human antigen binding residues. Human antibodies can be generated using a variety of techniques known in the art, including phage display libraries.

"Binding affinity" generally refers to the strength of the sum of all non-covalent interactions between a single binding site of a molecule (e.g., an antibody) and its binding partner (e.g., an antigen). As used herein, "binding affinity" refers to the intrinsic binding affinity that reflects a 1:1 interaction between a member of a binding pair (e.g., an antibody and an antigen), unless otherwise indicated. The affinity of the molecule X for its partner Y can be generally expressed by the dissociation constant (Kd). Low-affinity antibodies typically bind to antigen slowly and tend to dissociate easily, while high-affinity antibodies generally bind antigen much more rapidly and tend to maintain longer binding. Affinity can be measured by common methods known in the art, including radiolabeled antigen binding assays (MA).

"Control sequence" refers to a DNA sequence necessary for expression of an operably linked coding sequence in a particular host organism. For example, control sequences suitable for prokaryotes include a promoter, an optional operator sequence, and a ribosome binding site. Eukaryotic cells are known to utilize promoters, polyadenylation signals, and enhancers.

A nucleic acid is "operably linked" if it is in a functional relationship with another nucleic acid sequence. For example, if the leader sequence or secretory leader DNA is expressed as a pro-protein involved in the secretion of the polypeptide, it is operably linked to the DNA of the polypeptide; if the promoter or enhancer affects the transcription of the coding sequence, it is operably linked to the sequence; or, if the position of the ribosome binding site facilitates translation, it is operably linked to the coding sequence. In general, "operably linked" means that the linked DNA sequences are adjacent, and, in the case of a secretory leader, it means adjacent and in a readable state. However, enhancers do not have to be adjacent. The ligation can be achieved by connection at a convenient restriction site. In the absence of such sites, synthetic oligonucleotide adaptors or linkers are used in accordance with conventional practice.

"Vector" as used herein refers to a nucleic acid molecule capable of transporting other nucleic acids to which it is linked. One type of vector is a "plasmid", which refers to a circular double stranded DNA loop into which additional DNA segments can be ligated. Another type of vector is a phage vector. Another type of vector is a viral vector in which additional DNA segments can be ligated into the viral genome. Certain vectors are capable of autonomous replication in a host cell into which they are introduced (e.g., a bacterial vector having a bacterial replication origin and an episomal mammalian vector). Other vectors (e.g., non-episomal mammalian vectors) can be integrated into the genome of the host cell upon introduction into the host cell, thereby replicating along with the host genome. In addition, certain vectors are capable of directing the expression of genes to which they are operably linked. Such vectors are referred to herein as "recombinant expression vectors" (or simply "recombinant vectors"). Typically, expression vectors useful in recombinant DNA techniques are often in the form of plasmids. In the present specification, "plasmid" and "vector" are used interchangeably as the plasmid is the most common form of vector.

"Polynucleotide" or "nucleic acid" is used interchangeably herein to refer to a polymer of nucleotides of any length, including DNA and RNA. The nucleotide may be a deoxyribonucleotide, a ribonucleotide, a modified nucleotide or base, and/or an analog thereof, or may be any substrate incorporated into the polymer by DNA or RNA polymerase or by a synthetic reaction. Polynucleotides may comprise modified nucleotides, such as methylated nucleotides and analogs thereof. Modification of the nucleotide structure, if any, can be performed before or after assembly of the polymer. The nucleotide sequence can be interrupted by a non-nucleotide component. The polynucleotide can be further modified after synthesis, such as by coupling to a label.

"Oligonucleotide" generally refers to a short polynucleotide, typically single stranded, synthetic, of a length generally but not necessarily less than about 200 nucleotides.

As used herein, the term "tumor" refers to a physiological condition in a mammal that is typically characterized by unregulated cell growth. Tumors can be divided into benign tumors and malignant tumors, and malignant tumors are also called cancers. Tumors can be divided into solid tumors or hematological tumors. In certain embodiments, the invention relates in particular to the treatment of cancer of the hematopoietic system or blood-related cancers. As used herein, "hematopoietic system" includes thymus and bone marrow and peripheral lymphoid tissues such as the spleen, lymph nodes, lymphoid tissues associated with the mucosa, such as intestinal-associated lymphoid tissue, tonsils, Peyer's patches, and other mucosa-related attachments and lymphoid tissues, such as the bronchial lining. Thus, cancer of the hematopoietic system or blood-related cancers described herein can include lymphoma, leukemia, myeloma or lymphoid malignancies, as well as cancers of the spleen and cancers of the lymph nodes. More specific examples of cancers of the hematopoietic system or blood-related cancers include B-cell-associated cancers including, for example, advanced, intermediate, and low-grade lymphomas, including B-cell lymphomas, such as mucosa-associated lymphoid tissue B-cell lymphomas and non-Hodgkin's lymphoma (NHL), mantle cell lymphoma, Burkitt's lymphoma, small lymphocytic lymphoma, marginal lymphoma, diffuse large cell lymphoma, follicular lymphoma, and Hodgkin's lymphoma and T-cell lymphoma; and leukemia, including secondary leukemia, chronic lymphocytic leukemia (CLL) such as B-cell leukemia (CD5+ B lymphocytes), myeloid leukemia such as acute myeloid leukemia, chronic myeloid leukemia, lymphoid leukemia such as acute lymphocytic leukemia (ALL) and spinal dysplasia; and other hematological and/or B cell or T cell related cancers. Cancers of the hematopoietic system or blood-related cancers also include cancers of other hematopoietic cells, including polymorphonuclear leukocytes, such as basophils, eosinophils, neutrophils and monocytes, dendritic cell, platelets, red blood cells and natural killer cells. Specifically, it can include cancerous B cell proliferative disorder selected from the group consisting of non-Hodgkin's lymphoma (NHL), aggressive NHL, recurrent aggressive NHL, recurrent painless NHL, refractory NHL, refractory painless NHL, chronic lymphocytic leukemia (CLL), small lymphocytic lymphoma, hairy cell leukemia (HCL), acute lymphoblastic leukemia (ALL), and mantle cell lymphoma.

Herein, cancer also includes cancer, blastoma, and sarcoma. Thus, other examples of cancer include squamous cell carcinoma, small cell lung cancer, non-small cell lung cancer, lung adenocarcinoma, lung squamous cell carcinoma, peritoneal cancer, hepatocellular carcinoma, gastrointestinal cancer, pancreatic cancer, glioma, cervic cancer, ovarian cancer, liver cancer, bladder cancer, hepatosarcoma, breast cancer, colon cancer, colorectal cancer, endometrial cancer or uterine cancer, salivary gland cancer, kidney cancer, prostate cancer, vulvar cancer, thyroid cancer and various types of head and neck cancers, etc.

"Treatment" or "alleviation" refers to the alleviation (reduction) or cure of the pathological condition or disorder directed to. If a patient exhibits an observable and/or measurable decrease or disappearance in one or more of the following after receiving a therapeutic amount of an anti-CD79b antibody according to the method described herein, the subject successfully "treats" the tumors (especially cancer) expressing CD79b polypeptide: reduced number of tumor cells or disappearance of tumor cells; reduced tumor volume; inhibition of tumor cell infiltration; inhibition of tumor metastasis; inhibition of tumor growth to a certain extent; and/or the alleviation of one or more symptoms associated with specific tumors to a certain extent; reduction in morbidity and mortality; and the improvement of life quality. In the case where the anti-CD79b antibody prevents tumor cell growth and/or kills existing tumor cells, it may suppress cells and/or poison cells. The alleviation of these signs or symptoms can also be felt by the patient.

"Therapeutically effective amount" means a dose sufficient to indicate its benefit to the subject to which it is administered. The actual amount administered, as well as the rate and time course of administration will depend on the condition and severity of the subject being treated. The prescription for treatment (e.g., the determination of the dose, etc.) is ultimately the responsibility of the GP and other physicians and relies on them to make decisions, usually considering the disease being treated, the condition of the individual patient, the site of delivery, the method of administration, and the other factors known to the physicians. In the case of tumors, the therapeutically effective amount of the drug can reduce the number of tumor cells; reduce the tumor volume; inhibit the infiltration of cancer cells into surrounding organs; inhibit tumor metastasis; inhibit tumor growth to a certain extent; and/or reduce one or more symptoms related to tumors to some extent. By "prophylactically effective amount" it is meant an amount effective to achieve the desired prophylactic effect at the necessary dose and time. Usually, but not necessarily, since the prophylactic dose is administered to the subject prior to the onset of the disease or early in the disease, the prophylactically effective amount will be less than the therapeutically effective amount.

The "growth inhibiting amount" of an anti-CD79b antibody refers to an amount capable of inhibiting the growth of cells, particularly tumors, such as cancer cells, in vitro or in vivo. The "growth inhibition amount" of the anti-CD79b antibody in order to inhibit neoplastic cell growth can be determined empirically and in a conventional manner.

The "cytotoxic amount" of an anti-CD79b antibody refers to an amount capable of causing destruction of cells, particularly tumor cells, such as cancer cells, in vitro or in vivo. The "cytotoxic amount" of the anti-CD79b antibody in order to inhibit neoplastic cell growth can be determined empirically and in a conventional manner.

As used herein, "individual" or "subject" refers to a vertebrate. In certain embodiments, the vertebrate is a mammal. Mammals include, but are not limited to, livestock (such as cattle), sports animals, pets (such as cats, dogs, and horses), primates, mice, and rats. Preferably, the mammal refers to a human.

Administration "in combination with" one or more other therapeutic agents includes simultaneous (co-) administration and sequential administration in any order.

Regarding "sequence identity" of a reference polypeptide sequence, it is defined as when aligning the sequence and introducing gap if necessary to obtain maximum percent sequence identity, and without considering any conservative substitution as part of sequence identity, the percentage of amino acid residues in the candidate sequence identical to the amino acid residues in the reference polypeptide sequence. Comparisons for the purpose of determining percent amino acid sequence identity can be carried out in a variety of ways within the skill of the art, for example using publicly available computer software such as BLAST, BLAST-2, ALIGN or Megalign (DNASTAR) software. Included herein are amino acid sequences with at least 80%, e.g., at least 81%, 82%, 83%, 84%, 85%, 86%, 87%, 88%, 89%, 90%, 91%, 92%, 93%, 94%, 95%, 96%, 97%, 98%, 99% or 100% sequence identity to the light chain variable region, heavy chain variable region or heavy chain and light chain of the antibody (especially the individual sequences specifically recited herein) as described herein. Preferably, mutations can be made in the anti-CD79b antibodies described herein, for example, using any of the techniques and guidelines for conservative and non-conservative mutations as described, for example, in U.S. Pat. No. 5,364,934. In certain embodiments, the variation does not occur within the CDRs set forth herein as SEQ ID NOs: 1-6. The variation can be substitution, deletion or insertion of one or more codons encoding an antibody or polypeptide that results in a change in the amino acid sequence relative to the native sequence antibody. Optionally, the variation is the substitution of at least one amino acid in one or more domains of the anti-CD79b antibody by any other amino acid. By comparing the sequence of anti-CD79b antibody to the sequence of a homologous known protein molecule and minimizing the number of amino acid sequence changes made in the highly homologous region, the principles of which amino acid residues can be inserted, replaced or deleted without adverse effect on the expected activity can be found. Amino acid substitutions can be the result of replacing one amino acid with another amino acid having similar structural and/or chemical properties, such as replacing leucine with serine, i.e., conservative amino acid substitution. Insertions or deletions may optionally be in the range of from about 1 to 5 amino acids. A tolerable variation can be determined by systematically performing amino acid insertions, substitutions or deletions in the sequence and testing the resulting variants for activity exhibited by full length or mature native sequences.

Variation can be performed using methods known in the art, such as oligonucleotide-mediated (site-directed) mutagenesis, alanine scanning, and PCR mutagenesis. The cloned DNA can be subjected to site-directed mutagenesis, cassette mutagenesis, restriction selective mutagenesis or other known techniques to produce anti-CD79b antibody variant DNA.

Any cysteine residue that is not involved in maintaining the correct conformation of the anti-CD79b antibody can also be substituted, usually by serine, to improve the oxidative stability of the molecule and prevent aberrant crosslinking. On the contrary, cysteine bonding can be added to an anti-CD79b antibody to improve its stability (especially when the antibody is an antibody fragment such as an Fv fragment).

In certain embodiments, a surrogate variant involves substitution of one or more hypervariable region residues of the parent antibody (e.g., humanized or human antibodies). In general, the resulting variants selected for further development will have improved biological properties relative to the parent antibody from which they are produced. A convenient method of generating such surrogate variants involves affinity maturation using phage display. Briefly, several hypervariable region sites (e.g., 6-7 sites) are mutated to produce all possible amino acid substitutions at each site. The antibody variants thus generated are displayed in a monovalent form on the filamentous phage particles as a fusion with the M13 gene III product packaged within each particle. Phage display variants are then screened for biological activity (e.g., binding affinity). To identify candidate hypervariable region sites for modification, alanine scanning mutagenesis can be performed to identify hypervariable region residues that have important contributions to antigen binding. Alternatively, or additionally, the crystal structure of the antigen-antibody complex is analyzed to identify the point of contact between the antibody and the CD79b polypeptide. Such contact residues and adjacent residues are candidate sites that are substituted in accordance with the techniques detailed herein. Once such variants are produced, the panel of variants is screened as described herein, and antibodies with superior properties in one or more of the relevant assays can be selected for further development. "Cytotoxic agent" refers to a substance that inhibits or prevents the function of cells and/or causes destruction of cells. The term includes: radioisotopes such as radioactive isotopes of $At^{211}$, $I^{131}$, $I^{125}$, $Y^{90}$, $Re^{186}$, $Re^{188}$, $Sm^{153}$, $Bi^{212}$, $P^{32}$ and Lu; chemotherapeutic agents such as methotrexate, adriamycin, vinca alkaloids (Such as vincristine, vinblastine, etoposide), doxorubicin, melphalan, mitomycin C, chlorambucil or daunorubicin; enzymes and fragments thereof, such as lysozyme; antibiotics; and toxins, such as small molecule toxins or enzymatic active toxins of bacterial, fungal, plant or animal origin, including fragments and/or variants thereof; and antitumor or anticancer drugs well known in the art.

"Pharmaceutical composition" means a combination of at least one drug and, optionally, a pharmaceutically acceptable carrier or excipient that are combined together to achieve a particular purpose. In certain embodiments, the pharmaceutical compositions include combinations that are separated in time and/or space, as long as they are capable of acting together to achieve the objectives of the present invention. For example, the components contained in the pharmaceutical composition (e.g., antibodies, nucleic acid molecules, nucleic acid molecule combinations, and/or conjugates described herein) can be administered to the subject as a whole or separately. When the components contained in the pharmaceutical composition are separately administered to a subject, the components may be administered to the subject simultaneously or sequentially. Preferably, the pharmaceutically acceptable carrier is water, a buffered aqueous solution, an isotonic saline solution such as PBS (phosphate buffer), glucose, mannitol, dextrose, lactose, starch, magnesium stearate, cellulose, magnesium carbonate, 0.3% glycerol, hyaluronic acid, ethanol or polyalkylene glycols such as polypropylene glycol, triglycerides and the like. The type of pharmaceutically acceptable carrier employed depends especially on whether the composition according to the invention is formulated for oral, nasal, intradermal, subcutaneous, intramuscular or intravenous administration. The composition according to the invention may comprise a wetting agent, an emulsifier or a buffer substance as an additive.

The pharmaceutical composition described herein may be administered by any suitable route, for example, orally, nasally, intradermally, subcutaneously, intramuscularly or intravenously.

Provided herein are anti-CD79b antibodies or functional fragments thereof, pharmaceutical compositions or antibody-drug conjugates thereof, and methods of use thereof in the treatment of hematopoietic tumors.

The antibodies herein are antibodies that specifically bind to the use of CD79b in the treatment of tumors, and may be monoclonal antibodies, antibody fragments (including Fab, Fab', F(ab')2 and Fv fragments), diabodies, single domain antibodies, chimeric antibodies, humanized antibodies, single chain antibodies or antibodies that competitively inhibit the binding of an anti-CD79b polypeptide antibody to its corresponding antigenic epitope. The antibodies described herein may optionally be conjugated to a cytotoxic agent, such as a toxin, including, for example, auristatin, maytansinoids, dolastatin derivatives or calicheamicin, antibiotics, radioisotopes, lysozymes, and the like. The antibodies described herein may optionally be produced in CHO cells or bacterial cells, and preferably induce cell death to the cells bound thereto. For detection purposes, the antibodies described herein may be detectably labeled and attached to a solid support.

The anti-CD79b antibody herein comprises at least one, at least two, at least three, at least four, at least five or all six of the amino acid sequences set forth in SEQ ID NOs: 1-6. In certain embodiments, the heavy chain variable region of the anti-CD79b antibody herein comprises any one, any two or all three of SEQ ID NOs: 1-3, and/or the light chain variable region thereof comprises any one, any two or all three of SEQ ID NOs: 4-6. In certain embodiments, the heavy chain variable region of the CD79b antibody herein comprises the amino acid sequences set forth in SEQ ID NOs: 1-3, and/or the light chain variable region thereof comprises the amino acid sequences set forth in SEQ ID NOs: 4-6. In certain embodiments, the heavy chain variable region of an anti-CD79b antibody herein comprises the amino acid sequence set forth in SEQ ID NOs: 1-3, and the light chain variable region comprises the amino acid sequence set forth in SEQ ID NOs: 4-6. In certain embodiments, the anti-CD79b antibody herein comprises: HCDR1 comprising the amino acid sequence set forth in SEQ ID NO: 1; HCDR2 comprising the amino acid sequence set forth in SEQ ID NO: 2; HCDR3 comprising the amino acid sequence forth in SEQ ID NO: 3; LCDR1 comprising the amino acid sequence set forth in SEQ ID NO: 4; LCDR2 comprising the amino acid sequence set forth in SEQ ID NO: 5; and LCDR3 comprising amino acid sequence set forth in SEQ ID NO: 6. In certain embodiments, the anti-CD79b antibody herein comprises the CDR sequences set forth in SEQ ID NOs: 1-6.

In certain embodiments, the antibody herein is murine antibody 104E1, the amino acid sequence of the heavy chain variable region thereof can be as set forth in SEQ ID NO: 7, and/or the amino acid sequence of its light chain variable region can be as set forth in SEQ ID NO: 8.

In certain embodiments, the antibody herein is a humanized antibody, wherein at least one, at least two, at least three, at least four, at least five or all six of SEQ ID NOs: 1-6 are used to replace the corresponding CDR regions in the heavy chain variable region and/or the light chain variable region of human antibody. In certain embodiments, the amino acid sequence used to prepare the heavy chain variable region of the humanized antibody is set forth in SEQ ID NO:9, and the amino acid sequence used to prepare the light chain variable region of the humanized antibody is as set forth in SEQ. ID NO: 10. In certain embodiments, the amino acid sequence of the heavy chain variable region of the humanized antibody described herein is set forth in SEQ ID NO: 11, and/or the amino acid sequence of the light chain variable region of the humanized antibody is as SEQ ID NO:12.

In certain embodiments, in order to find an amino acid position in the murine FR region that plays an important role in antibody affinity, PDC database is searched for a crystal structure similar in homology to the murine antibody 104E1 described herein. As a result, the scFv crystal structure of the anti-polysialic acid antibody Ab735 was found, which has a homology of 77% with the 104E1 antibody sequence and has a sufficiently high resolution. Herein, using this crystal as a structural template, the two sequences were compared to establish a homology model of the 3WBD scFvs of the 104E1 antibody. According to this homologous model, amino acid sites in the FR domain of the 104E1 sequence which were surrounded by the CDR domain, or within the distance from the CDR domain less than 5 Å were found, then these amino acid sites that may play an important role in antibody affinity were reverse mutated in the CDR-grafted sequences (SEQ ID NO: 11 and SEQ ID NO: 12) while avoiding glycosylation, deamidation, oxidation sites, etc. A total of 15 sites that may need to be reversely mutated were identified in the heavy chain variable region, including A24T, RV67KA, S84R, T98K, K12A, S16A, V20L, A24T, R38K, M48I, V68A, I70L, Y95F, T98K and V113L; a total of 7 sites that may need to be reversely mutated were identified in the light chain variable region, including V3L, F41Y, RR50KL, FQ41YL, R51L, V88L and V109L. Fab libraries were then constructed according to Kingsley's standard protocol and screened by phage display platform. The sequences after humanization with an affinity of not less than the murine 104E1 antibody were screened and sequenced for sequence confirmation. Accordingly, in certain embodiments, the amino acid sequence of the heavy chain variable region of the anti-CD79b antibody described herein can be selected from the amino acid sequences set forth in any one of SEQ ID NOs: 13-17, and/or the amino acid sequence of the light chain variable region thereof can be selected from the amino acid sequences set forth in any of SEQ ID NOs: 18-22. The present invention also includes heavy chain variable region sequences having at least 90%, preferably at least 95% sequence identity to the heavy chain variable regions, and light chain variable region sequences having at least 90%, preferably at least 95% sequence identity to the light chain variable regions. In certain embodiments, mutations in the heavy chain variable region and the light chain variable region occur within the FR and not in the CDRs.

The antibodies described herein may also contain a constant region. The constant region can be the constant region of human IgM, IgD, IgG, IgA, and IgE. For example, the constant region can be the constant region of human IgG1, IgG2, IgG3, IgG4, IgA1 or IgA2. In certain embodiments, the heavy chain of an anti-CD79b antibody described herein comprises a heavy chain variable region and a heavy chain Fc region as described herein, the light chain comprises a light chain variable region and a light chain Fc region as described herein. The amino acid sequence of an exemplary heavy chain Fc region can be as set forth in SEQ ID NO: 23, and the amino acid sequence of an exemplary light chain Fc region can be as set forth in SEQ ID NO: 24. In certain embodiments, a heavy chain Fc region suitable for use in the invention further comprises a heavy chain Fc region having at least 90%, preferably at least 95% sequence identity to the amino acid sequence as set forth in SEQ ID NO: 23, and/or the light chain Fc region suitable for use herein further comprises a light chain Fc region having at least 90%, preferably at least 95% sequence identity to the amino acid sequence as set forth in SEQ ID NO:24. Preferably, mutations known in the art that alter the effector function of the Fc region can occur in the heavy and/or light chain Fc regions. For example, an Fc region with reduced effector function has a substitution mutation in one or more of residues 238, 265, 269, 270, 297, 327, and 329 (see U.S. Pat. No. 6,737,056). One or more amino acid substitutions with improved ADCC may occur at residues 298, 333 and/or 334 of the Fc region (residues are numbered by EU numbering).

In certain embodiments, the amino acid sequence of the heavy chain of an anti-CD79b antibody described herein can be selected from amino acid sequences having at least 90%, preferably 95% sequence identity with the amino acid sequence set forth in any one of SEQ ID NOs: 25, 27, 29, 31, and 33, and/or the amino acid sequence of its light chain can be selected from at least 90%, preferably 95% sequence identity with the amino acid sequence set forth in any one of SEQ ID NOs: 26, 28, 30, 32 and 34.

Accordingly, in certain embodiments, an anti-CD79b antibody herein is selected from the group consisting of: (1) the antibody of which the amino acid sequence of the heavy chain is set forth in SEQ ID NO: 25, and the amino acid sequence of the light chain is set forth in SEQ ID NO: 26; (2) the antibody of which the amino acid sequence of the heavy chain is set forth in SEQ ID NO: 27, and the amino acid sequence of the light chain is set forth in SEQ ID NO: 28; (3) the antibody of which the amino acid sequence of the heavy chain is set forth in SEQ ID NO: 29 and the amino acid sequence of the light chain and the light chain is as shown in SEQ ID NO: 30; (4) the antibody of which the amino acid sequence of the heavy chain is set forth in SEQ ID NO: 31, and the amino acid sequence of the light chain is set forth in SEQ ID NO: 32; and (5) the antibody of which the amino acid sequence of the heavy chain is set forth in SEQ ID NO: 33, and the amino acid sequence of the light chain is set forth in SEQ ID NO: 34.

Also provided herein are coding sequences for CDRs, light chain variable regions, heavy chain variable regions, light and heavy chains, and complementary sequences thereof (nucleic acid sequences), vectors comprising the coding sequences or complementary sequences thereof, and a host cell containing the nucleic acid or vector. Exemplary coding sequences are set forth in SEQ ID NOs: 36, 37, 38 and 39, which are the coding sequences of SEQ ID NOS: 33, 34, 7 and 8, respectively.

Standard recombinant techniques can be used to obtain polynucleotide sequences encoding the antibodies or functional fragments thereof described herein. The desired polynucleotide sequence can be isolated from antibody producing cells such as hybridoma cells and be sequenced. Alternatively, the polynucleotide can be synthesized using a nucleotide synthesizer or PCR technique. Once obtained, the sequence encoding the polypeptide is inserted into a recombinant vector capable of replicating in a prokaryotic host and expressing the heterologous polynucleotide. For the purposes herein, a variety of vectors available and known in the art can be used. The choice of a suitable vector will depend primarily on the size of the nucleic acid to be inserted into the vector and the particular host cell into which the vector will be transformed. Each vector contains a variety of building blocks depending on its function (amplification or expression of the heterologous polynucleotide, or both) and its compatibility with the particular host cell in which it resides.

The vector may be in the form of, for example, a plasmid, a cosmid, a viral particle or a bacteriophage. Suitable nucleic acid sequence can be inserted into the vector by a variety of methods. Typically, the DNA sequence of interest is inserted into a suitable restriction endonuclease site using techniques known in the art. Vector components typically include, but are not limited to, one or more of the following: a signal sequence, a replication origin, one or more marker genes, an enhancer element, a promoter, and a transcription termination sequence. Suitable carriers comprising one or more of these components can be constructed using standard ligation techniques known to the skilled artisan. The vector may be a cloning vector or an expression vector.

CD79b can be produced not only directly by recombination, but also as a fusion polypeptide with a heterologous polypeptide, which can be a signal sequence or other polypeptide having a specific cleavage site at the N-terminus of the mature protein or polypeptide. Typically, the signal sequence can be a component of the vector, or it can be part of the DNA encoding the anti-CD79b antibody inserted into the vector. The signal sequence may be a prokaryotic signal sequence selected from, for example, alkaline phosphatase, penicillinase, lpp or a thermostable enterotoxin II leader sequence. For yeast secretion, the signal sequence may be, for example, a yeast invertase leader sequence, an alpha factor leader sequence (including the α-factor leader sequence of *Saccharomyces cerevisiae* and *Kluyveromyces*) or an acid phosphatase leader sequence, *Candida albicans* glucoamylase leader sequence, etc. In mammalian cell expression, mammalian signal sequences can be used to direct protein secretion, such as signal sequences from secreted polypeptides of the same or related species, as well as viral secretion leader sequences.

Generally, mammalian expression vectors do not require the replication origin component. For example, the SV40 origin can usually be used simply because it contains an early promoter. Expression and cloning vectors will typically contain a selection gene, also referred to as a selection marker. A typical selection gene encodes a protein that: (a) confers resistance to an antibiotic or other toxin, such as ampicillin, neomycin, methotrexate or tetracycline; (b) complements auxotrophs; or (c) provides key nutrients not able to be obtained from a complex medium, such as a gene encoding a D-alanine racemase for *Bacillus*.

An example of a selection protocol utilizes drugs to block the growth of host cells. Those cells that have been successfully transformed by a heterologous gene produce a protein that confers drug resistance and are thus spared from the selection protocol. Examples of such dominant selection use the drugs neomycin, mycophenolic acid and hygromycin.

Expression and cloning vectors typically comprise a promoter operably linked to a nucleic acid sequence encoding an anti-CD79b antibody to direct mRNA synthesis. Promoters that are recognized by a variety of potential host cells are well known. Examples of promoter sequences suitable for use in yeast hosts include promoters of 3-phosphoglycerate kinase or other glycolytic enzymes such as enolase, glyceraldehyde-3-phosphate dehydrogenase, hexokinase, pyruvate decarboxylase phosphofructokinase, glucose-6-phosphate isomerase, 3-phosphoglycerate mutase, pyruvate kinase, triose phosphate isomerase, phosphoglucose isomerase, and glucokinase.

Transcription of anti-CD79b antibodies by vectors in mammalian host cells is under the control of promoters obtained from for example, virus (e.g., polyomavirus, fowlpox virus, adenovirus (e.g. adenovirus type 2), bovine papilloma virus, avian sarcoma virus, cytomegalovirus, retrovirus, hepatitis B virus and semian virus 40 (SV40)) genome, heterologous mammalian promoters (such as actin promoters or immunoglobulin promoters), and heat shock promoters. In certain embodiments, the early and late promoters of the SV40 virus are used, which further comprise an SV40 viral origin of replication.

Transcription of DNA encoding an anti-CD79b antibody by higher eukaryotic cells can be increased by inserting an enhancer sequence into the vector. An enhancer is a cis-acting element of DNA, usually about 10 to 300 bp, which acts on a promoter to increase transcription. Many enhancer sequences from mammalian genes (globin, elastase, albumin, alpha-fetoprotein, and insulin) are known. However, enhancers from eukaryotic viruses are commonly used. Examples include the enhancer on the late side of the SV40 replication origin (bp 100-270), the cytomegalovirus early promoter enhancer, the enhancer on the late side of the origin of replication of polyomavirus, and adenovirus enhancers. The enhancer can be spliced into the vector at the 5' or 3' position of the anti-CD79b antibody coding sequence, but is preferably located at the 5' position of the promoter.

Expression vectors for use in eukaryotic host cells (yeast, fungi, insect, plant, animal, human or nucleated cells from other multicellular organisms) will also contain sequences necessary for termination of transcription and for stabilization of mRNA. Such sequences are typically obtained from the 5' end and the occasional 3' end of the eukaryotic or viral DNA or cDNA untranslated region. These regions comprise nucleotide segments transcribed into polyadenylated fragments in the untranslated portion of the mRNA encoding the anti-CD79b antibody. One useful transcription termination member is the bovine growth hormone polyadenylation region.

Vectors containing the nucleic acid sequences described herein can be transferred into a host cell using methods well known in the art. Techniques suitable for transferring nucleic acids into host cells in vitro include the use of liposomes, electroporation, microinjection, cell fusion, DEAE-dextran, calcium phosphate precipitation, and the like.

The host cell can be a prokaryotic cell and a eukaryotic cell. Suitable prokaryotes include, but are not limited to, archaea and eubacteria, such as Gram-negative or Gram-positive organisms, such as Enterobacteriaceae, such as *E. coli*. Other suitable prokaryotic host cells include *Enterobacter, Erwinia, Klebsiella, Proteus, Salmonella* such as *Salmonella typhimurium, Serratia* such as *Serratia marces-* cans, *Shigella*, and *Bacillus* such as *B. subtilis* and *Bacillus licheniformis*, *Pseudomonas* such as *P. aeruginosa*, *Rhizobia*, *Vitreoscilla Paracoccus* and *Streptomyces*.

Full length antibodies, antibody fragments, and antibody fusion proteins can be prepared in bacteria, particularly when glycosylation and Fc effector functions are not required, such as when a therapeutic antibody is conjugated to a cytotoxic agent (e.g., a toxin) and the immunoconjugate itself shows the efficacy of tumor cell destruction. Full length antibodies have a longer half-life in the circulation. Preparation in *E. coli* is faster and more economical. For the expression of antibody fragments and polypeptides in bacteria, see, for example, U.S. Pat. Nos. 5,648,237, 5,789,199, and 5,840,523, which describe translation initiation regions (TIR) and signal sequences for optimizing expression and secretion. After expression, the antibody is isolated from the *E. coli* cell paste in a soluble fraction and can be purified, for example, by protein A or G column based on its isotype. Final purification can be carried out using methods similar to those used for purifying antibodies expressed, for example, in CHO cells.

Eukaryotic microorganisms, such as filamentous fungi or yeast, are also suitable cloning or expression hosts for vectors encoding anti-CD79b antibodies. *Saccharomyces cerevisiae* is a commonly used lower eukaryotic host microorganism. Others include *Schizosaccharomyces cerevisiae, Kluyveromyces*, and the like.

Host cells suitable for expression of a glycosylated anti-CD79b antibody are derived from a multicellular organism. Examples of invertebrate cells include insect cells such as *Drosophila* S2 and Noctuidae Sf9, and cell cultures of plant cells such as cotton, corn, potato, soybean, *petunia*, tomato, tobacco. A number of baculovirus strains and variants and corresponding permissible insect host cells have been identified which are derived from hosts such as *Spodoptera frugiperda, Aedes aegypti, Aedes albopictus, Drosophila melanogaster* and *Bombyx mori*.

Examples of useful mammalian host cell lines are the monkey kidney CV1 line (COS-7, ATCC CRL1651) transformed with SV40, human embryonic kidney line (293 or 293 cells subcloned for growth in suspension culture), baby hamster kidney Cells (BHK, ATCCCCL10), Chinese hamster ovary cells/-DHFR (CHO), mouse sertoli cells (TM4), monkey kidney cells (CV1, ATCCCCL70), African green monkey kidney cells (VERO-76, ATCCRL-1587), human cervical cancer cells (HELA, ATCCCCL2), canine kidney cells (MDCK, ATCCCCL34), buffalorat hepatocytes (BRL3A, ATCCCRL1442), human lung cells (W138, ATCCCCL75), human hepatocytes (HepG2, HB8065), mouse breast tumor (MMT060562, ATCCCCL51), TRI cells, MRCS cells, FS4 cells, and human hepatosarcoma (HepG2).

Host cells for production of the anti-CD79b antibodies described herein can be cultured in a variety of media under culture conditions well known in the art.

Various forms of anti-CD79b antibodies can be recovered from the culture broth or from host cell lysates. If bound to membrane, it can be released from the membrane using a suitable detergent solution (e.g. Triton-X100) or by enzymatic lysis. The cells used in the expression of anti-CD79b antibodies can be disrupted by a variety of physical or chemical means, such as freeze-thaw cycles, sonication, mechanical disruption or lysing agents.

The antibody composition prepared from the cells can be purified using, for example, hydroxyapatite chromatography, gel electrophoresis, dialysis, and affinity chromatography. A preferred purification technique is affinity chromatography. Depending on the antibody to be recovered, other protein purification techniques can also be used, such as fractionation on an ion exchange column, ethanol precipitation, reverse phase HPLC, chromatography on silica, chromatography on heparin SEPHAROSE', chromatography on anion or cation exchange resin (for example polyaspartic acid column), chromatographic focusing, SDS-PAGE, and ammonium sulfate precipitation.

In another aspect, provided herein are immunoconjugates or antibody-drug conjugates (ADCs) comprising an antibody conjugated to a cytotoxic agent, and methods of use and preparation thereof. Cytotoxic agents suitable for use in the present invention may be drugs (e.g., chemotherapeutic drugs), growth inhibitors, toxins (e.g., enzymatically active toxins or fragments thereof of bacterial, fungal, plant or animal origin) or radioisotopes (i.e., radioconjugates). Typically, the immunoconjugate comprises any of the above anti-CD79b antibodies covalently linked to a cytotoxic or detectable agent.

As used herein, "drug" refers to any compound having desirable biological activity. Desirable biological activities include diagnosing, curing, alleviating, treating, preventing diseases in human or other animals. Thus, the term "drug" refers to compounds that are recognized by official national pharmacopoeia, as well as, for example, the US Official Homeopathic Pharmacopoeia, the official National Formulary, or any of its supplements. Typical drugs are listed in the physician's desk medication reference (PDR) and the US Food and Drug Administration (FDA) Orange Book. As new drugs continue to be discovered and developed, these drugs should also be included in the drug-conjugated prodrugs described herein. Preferably, the drug has a reactive functional group so that it can be used to prepare a conjugate as described herein.

Exemplary drugs suitable for use herein include, but are not limited to, cytotoxic drugs for cancer treatment; proteins or polypeptides having desired biological activities, such as toxins, such as acacia toxin, ricin A, *pseudomonas* exotoxin and diphtheria toxin. Other suitable proteins include tumor necrosis factor, alpha-interferon, beta-interferon, neurogenic growth factor, platelet-derived growth factor, tissue-type plasminogen growth factor, and biological response modulating agents, such as lymphokines, interleukin-1 (IL-1), interleukin-2 (IL-2), interleukin-6 (IL-6), granulocyte macrophage colony-stimulating factor (GM-CSF), granulocytes colony stimulating factor or other growth factors.

Exemplary drugs include: maytansine; maytansinoid; auristatin drugs (such as monomethyl auristatin E (MMAE) and monomethyl auristatin F (MMAF)); calicheamicins (such as calicheamicin); doxorubicins (such as doxorubicin); benzodipyrrole antibiotics (such as duocarmycins, CC-1065, etc.) and other cyclopropylpyrrole-4-one (CPI) derivatives, such as a cyclopropylbenzoindole-4-one analog, such as:

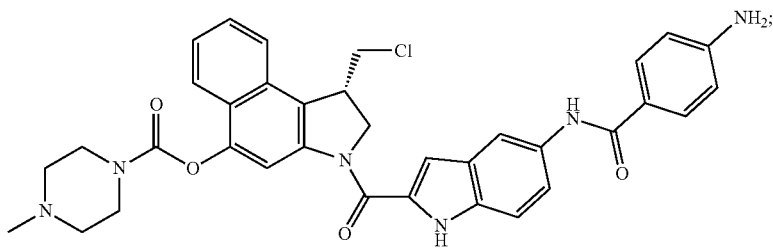 [SMILES: CN1CCN(C(=O)Oc2cc3c(c4ccccc24)[C@H](CCl)CN3C(=O)c2cc3cc(NC(=O)c4ccc(N)cc4)ccc3[nH]2)CC1]

and pyrrolobenzodiazepines (PBDs) or PBD dimers, such as:

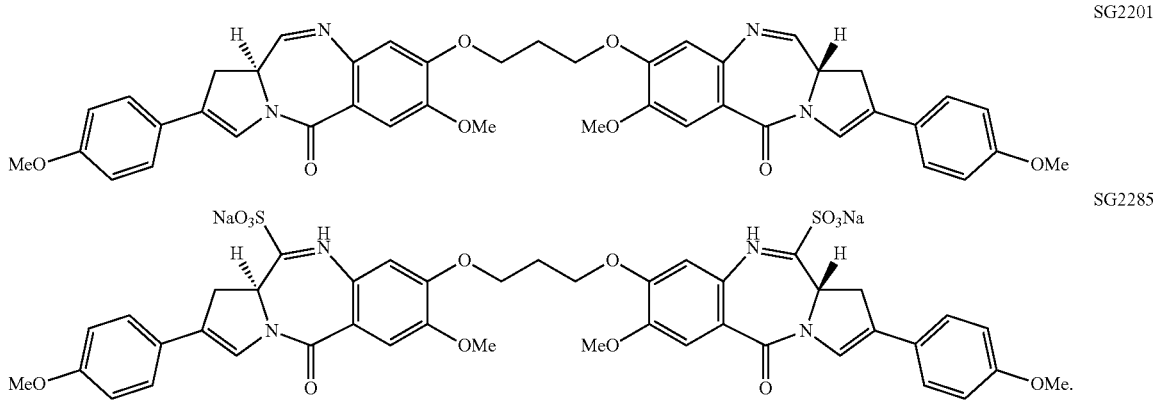

The antibody can be coupled to the drug either directly or via a linker. Linkers can be divided into two classes: non-cleavable linkers and cleavable linkers. For an antibody-drug conjugate comprising a non-cleavable linker, the drug release mechanism is: after the conjugate binds to the antigen and is internalized by the cell, the antibody is hydrolyzed in the lysosome, and the active molecule composed of small molecule drug, linker and amino acid residue of the antibody is released. The resulting change in the molecular structure of the drug does not reduce its cytotoxicity, but since the active molecule is charged (amino acid residues), it cannot infiltrate into adjacent cells. Therefore, such active drugs cannot kill adjacent tumor cells that do not express target antigen (antigen-negative cells) (bystander effect) (Ducry et al., 2010, Bioconjugate Chem. 21: 5-13). A cleavable linker can cleave within the target cell and release the active drug. Cleavable linkers can be divided into two main classes: chemically labile linkers and enzyme labile linkers. Chemically labile linkers can selectively cleave due to differences in plasma and cytoplasmic properties. Such properties include pH, glutathione concentration, and the like. pH-sensitive linkers, often referred to as acid-cleavable linkers, are relatively stable in the neutral environment of blood (pH 7.3-7.5), but will be hydrolyzed in weakly acidic endosomes (pH 5.0-6.5)) and lysosomes (pH 4.5-5.0). For glutathione-sensitive linkers, it is also called disulfide linker. Drug release is based on the difference between the high concentration (in millimolar range) of intracellular glutathione and the relatively low concentration of glutathione (in micromolar range) in the blood. This is especially true for tumor cells, wherein low oxygen levels result in enhanced reductase activity, thus resulting in higher glutathione concentrations. Disulfide bonds are thermodynamically stable and therefore have better stability in plasma. Enzyme-labile linkers, such as peptide linkers, provide better control of drug release. Peptide linkers can be efficiently cleaved by proteases such as cathepsin B or plasmin (an increase in the amount of such enzymes in some tumor tissues) in lysosome. This peptide linkage is believed to be very stable in the plasma circulation because the extracellular pH and serum protease inhibitors cause proteases generally inactive. In view of the high plasma stability and good intracellular cleavage selectivity and effectiveness, enzyme-labile linkers are widely used as cleavable linkers for antibody-drug conjugates. Typical enzyme labile linkers include Val-Cit (vc), Phe-Lys, and the like. Self-immolative linkers are typically integrated between the cleavable linker and the active drug, or are themselves part of a cleavable linker. The acting mechanism of the self-immolative linker is that when the cleavable linker is cleaved under suitable conditions, the suicide linker can spontaneously rearrange the structure and release the active drug linked thereto. Common self-immolative linkers include p-aminobenzyl alcohols (PAB) and beta-glucuronides.

A linker can comprise one or more linker members. For example, in certain embodiments, the structure of the linker may be V-L, wherein the V member may or may not be present, as described below for the tridentate linker member or the tetramaleimide linker member; L member may be a non-cleavable linker and a cleavable linker as described above, such as an acid labile linker (e.g., hydrazine), a protease sensitive (e.g., peptidase sensitive) linker, a photolabile linker, a dimethyl linker, or disulfide-containing linkers and the like. Exemplary linker members include 6-maleimidocaproyl, maleimidopropionylproline-citrulline, alanine-phenylalanine, p-aminobenzyloxycarbonyl, N-succinimidyl 4-(2-pyridylthio)pentanoate, N-succinimidyl 4-(N-maleimidomethyl)cyclohexane-1 carboxylate and N-succinimidyl (4-iodo-acetyl) aminobenzoate. Other exemplary linker members can further be linkers comprising an amino acid unit to allow protease cleavage, thereby facilitating the release of drug from the immunoconjugate after exposure to intracellular protease, such as a lysosomal enzyme. Exemplary amino acid units include, but are not limited to, dipeptides, tripeptides, tetrapeptides, and pentapeptides. Exemplary dipeptides include: valine-citrulline; alanine-phenylalanine; phenylalanine-lysine; or N-methyl-valine-citrulline. Exemplary tripeptides include: glycine-valine-citrulline and glycine-glycine-glycine.

An exemplary tridentate (or bismaleimide type) linker member can have the following structure:

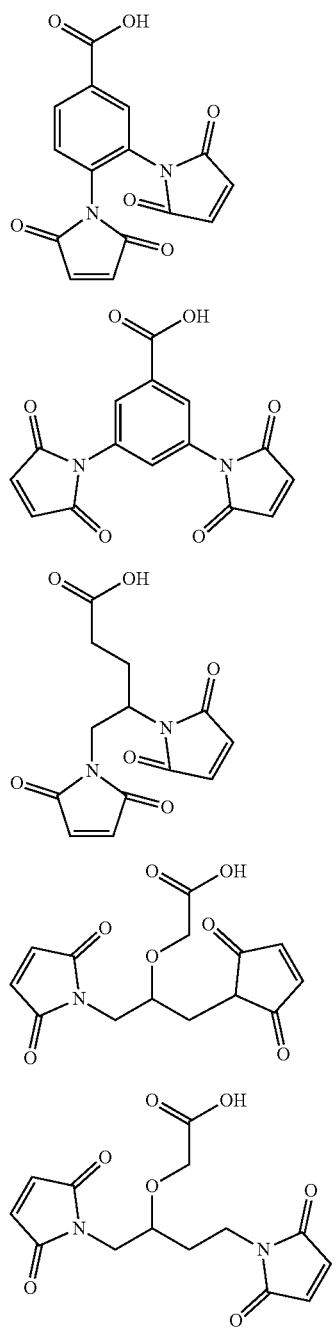

-continued

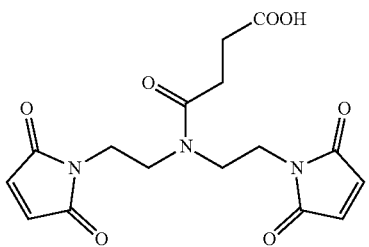

An exemplary tetramaleimide type linker member can have the following structure:

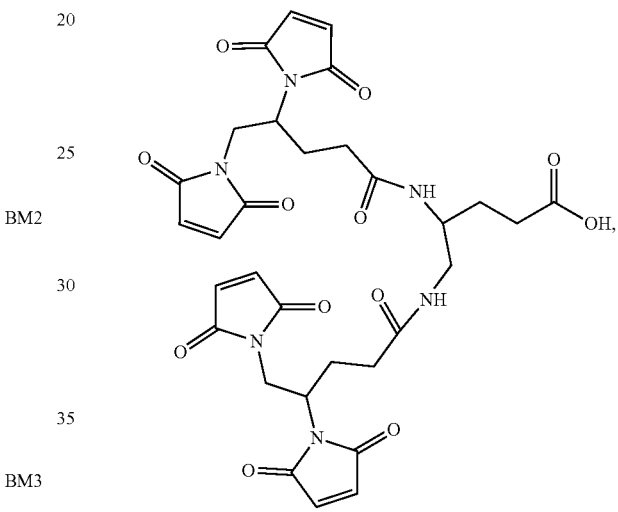

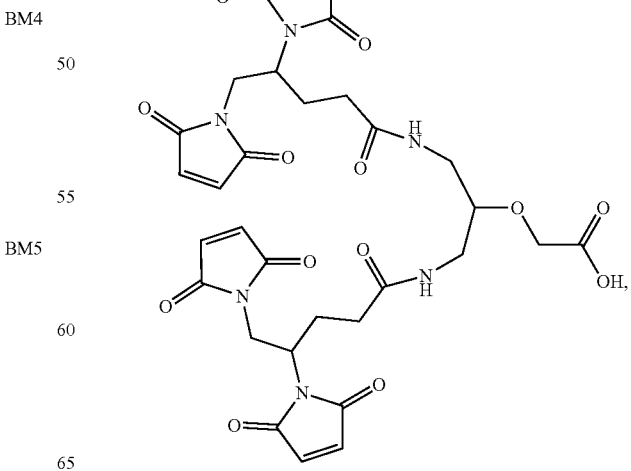

TM3
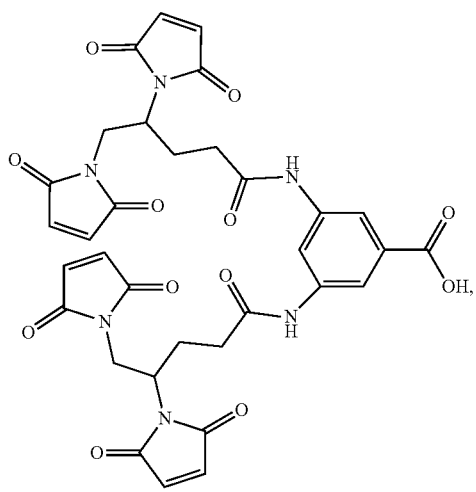
TM6
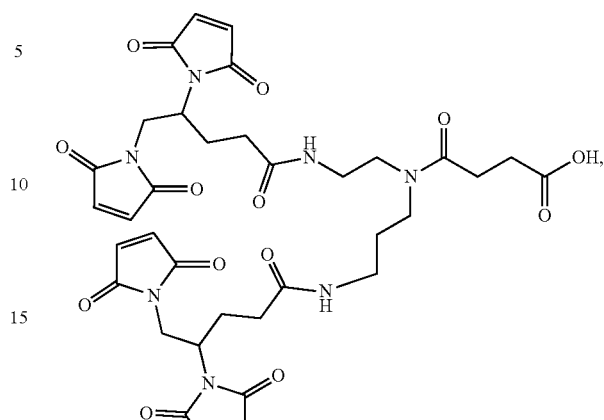
TM4
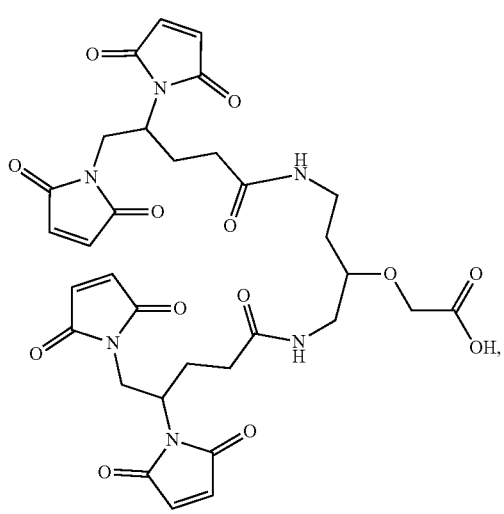
TM7
TM5
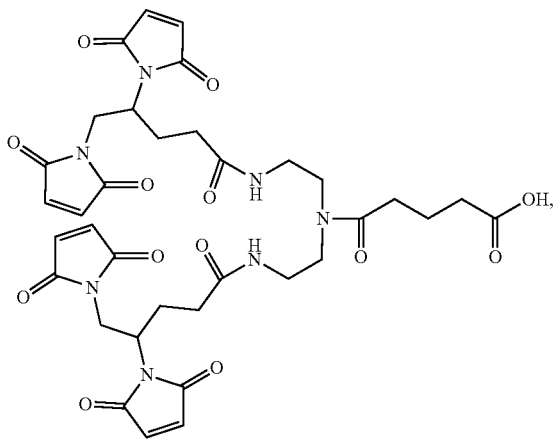
TM8
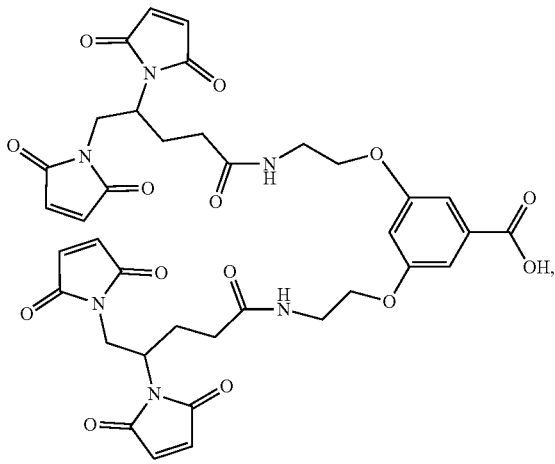

TM9
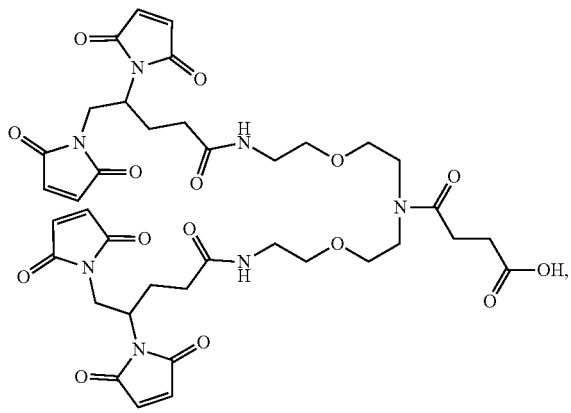
TM10
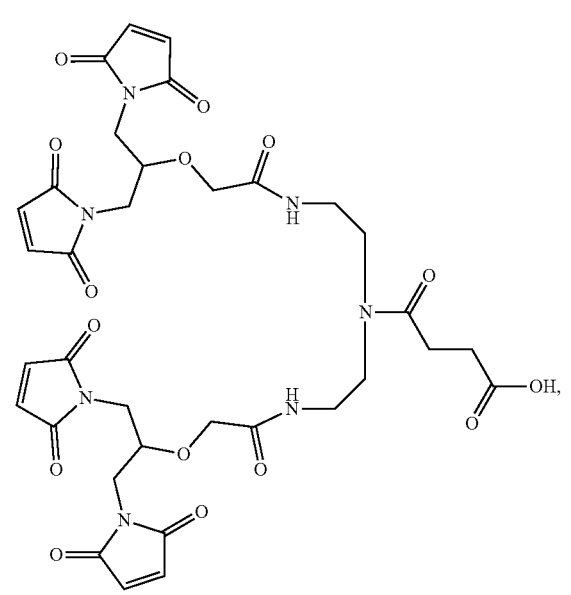
TM11
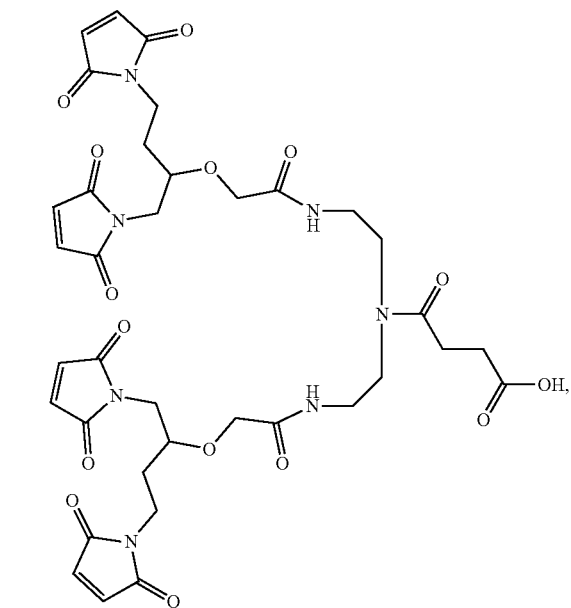
TM12
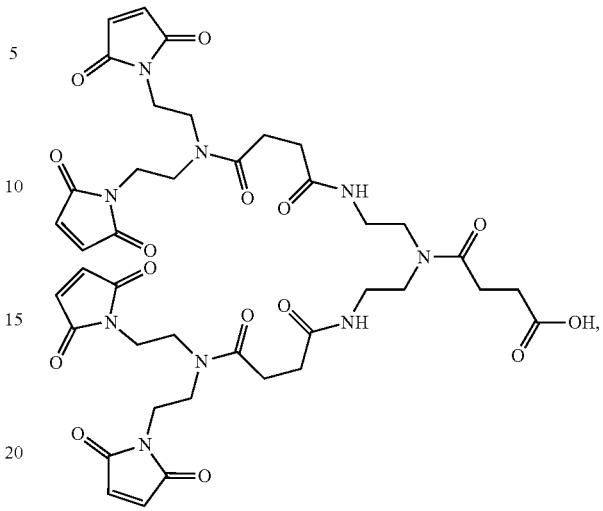
TM13
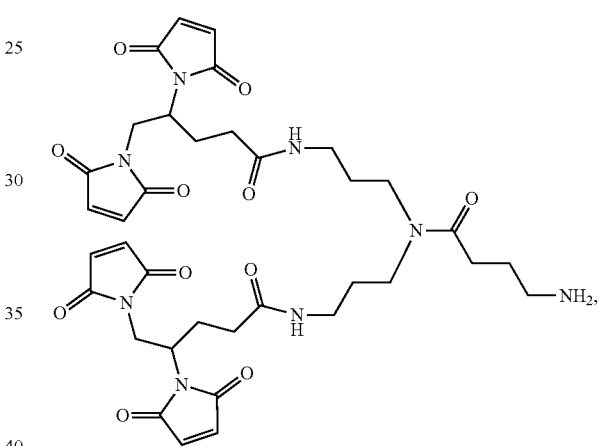
TM14
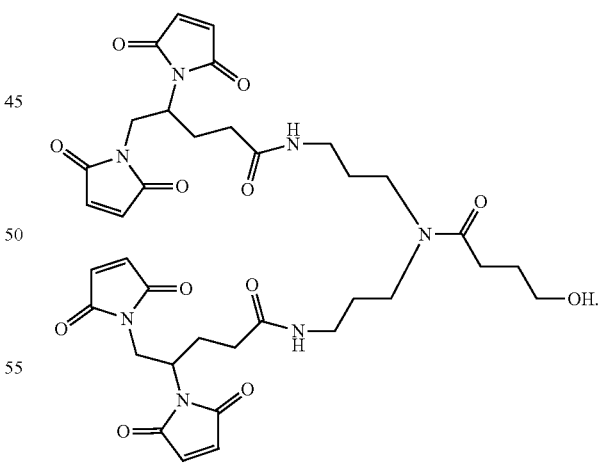
Other examples of suitable linkers, drugs or linker-drugs can be found in CN 103933575A and CN 107652219 A, including but not limited to the linker-drug as set forth in antibody-drug conjugates H-1-vcMMAE, H-1-MMAF, H-3-vcMMAE, H-3-MMAF, H-4-vcMMAE, H-4-MMAF disclosed in CN 103933575 A, and those disclosed in CN 107652219 A, numbered from 1-vcMMAE to 12-vcMMAE.

The entire contents of both applications are incorporated herein by reference. Thus, in certain embodiments, an antibody-drug conjugate herein may have the following structure:

$$A\text{-}(V\text{-}L\text{-}D)_n$$

wherein, A is an antibody disclosed herein; V-L is a linker; V may or may not be present, and may be any of the tridentate linker members or the tetramaleimide linker member as described above, and L is a cleavage linker or a non-cleavable linker, at least one of V and L is present; D is a cytotoxic agent of interest; n is an integer from 1 to 4.

In certain embodiments, L is a linker comprising an amino acid unit as previously described to allow protease cleavage.

Examples of exemplary antibody-drug conjugates herein can be found in the examples of the present application, including but not limited to AS11259-ADC-001, AS11259-ADC-002, AS11259-ADC-003, AS11259-ADC-004, AS11259-ADC-005, AS11259-ADC-006, AS11259-ADC-007, AS11259-ADC-008, AS11259-ADC-010, AS11259-ADC-011, and AS11250-ADC-0012.

In certain embodiments, the immunoconjugate can comprise a highly radioactive atom. A variety of radioisotopes are available for the production of radioconjugated antibodies. Examples include the radioisotopes of $At^{211}$, $I^{131}$, $I^{125}$, $Y^{90}$, $Re^{186}$, $Re^{188}$, $Sm^{153}$, $Bi^{212}$, $P^{332}$, $Pb^{212}$, and Lu. When the immunoconjugate is used for detection, it may contain a radioactive atom for scintigraphy studies, such as $Tc^{99m}$ or $I^{123}$, or a spin label for nuclear magnetic resonance (NMR) imaging (also known as magnetic resonance imaging (MRI)), such as iodine-123, iodine-131, indium-111, fluorine-19, carbon-13, nitrogen-15, oxygen-17, cesium, manganese or iron.

Radioactivity or other labels can be incorporated into the immunoconjugate in a known manner. For example, peptides can be biologically synthesized or synthesized by chemical amino acid synthesis using suitable amino acid precursors involving, for example, fluorine-19 in place of hydrogen. Labels may be attached via cysteine residues in the peptide, such as $Tc^{99m}$ or $I^{123}$, $Re^{186}$, $Re^{188}$ and $In^{111}$. The Y-90 can be attached via a lysine residue.

The ADCs herein can be prepared by several routes using organic chemical reactions, conditions, and reagents known to those skilled in the art, including: (1) the reaction of nucleophilic group of the antibody with a bivalent linker reagent via a covalent bond, forming an antibody-linker via covalent bond, prior to reacting with the drug; and (2) the reaction of nucleophilic group of the drug moiety with the divalent linker reagent to form a drug-linker via a covalent bond, followed by reacting with the nucleophilic group of the antibody.

The antibodies, functional fragments thereof or antibody-drug conjugates thereof can be administered by any route appropriate to the condition to be treated, including oral, parenteral, subcutaneous, intramuscular, intravenous, intradermal, intrathecal and epidural.

For the prevention or treatment of a disease, the appropriate dose of the antibody, the functional fragment or antibody-drug conjugate thereof described herein (when used alone or in combination with one or more of other agents such as chemotherapeutic drugs) will depend on the type of disease, the type of antibody, its functional fragment or antibody-drug conjugate, the severity and progression of the disease, the administration of the antibody, its functional fragment or antibody-drug conjugate for prophylactic or therapeutic purposes, previous treatment, the patient's clinical history and response to antibodies, functional fragments or antibody-drug conjugates thereof, and the judgment of the attending physician. Suitably, the antibody, its functional fragment or antibody-drug conjugate is administered to the patient, either once or through a series of treatments. Depending on the type and severity of the disease, the initial candidate dose administered to the patient may be from about 1 µg/kg to 100 mg/kg (e.g., 0.1 mg/kg to 20 mg/kg) of the antibody, the functional fragment or antibody-drug conjugate thereof, for example by one or more separate administrations or by continuous infusion. Typical daily doses may range from about 1 µg/kg to 100 mg/kg or more, depending on the factors described above. For repeated administrations that last for several days or longer, depending on the condition, treatment is usually continued until the disease symptoms are desirably inhibited. Exemplary dosages of antibodies, functional fragments thereof or antibody-drug conjugates can range from about 0.05 mg/kg to about 10 mg/kg. As such, one or more doses of antibody, functional fragment thereof or antibody-drug conjugate can be administered to the patient at about 0.5 mg/kg, 2.0 mg/kg, 4.0 mg/kg or 10 mg/kg (or any combination thereof). These doses can be administered intermittently, for example weekly or every three weeks (e.g., such that the patient receives from about 2 to about 20 doses, such as about 6 doses of antibody or immunoconjugate). A higher initial loading dose can be administered followed by one or more lower doses. An exemplary dosing regimen comprises administering an initial loading dose of about 4 mg/kg of antibody, followed by a maintenance dose of about 2 mg/kg per week. However, other dosage regimens may also be useful. The course of this therapy is easily monitored by conventional techniques and assays.

In addition to administering antibody proteins to a patient, the present application contemplates administration of antibodies by gene therapy. The use of gene therapy to generate intracellular antibodies can be seen in, for example, WO 96/07321. There are two primary methods for allowing nucleic acids (optionally comprised in a vector) to enter the cells of a patient, i.e., in vivo and ex vivo. For in vivo delivery, the nucleic acid is typically injected directly into the patient at the site where the antibody is desired. For ex vivo treatment, the patient's cells are harvested, nucleic acids are introduced into the isolated cells, and the modified cells are either administered directly to the patient or, for example, inserted into a porous membrane and implanted into the patient (see, for example, U.S. Pat. Nos. 4,892,538 and 5,283,187). A variety of techniques are available for introducing nucleic acids into living cells. These techniques vary depending on whether the nucleic acid is transferred to the in vitro cultured cells or in vivo cells of the intended host. Techniques suitable for transferring nucleic acids into mammalian cells in vitro include the use of liposomes, electroporation, microinjection, cell fusion, DEAE-dextran, calcium phosphate precipitation, and the like. A vector commonly used for ex vivo delivery of genes is a retrovirus.

Currently preferred in vivo nucleic acid transfer techniques include the transfection by the use of viral vectors (such as adenovirus, herpes simplex virus type I or adeno-associated virus) and lipid-based systems (lipids useful for lipid-mediated gene transfer are for example DOTMA, DOPE and DC-Chol).

Also provided herein are pharmaceutical compositions comprising at least one anti-CD79b antibody described herein and/or at least one immunoconjugate thereof and/or at least one anti-CD79b antibody-drug conjugate described herein. In certain embodiments, a pharmaceutical composition comprises: (1) an anti-CD79b antibody herein and/or an immunoconjugate thereof, and (2) a pharmaceutically acceptable carrier. In certain embodiments, the pharmaceutical composition comprises: (1) an anti-CD79b antibody herein and/or an immunoconjugate thereof, and optionally (2) at least one known therapeutic formulation, such as those therapeutic formulations that can be used in the treatment of CD79b-mediated disease.

A pharmaceutical composition comprising an anti-CD79b antibody or an anti-CD79b antibody-drug conjugate, as used herein, can be prepared into lyophilized dosage form or an aqueous solution for storage by mixing the antibody or antibody-drug conjugate of desired purity with an optional pharmaceutically acceptable carrier, excipient or stabilizer. The acceptable carriers, excipients, or stabilizers are non-toxic to the recipient at the dosages and concentrations employed, and include buffers such as acetate, Tris, phosphate, citrate, and other organic acids; antioxidants, including ascorbic acid and methionine; preservatives (such as octadecyldimethylbenzylammonium chloride; chlorhexidine ammonium; benzalkonium chloride, benzethonium chloride; phenol, butanol or benzyl alcohol); Hydrocarbyl paraben, such as methylparaben or propylparaben; catechol; resorcinol; cyclohexanol; 3-pentanol; and m-cresol); lower molecular weight (less than about 10 residues) polypeptide; protein, such as serum protein, gelatin or immunoglobulin; hydrophilic polymers, such as polyvinylpyrrolidone; amino acids such as glycine, glutamine, asparagine, histidine, arginine or lysine; monosaccharides, disaccharides and other carbohydrates, including glucose, mannose or dextrin; chelating agents such as EDTA; tonicity modifiers such as trehalose and sodium chloride; saccharides, such as sucrose, mannitol, trehalose or sorbitol; surfactants such as polysorbates; salt-forming counterions such as sodium; metal complexes (e.g. Zn-protein complexes); and/or nonionic surfactants such as TWEE®, PLURONICS® or polyethylene glycols (PEG). Pharmaceutical formulations for in vivo administration are generally sterile. This is easily accomplished by filtration through a sterile filter.

The anti-CD79b antibodies herein can be used to treat the tumor expressing CD79b in a mammal or alleviate one or more symptoms thereof. Such tumors include, but are not limited to, cancers of the hematopoietic system or blood-related cancers, such as lymphomas, leukemias, myeloma or lymphoid malignancies, as well as cancers of the spleen and cancers of the lymph nodes. Tumors expressing CD79b include particularly B cell-associated cancers, specific examples of which include, for example, advanced, intermediate, and lower-grade lymphomas (including B-cell lymphomas such as, for example, mucosa-associated lymphoid tissue B-cell lymphomas and non-Hodgkin's lymphomas, mantle cell lymphoma, Burkitt's lymphoma, small lymphocytic lymphoma, marginal zone lymphoma, diffuse large B-cell lymphoma, follicular lymphoma and Hodgkin's lymphoma and T-cell lymphoma) and leukemia (including secondary leukemia, chronic lymphocytic leukemia such as B cell leukemia ($CD5^+$ B lymphocytes), myeloid leukemia such as acute myeloid leukemia, chronic myeloid leukemia, lymphoid leukemia such as acute lymphocytic leukemia and myelodysplasia). Cancer encompasses any of the aforementioned metastatic cancers. The antibody is capable of binding to at least a portion of tumor cells expressing a CD79b polypeptide in a mammal. In a preferred embodiment, the antibody effectively disrupts or kills tumor cells expressing CD79b or inhibits the growth of such tumor cells when bound to the CD79b polypeptide on the cell in vitro or in vivo. Such antibodies include naked anti-CD79b antibodies (not coupled to any agent). Naked antibodies with cytotoxic or cytostatic properties can further cooperate with cytotoxic agents, making them more effective at destroying tumor cells. The anti-CD79b antibody can be rendered cytotoxic by, for example, coupling the antibody to a cytotoxic agent to form an immunoconjugate as described herein.

Also provided herein are articles comprising a substance useful for treating, preventing, and/or diagnosing tumor that expresses CD79b. The article comprises a container and a label or package insert on or associated with the container. Suitable containers include, for example, bottles, vials, syringes, and the like. The container can be made from a variety of materials such as glass or plastic. The container contains a composition effective to treat, prevent and/or diagnose a tumor condition, and may have a sterile access port (e.g., the container may be an intravenous solution bag or vial having a stopper pierceable by a hypodermic needle). At least one active agent in the composition is an anti-CD79b antibody herein. The label or package insert indicates that the composition is used to treat, prevent, and/or diagnose a tumor. The label or package insert further includes instructions for administering the antibody composition to a patient with a tumor, particularly a cancer. Additionally, the article of manufacture may include a second container containing a pharmaceutically acceptable buffer such as bacteriostatic water for injection (BWFI), phosphate buffered saline, Ringer's solution, and dextrose solution. It may also include other materials required by commercial and user standpoint, including other buffers, diluents, filters, needles, and syringes.

Kits are also provided that can be used for a variety of purposes, such as cytotoxic assays for cells expressing CD79b, for purifying or immunoprecipitating CD79b polypeptides from cells. For isolation and purification of CD79b, the kit can comprise an anti-CD79b antibody conjugated to beads (e.g., sepharose beads). Kits comprising antibodies can be provided for in vitro detection and quantification of CD79b polypeptides, such as in ELISA or Western blots. As the same for the article, the kit includes a container and a label or package insert on or associated with the container. The container contains a composition comprising at least one of the anti-CD79b antibodies herein. Additional containers can be included in which are, for example, diluents and buffers, control antibodies. The label or package insert can provide a description of the composition as well as instructions for intended in vitro or test use.

EXAMPLES

The invention is further illustrated below in conjunction with specific embodiments. It is to be understood that the examples are not intended to limit the scope of the invention. The experimental methods in the following examples which do not specify the specific conditions are usually carried out according to conventional conditions or according to the conditions recommended by the manufacturer. All reactions were carried out under nitrogen (except for hydrogenation reaction).

Unless otherwise defined, all professional and scientific terms used herein have the same meaning as those familiar by the skilled in the art. In addition, any methods and materials similar or equivalent to those described may be employed in the methods of the invention. The methods and materials described herein are for illustrative purposes only.

Abbreviations

Ab antibody
ACN acetonitrile

ADC antibody drug conjugate
BOC(Boc) tert-butoxycarbonyl
DCM dichloromethane
DIPEA diisopropylethylamine
DMF N,N-dimethylformamide
ELISA enzyme-linked immunosorbent assay
EtOAc ethyl acetate
Eq (eq) equivalent
g gram
HATU O-(7-azabenzotriazol-1-yl)-N,N,N,N-tetramethylurea hexafluorophosphate
HOSu N-hydroxysuccinimide
HIC hydrophobic interaction chromatography
HPLC high performance liquid chromatography
LC-MS liquid chromatography-mass spectrometry
mAb monoclonal antibody
min minute
mL mL
MS mass spectrometry
nm nanometer
μL microliter
PE petroleum ether
rt room temperature
Rt retention time
SDS-PAGE polyacrylamide gel electrophoresis
SEC size exclusion chromatography
TEA triethylamine
TFA trifluoroacetic acid
THF tetrahydrofuran Unless otherwise stated, all anhydrous reagents were purchased directly from the supplier and stored under nitrogen. All other reagents and solvents purchased were of high purity and were not further purified prior to use.

Nuclear magnetic resonance spectra were acquired on a Bruker Avance III 500 M NMR spectrometer. The chemical shift (δ) unit is ppm and tetramethylsilane is used as a reference system (chemical shift is 0).

In the liquid chromatography-mass spectrometry method, low-resolution mass spectrometry data was acquired on an Agilent 6110 (acid method) or 6120B (base method) mass spectrometer interfaced with an HP Agilent 1200 high performance liquid chromatography.

Method 1: Acidic high performance liquid chromatography was performed on a Waters Sunfire C18 reversed phase column (4.60×50 mm, 3.5 μm) with an eluting gradient of 5%-95% B phase (acetonitrile, containing 0.01% TFA) in phase A (aqueous phase, containing 0.01% TFA) in 1.4 min, with the flow rate at 2.0 mL/min, and the column temperature is 50° C.;

Method 2: Acidic high performance liquid chromatography was performed on a Poroshell 120 EC-C18 reverse phase column (4.60×30 mm, 2.7 μm). The eluting gradient was 5%-95% B phase (acetonitrile, containing 0.01% TFA) in phase A (aqueous phase, containing 0.01% TFA) in 2 min, with the flow rate at 1.5 mL/min, and the column temperature is 50° C.;

Method 3: Basic high performance liquid chromatography was performed on a Waters Xbridge C18 reverse phase column (4.60×50 mm, 3.5 μm) with an eluting gradient of 5%-95% B phase (acetonitrile) in phase A (aqueous phase, containing 10 mM ammonium bicarbonate) in 1.5 min, with the flow rate at 2.0 mL/min, and the column temperature is 40° C.

Preparation was performed by reverse phase-high performance liquid chromatography (prep-RP-HPLC) on a Gilson instrument using a Waters Sunfire C18 reversed phase column (250×19 mm, 10 μm).

Method 4: Preparation by acidic method. Mobile phase: A: aqueous phase containing 0.1% TFA; B: ACN. Flow rate: 20 mL/min.

Method 5: Preparation by basic method. Mobile phase: A: aqueous phase containing 10 mM ammonium bicarbonate; B: ACN. Flow rate: 20 mL/min.

Commercially available reagents mentioned in the example were used according to the manufacturer's instructions unless otherwise stated.

1. Antigen-Antibody Binding Assay (ELISA)

In the examples, the affinity of the anti-CD79b antibody (including mouse serum, hybridoma supernatant or recombinantly expressed monoclonal antibody, etc.) to the CD79b antigen was examined by enzyme-linked immunosorbent assay.

The experimental procedure was as follows: 96-well plates (Corning, CAT #9018) were coated with 100 μL/well of antigen (human CD79b-ECD, novoprotein, CA29) at 1 μg/mL in PBS (10 mM phosphate, 138 mM NaCl, pH 7.2) at 4° C. overnight, and then blocked with 250 ul/well of blocking solution (PBS+1% BSA (Sangon, CAT #A0332)) for one to three hours at 25° C. Plates were washed 3 times with a washing solution (PBS+0.05% Tween-20 (Sangon, CAT #TB0560)), and then incubated with 100 μL of anti-CD79b antibody in serial dilutions in blocking solution in duplicate wells at 25° C. for 2 h. Plates were washed 3 times with washing solution and then incubated with 100 μL of 1:10,000 the secondary antibody (anti-mouse IgG (Fc)-HRP, Sigma, CAT #A00168 or anti-human IgG F(ab')2-HRP, Sigma, CAT #A0293) at 25° C. for 1 h. Plates were washed 3 times with washing solution, and then 100 μL of TMB (Sangon, CAT #TB0954) was added to each well and incubated at 25° C. until color developed (approximately 15 min). Reactions were stopped by addition of 100 μl/well stop solution (1N H2SO4). OD450/630 nm was read on plate reader in 10 minutes.

2. FACS Detection for the Binding of Antibodies to Cell Surface CD79b

In the example, flow cytometry (FACS) was used to detect the ability of anti-CD79b antibodies (including mouse serum, hybridoma antibodies, etc.) to bind to the native CD79b extracellular domain on the surface of cancer cells in vitro.

Cancer cell beads positively or negatively expressing CD79b were purchased from DSMZ or ATCC, and cell surface CD79b was quantified using Cell Membrane Surface Receptor Quantitation Kit QIFIKIT (DAKO, K0078). The results are as follows:

| Cell lines | Cell type | Source | Numbering | CD79b receptor number/cell |
|---|---|---|---|---|
| DOHH-2 | B-cell lymphoma | DSMZ | ACC 47 | 142208 |
| GRANTA-519 | B-cell lymphoma | DSMZ | ACC 342 | 14708 |
| BJAB | African Lymphoma | DSMZ | ACC 757 | 495110 |
| U-698-M | B-cell lymphoma | DSMZ | ACC 4 | 26226 |
| WSU-DLCL2 | B-cell lymphoma | DSMZ | ACC 575 | 1664 |
| Ramos | B lymphocyte | ATCC | CRL-1596 ™ | 12603 |
| SU-DHL-4 | B lymphocyte | ATCC | CRL-2957 ™ | 259648 |
| Jurkat | T lymphocyte | ATCC | TIB-152 ™ | 0 |
| Raji | B lymphocyte | ATCC | CCL-86 ™ | 0 |

Detection and screening of immunized mice and hybridoma supernatants were performed using SU-DHL-4 cell line. Specifically, the SU-DHL-4 cells in the logarithmic growth phase were collected, washed with PBS, and then dispensed into 1.5 ml EP tubes, at about 100,000 cells per tube. Diluted mouse serum or hybridoma supernatant was added at 100 μl/tube and incubated for 1 hour at 4° C. After washing twice with PBS-2% BSA, Alexa Fluor 488 goat anti-mouse IgG (H+L) formulated in PBS-2% BSA 1:400 (Molecular probes, Cat #A11001) was added at 100 μl/tube, and then the solution was incubated at 4° C. for 45 minutes in the dark. The cells were washed twice with PBS-2% BSA, and then resuspended in 500 μl PBS-2% BSA and analysed on flow cytometry Guava (Millipore, 8HT). The binding strength of the antibody to the cell surface CD79b receptor was determined based on the fluorescence intensity (MFI value).

3. Preparation of Drug Conjugates

In order to verify the efficacy of the anti-CD79b antibody, the antibodies were conjugated with different small molecule drugs using different linkers to prepare drug conjugates, and the specific coupling method is as follows:

Tris(2-carboxyethyl)phosphine hydrochloride (TCEP, 10 eq, stock solution at 10 mM) was added to the antibody solution (20 mM sodium dihydrogen phosphate-disodium hydrogen phosphate buffer, 150 mM sodium chloride, pH 7.2). The reaction solution was incubated for 2 hours in a 37° C. thermostat water bath. The reaction solution was cooled to about room temperature and replaced by ultrafiltration (Millipore Amicon® Ultra, 50000 MWCO) or gel filtration into buffer (100 mM potassium dihydrogen phosphate-dipotassium hydrogen phosphate, 100 mM sodium chloride, 1 mM ethylene triamine pentaacetic acid, pH 7.0-8.0) or buffer (20 mM citric acid-trisodium citrate, 50 mM sodium chloride, 1 mM diethylenetriaminepentaacetic acid, pH 6.0). Dimethyl sulfoxide and corresponding linker-drug compound (dimethyl sulfoxide stock solution, 3-10 equivalents relative to the antibody) were added, and the volume of dimethyl sulfoxide in the reaction solution was ensured to be about 10-15%. The coupling reaction was carried out at 10° C. for 0.5 hour.

An excess amount of cysteine solution was added to the reaction solution to quench the unreacted linker-drug compound, and the quenching reaction was carried out at 10° C. for 30 minutes. The reaction solution was first subjected to ultrafiltration (Millipore Amicon® Ultra, 50000 MWCO) or gel filtration to remove linker-drug-cysteine adduct and excess cysteine, and then the sample was buffer-exchanged into a storage buffer (20 mM sodium dihydrogen phosphate-disodium hydrogen phosphate buffer, 150 mM sodium chloride, pH 7.2), which was further sterilized through a 0.22 μm pore size filter device (Millex-GV Filter) to give anti-CD79b-ADC, stored at 4° C.

Antibodies prepared by the above methods for drug conjugates include rat anti-mouse HB58 antibody (ATCC® HB-58TM), anti-CD79b human-mouse chimeric antibody, and different variants after humanization, including other control antibodies mentioned herein.

4. Secondary ADC Assay for the Detection of the Proliferation Inhibitory Effect of Hybridoma Supernatant on Lymphoma Cell BJAB For antibodies that are of small amount or difficult to purify, there is not enough amount to complete the coupling experiment with the linker and the small molecule toxin. For this, the antibody is first bound to an antibody that has been conjugated to the linker and the small molecule of the toxin, and then co-incubated with the cancer cells, and the antibody drug conjugate bound thereto is brought into the cells to kill the cancer cells by endocytosis of the target antibody. The endocytic properties of such indirectly reactive antibodies and the proliferation inhibitory effect on cancer cells are referred to as secondary ADC experiments.

In order to carry out the secondary ADC experiment, the HB58 cell line (ATCC® HB-58TM) was purchased from ATCC. The cell line was a hybridoma cell obtained by fusing rat B cells with P3X63Ag8.653 myeloma cells. The secreted antibody can specifically binds to murine antibodies. Sufficient HB58 antibody was obtained by purification of HB58 cell line culture medium. Antibody drug conjugate HB58-ADC was prepared.

Human lymphoma cell BJAB was inoculated into 96-well cell culture plates (BD falcon, Cat #353072) at $1 \times 10^5$ cells/100 ul/well, and the medium was ATCC-modified RPMI1640 medium (Gibco, Cat #A10491)+10% Fetal bovine serum (FBS) (Gibco, Cat #10099141). Incubated one day in a 37° C. incubator (SANYO, MC0018AIC), and the hybridoma supernatant containing anti-CD79b antibody which had been premixed with HB58-ADC at a 1:1 concentration ratio and relevant control, were added at 100 ul/well the next day with three fold dilution, a total of 9 wells with gradient concentrations+1 control well. Incubation was carried out for three days in a 37° C. incubator. On the fifth day, Cell Counting Kit-8 (DOJINDO, CK04) was used for developing color. Cell proliferation was measured according to the kit instruction. The absorbance at 450/630 nm was read with a microplate reader (BioTek Synergy MX) to calculate the $IC_{50}$ and inhibition rate.

5. Surface Plasmon Resonance Method for Determination of Antibody Affinity

In the examples, surface plasmon resonance (SPR) was used to detect the binding ability of anti-CD79b antibodies (including human-mouse chimeric antibodies and humanized antibodies, etc.) to recombinant CD79b extracellular domain protein in vitro.

The assay was performed on a Biacore T200 (GE) machine, and the antibody to be tested was diluted to 10 ug/ml with HBS-EP (GE, BR100826) buffer according to the instruction of Amine-Coupling Kit (GE, BR-1000-50). The antibody to be tested was immobilized on a CM5 chip (GE, BR-1006-68) at a fixing time of 300 sec and a flow rate of 10 ul/min. Different concentrations (0.25 nm, 0.5 nm, 1 nm, 2 nm, 4 nm, 8 (×2) nm, 16 nm) of the recombinant CD79b extracellular domain protein diluted with HBS buffer gradient was subjected to capture reaction by Kinetics program, with the binding time of the antigen-antibody set to 300 seconds, dissociation time set to 900 seconds, flow rate of the antigenic protein to 30 ul/min. The dissociation curves were fitted to calculate the KD values of the different antibodies. The above experiments were all carried out at 25° C.

Example 1: Generation and Screening of Mouse Monoclonal Antibody Cell Lines Against Human CD79b The mouse-derived anti-human CD79b monoclonal cell lines was obtained by mice immunization, spleen cell fusion and hybridoma screening method, which was entrusted to Nanjing Jinsui Biotechnology Co., Ltd. to complete. The antigen used for immunization was recombinant human CD79b extracellular domain protein (Shanghai Novoprotein, Ltd., under product name of recombinant human CD79B, lot #CA29, the amino acid sequence shown as SEQ ID NO: 35), and four mice species (Balb/C, C3H, SJL, C57BL/6, respectively) were chosen to immunize, six mice of each species. The immunological adjuvant is a conventional Freund's adjuvant, and the dose of the primary immunization is 50 ug of antigen per mouse. The immunization was boosted at intervals of two weeks with the dose reduced to 25 ug. From the first booster immunization, the serum of the mice was collected 7 days after each booster immunization. The titer was determined by ELISA (see the first point in the "Materials and Methods" for the method). FACS detection was performed on the serum of mice collected 7 days after the second booster immunization (see the second point of the "Materials and Methods" section) to see if it can bind to CD79b on the surface of SU-DHL4 cell line which showed positive expression of CD79b. The binding titer of each mouse was simultaneously determined.

After two booster immunizations, according to the results of ELISA and FACS, the mice with the highest titer were selected for cell fusion (by electrofusion), and the fusion efficiency was about 3,000 spleen B cells fused into one hybridoma cell. All fused cells were plated into 96-well plates, with 40 plates per fusion. ELISA assay was performed one week later (see point 1 of the Materials and Methods section for the method). The supernatant of positive clones in ELISA assay was collected for FACS detection (see point 2 of the Materials and Methods section for methods). All the clones positive in FACS detection were subcloned. The supernatant in the well with monoclone after one subcloning was collected for secondary ADC detection (see point 3 of the Materials and Methods section). Clones that could inhibit the proliferation of BJAB cancer cells, which showed positive expression of CD79b, in a secondary ADC assay were subjected to continuous subcloning until a stable monoclonal cell line was formed.

In the present example, three effective fusions were performed. A total of 31 FACS positive clones were obtained after screening. Finally, 18 strains with the best proliferation inhibition effect (see Table 1 below) were selected for complete subcloning.

TABLE 1

| Clone number | IC$_{50}$ against BJAB(ng/ml) | EC$_{50}$ obtained by ELISA(ng/ml) |
| --- | --- | --- |
| 35B5 | 7.89 | 11.1 |
| 38E4 | 62.1 | 50.8 |
| 33H10 | 3.25 | 3.86 |
| 50B10 | 3.52 | 6.75 |
| 34B4 | 3.36 | 1.99 |
| 82F12 | 2.23 | 3.07 |
| 75G3 | 12.4 | 8.82 |
| 81C3 | 16.0 | 11.0 |
| 85B3 | 7.9 | 12.1 |
| 85B5 | 6.25 | 11.9 |
| 83A10 | 8.87 | 11.8 |
| 85G11 | 7.64 | 10.3 |
| 78B6 | 10.7 | 13.4 |
| 88B12 | 14.0 | 11.8 |
| 104E1 | 9.3 | 14.9 |
| 104A2 | 8.64 | 12.1 |
| 110A4 | 13.4 | 13.7 |
| 110D5 | 11.1 | 12.9 |

Example 2: Sequencing of Anti-CD79b Hybridoma Antibody and Construction of Recombinant Chimeric Antibody Hybridoma sequencing was done for the 18 monoclonal cell lines listed in Table 1 of Example 1, and then chimeric antibodies with a constant region of human IgG1 were recombinantly expressed and tested for their activity. In this example, the genes of the heavy and light chain variable regions of the antibody were amplified by reverse transcription PCR, ligated into a vector, and the monoclonal antibody light and heavy chain sequences were sequenced. Specifically, the total RNA of each monoclonal cell strain was first extracted using an RNA purification kit (Qiagen, Cat #74104). The cDNA single strand, the Oligo-dT primers cDNA, was then reverse transcribed using a cDNA synthesis kit (Invitrogen, Cat. No. 18080-051). Using this as a template, the antibody light and heavy chain variable region sequences were synthesized by PCR, and the PCR product was cloned into the TA vector pMD-18T, and then sequenced.

By analyzing the sequences of the CDR regions of the heavy and light chains, antibodies with potential sites for post-translational modification were excluded. Finally, six clones (35B5, 78B6, 85G11, 88B12, 104A2, and 104E1) were chosen for the recombinant expression of the antibody. First of all, the light and heavy chain sequences of the antibody were codon-optimized for whole gene synthesis. HindIII/NheI restriction sites were added at both ends of the heavy chain, and HindIII/BsiWI restriction sites were added at both ends of the light chain. The heavy/light chain variable region genes were ligated to the expression vector PTTS containing the human IgG1 constant region sequence or the K-chain constant region sequence via these two pairs of restriction sites to construct the expression vectors for the chimeric antibodies. Recombinant antibodies were expressed by transient expression in 293F cells.

Example 3: Cytotoxicity Analyses of Anti-CD79b Antibody-Drug Conjugates

Six recombinant chimeric antibodies (35B5, 78B6, 85G11, 88B12, 104A2, and 104E1) were conjugated to BMP-vcMMAE (linker-drug 1) separately to prepare antibody drug conjugates (ADCs). Proliferation inhibition assay were performed on seven CD79b positively expressing lymphoma cell lines BJAB, Ramos, DoHH2, SU-DHL-4, U-698-M, Granta-519, WSU-DLCL2 and two CD79b negatively expressing lymphoma cell lines Raji and Jurkat. The culture conditions of the cancer cells were all the same (see Section 3 of the Materials and Methods section). The cell plating density and initial concentration of ADC for different cancer cell lines are shown in Table 2 below.

TABLE 2

| Lymphoma strain | Plating number (cell/well) | ADC initial concentration(ng/ml) |
| --- | --- | --- |
| BJAB | 10000 | 400 |
| Ramos | 40000 | 400 |
| DoHH2 | 40000 | 400 |
| SU-DHL-4 | 30000 | 400 |
| U-698-M | 20000 | 1000 |
| Granta-519 | 50000 | 2000 |
| WSU-DLCL2 | 20000 | 2000 |
| Raji | 40000 | 2000 |
| Jurkat | 20000 | 2000 |

The results of the proliferation inhibition effect of the six ADCs on various cancer cell lines are shown in Table 3.

TABLE 3

| Recombinant chimeric antibody | Inhibitory activity on lymphoma cell proliferation IC$_{50}$(ng/ml) | | | | | | |
|---|---|---|---|---|---|---|---|
| | BJAB | SU-DHL-4 | DoHH2 | Ramos | U-698-M | Granta-519 | WSU-DLCL2 |
| 35B5 | 9.31 | 10.4 | 12.9 | 6 | 10.6 | 101 | 77.8 |
| 78B6 | 8.52 | 10.2 | 11.1 | 7.55 | 12.8 | 106 | 64.7 |
| 85G11 | 8.31 | 8.98 | 6.45 | 4.27 | 10.2 | 38.1 | 30.7 |
| 88B12 | 10 | 15.2 | 24.1 | 7.87 | 14.5 | 208 | 99.3 |
| 104E1 | 10.4 | 11.9 | 5.75 | 6.02 | 9.52 | 20.8 | 18.2 |
| 104A2 | 8.55 | 8.91 | 6.05 | 5.3 | 11.7 | 57.6 | 42.7 |

Example 4: Humanization of Anti-CD79b Antibody

The drug conjugates of the recombinant chimeric antibody expressed by the 104E1 can inhibit the proliferation of lymphoma cells Granta-519 and WSU-DLCL2 with relatively low CD79b expression levels significantly better than the other five antibodies. Therefore, 104E1 was selected for humanization.

The sequence information of antibody 104E1 (based on the Kabat system) is as follows:

HCDR1:
(SEQ ID NO: 1)
GNTFTSYGIN

HCDR2:
(SEQ ID NO: 2)
GEIFPRSGNIYYNEKFKG

HCDR3:
(SEQ ID NO: 3)
AKGGTGDFDY

LCDR1:
(SEQ ID NO: 4)
RSSQNIVHSDGNTYLE

LCDR2:
(SEQ ID NO: 5)
KVSFRLS

LCDR3:
(SEQ ID NO: 6)
FQGSHVPWT mVH:
(SEQ ID NO: 7, nucleotide sequence shown in SEQ ID NO: 38)
QVQLQQSGSELARPGASVKLSCKTSGNTFTSYGINWVKQRTGQ

GLEWIGEIFPRSGNIYYNEKFKGKATLTADKSSSTAYMELRSL

TSEDSAVYFCAKGGTGDFDYWGQGTTLTVSS mVL:
(SEQ ID NO: 8, nucleotide sequence shown in SEQ ID NO: 39)
DVLMTQTPLSLPVSLGDQASISCRSSQNIVHSDGNTYLEWYLQ

KPGQSPKLLIYKVSFRLSGVPDRFSGSGSGTDFTLKIRRVEAE

DLGTYYCFQGSHVPWTFGGGTKLEIK

Nanjing GenScript Biotech Corp. was entrusted to humanize the sequence of 104E1. The specific procedure is as follows: the heavy and light chain variable region sequences of the murine anti-CD79b monoclonal antibody 104E1 were compared in the human germline sequence database, and the human germline sequence IGHV1-69*02 with the highest homology to the 104E1 heavy chain variable region was found, with a homology of 64.3%. Also found was the human germline sequence IGKV2-30*02 with the highest homology to the 104E1 light chain variable region with a homology of 79.0%. Next, the antibody AGC78785.1 (heavy chain variable region, SEQ ID NO: 9) and BAC01734.1 (light chain variable region, SEQ ID NO:10) generated from these two germline sequences were found in the human antibody library, of which the sequence information is as follows:

AGC 78785.1 immunoglobulin heavy chain
variable region [Homo sapiens]
(SEQ ID NO: 9)
QVQLVQSGAEVKKPGSSVKVSCKASGGTFSSYTISWVRQAPGQ

GLEWMGRIIPILGIANYAQKFQGRVTITADKSTSTAYMELSSL

RSEDTAVYYCATSGVGLHFGYFDYWGQGTLVTVSS

BAC01734.1 immunoglobulin kappa light
chain Variable region [Homo sapiens]
(SEQ ID NO: 10)
MKYLLPTAAAGLLLLAAQPAMADVVMTQSPLSLPVTLGQPASI

SCRSSQSLVHSDGNTYLNWFQQRPGQSPRRLIYKVSNRDSGVP

DRFSGSGSGTDFTLKISRVEAEDVGVYYCMQGTHWPLTFGGGT

KVEIKRTVAAPSVFIFPPSDEQLKSGTASVVCLLNNFYPREAK

VQWKVDNALQSGNSQESVTEQDSKDSTYSLSSTLTLSKADYEK

HKVYACEVTHQGLSSPVTKSFNRGECSARQSTPFVCEYQGQS

SDLPQPPVNAGGGSGGGSGG

Using the FR regions of these two human-derived antibodies as the framework, the CDR region sequences were replaced with the corresponding CDR region sequences of murine 104E1 to generate CDR-grafted humanized antibodies, and the sequences were as follows:

HCDR-grafted VH:
(SEQ ID NO: 11)
QVQLVQSGAEVKKPGSSVKVSCKASGNTFTSYGINWVRQAPGQ

GLEWMGEIFPRSGNIYYNEKFKGRVTITADKSTSTAYMELSSL

RSEDTAVYYCATGGTGDFDYWGQGTLVTVSS;

LCDR-grafted VL:
(SEQ ID NO: 12)
DVVMTQSPLSLPVTLGQPASISCRSSQNIVHSDGNTYLEWFQQ

RPGQSPRRLIYKVSFRLSGVPDRFSGSGSGTDFTLKISRVEAE

DVGVYYCFQGSHVPWTFGGGTKVEIK.

To find the amino acid sites in the murine FR regions that play an important role in antibody affinity, a crystal structure with similar homology to the murine 104E1 antibody was searched in the PDB database. As a result, the scFV crystal structure of the anti-polysialic antibody Ab735 was found to have a homology of 77% with the 104E1 antibody sequence, and with a sufficient high resolution. Using this crystal as a structural template, the two sequences were aligned to establish a homology model of the 3WBD scFvs of the 104E1 antibody. According to this homology model, the amino acid sites surrounded by the CDR domain, or within 5 Å to the CDR domains in FR domain of the 104E1 sequence were identified. Then, these sites that may play an important role in antibody affinity are reverse-mutated in the CDR-grafted sequences (SEQ ID NO: 11 and SEQ ID NO: 12) while avoiding glycosylation, deamidation, and oxidation sites, etc. A total of 15 sites were found that may need to be reverse mutated in the heavy chain variable region, including A24T, RV67KA, S84R, T98K, K12A, S16A, V20L, A24T, R38K, M48I, V68A, I70L, Y95F, T98K and V113L and a total of 7 sites that may need to be reverse-mutated in the light chain variable region, including V3L, F41Y, RR50KL, FQ41YL, R51L, V88L and V109L were found. Fab libraries were then constructed according to Genscript's standard protocol and screened by phage display platform. The sequences after humanization with an affinity of not less than the murine 104E1 antibody were screened and sequenced for sequence confirmation.

The light and heavy chain variable regions after humanization are as follows:

```
1. Heavy chain variable region
AS11161:
                                            (SEQ ID NO: 13)
QVQLVQSGAEVKKPGSSVKVSCKTSGNTFTSYGINWVRQAPGQ

GLEWMGEIFPRSGNIYYNEKFKGKVTITADKSTSTAYMELSSL

RSEDTAVYYCAKGGTGDFDYWGQGTLVTVSS;

AS11164:
                                            (SEQ ID NO: 14)
QVQLVQSGAEVKKPGSSVKVSCKTSGNTFTSYGINWVRQAPGQ

GLEWMGEIFPRSGNIYYNEKFKGKVTITADKSTSTAYMELSSL

RSEDTAVYYCAKGGTGDFDYWGQGTLVTVSS;

AS11252:
                                            (SEQ ID NO: 15)
QVQLVQSGAEVKKPGSSVKLSCKTSGNTFTSYGINWVRQAPGQ

GLEWIGEIFPRSGNIYYNEKFKGRVTITADKSTSTAYMELSSL

RSEDTAVYYCAKGGTGDFDYWGQGTLVTVSS;

AS11254:
                                            (SEQ ID NO: 16)
QVQLVQSGAEVKKPGASVKVSCKTSGNTFTSYGINWVKQAPGQ

GLEWMGEIFPRSGNIYYNEKFKGRVTITADKSTSTAYMELSSL

RSEDTAVYYCAKGGTGDFDYWGQGTLVTVSS;

AS11259:
                                            (SEQ ID NO: 17)
QVQLVQSGAEVKKPGSSVKVSCKTSGNTFTSYGINWVKQAPGQ

GLEWIGEIFPRSGNIYYNEKFKGRVTITADKSTSTAYMELSSL

RSEDTAVYYCAKGGTGDFDYWGQGTLVTVSS;

2. Light chain variable region
AS11161:
                                            (SEQ ID NO: 18)
DVVMTQSPLSLPVTLGQPASISCRSSQNIVHSDGNTYLEWYQQ

RPGQSPRLLIYKVSFRLSGVPDRFSGSGSGTDFTLKISRVEAE

DVGVYYCFQGSHVPWTFGGGTKVEIK;

AS11164:
                                            (SEQ ID NO: 19)
DVLMTQSPLSLPVTLGQPASISCRSSQNIVHSDGNTYLEWYQQ

RPGQSPKLLIYKVSFRLSGVPDRFSGSGSGTDFTLKISRVEAE

DVGVYYCFQGSHVPWTFGGGTKVEIK;

AS11252:
                                            (SEQ ID NO: 20)
DVVMTQSPLSLPVTLGQPASISCRSSQNIVHSDGNTYLEWYQQ

RPGQSPRLLIYKVSFRLSGVPDRFSGSGSGTDFTLKISRVEAE

DVGVYYCFQGSHVPWTFGGGTKVEIK;

AS11254:
                                            (SEQ ID NO: 21)
DVVMTQSPLSLPVTLGQPASISCRSSQNIVHSDGNTYLEWYQQ

RPGQSPRLLIYKVSFRLSGVPDRFSGSGSGTDFTLKISRVEAE

DVGVYYCFQGSHVPWTFGGGTKVEIK;

AS11259:
                                            (SEQ ID NO: 22)
DVVMTQSPLSLPVTLGQPASISCRSSQNIVHSDGNTYLEWYQQ

RPGQSPRLLIYKVSFRLSGVPDRFSGSGSGTDFTLKISRVEAE

DVGVYYCFQGSHVPWTFGGGTKVEIK.
```

The light heavy chains after humanization and the IgG1 Fc segment were recombined to obtain the humanized anti-CD79b monoclonal antibody described herein. The Fc sequences used are as follows:

```
Heavy chain constant region:
                                            (SEQ ID NO: 23)
ASTKGPSVFPLAPSSKSTSGGTAALGCLVKDYFPEPVTVSWNS

GALTSGVHTFPAVLQSSGLYSLSSVVTVPSSSLGTQTYICNVN

HKPSNTKVDKKVEPKSCDKTHTCPPCPAPELLGGPSVFLFPPK

PKDTLMISRTPEVTCVVVDVSHEDPEVKFNWYVDGVEVHNAKT

KPREEQYNSTYRVVSVLTVLHQDWLNGKEYKCKVSNKALPAPI

EKTISKAKGQPREPQVYTLPPSRDELTKNQVSLTCLVKGFYPS

DIAVEWESNGQPENNYKTTPPVLDSDGSFFLYSKLTVDKSRWQ

QGNVFSCSVMHEALHNHYTQKSLSLSPGK;

Light chain constant region:
                                            (SEQ ID NO: 24)
RTVAAPSVFIFPPSDEQLKSGTASVVCLLNNFYPREAKVQWKV

DNALQSGNSQESVTEQDSKDSTYSLSSTLTLSKADYEKHKVYA

CEVTHQGLSSPVTKSFNRGEC.
```

The above antibodies were cloned, expressed and purified by gene cloning and recombinant expression methods, and the affinity of the antibody was determined by Biacore (completed by Genscript). Finally, the humanized antibodies AS11161, AS11164, AS11252, AS11254 and AS11259 with best activities were selected. The sequences are as follows:

```
Humanized antibody AS11161
Heavy chain
                                            (SEQ ID NO: 25)
QVQLVQSGAEVKKPGSSVKVSCKTSGNTFTSYGINWVRQAPGQ
```

-continued

GLEWMGEIFPRSGNIYYNEKFKGKVTITADKSTSTAYMELSSL

RSEDTAVYYCAKGGTGDFDYWGQGTLVTVSSASTKGPSVFPLA

PSSKSTSGGTAALGCLVKDYFPEPVTVSWNSGALTSGVHTFPA

VLQSSGLYSLSSVVTVPSSSLGTQTYICNVNHKPSNTKVDKKV

EPKSCDKTHTCPPCPAPELLGGPSVFLFPPKPKDTLMISRTPE

VTCVVVDVSHEDPEVKFNWYVDGVEVHNAKTKPREEQYNSTYR

VVSVLTVLHQDWLNGKEYKCKVSNKALPAPIEKTISKAKGQPR

EPQVYTLPPSRDELTKNQVSLTCLVKGFYPSDIAVEWESNGQP

ENNYKTTPPVLDSDGSFFLYSKLTVDKSRWQQGNVFSCSVMHE

ALHNHYTQKSLSLSPGK

Light chain
(SEQ ID NO: 26)
DVVMTQSPLSLPVTLGQPASISCRSSQNIVHSDGNTYLEWYQQ

RPGQSPRLLIYKVSFRLSGVPDRFSGSGSGTDFTLKISRVEAE

DVGVYYCFQGSHVPWTFGGGTKVEIKRTVAAPSVFIFPPSDEQ

LKSGTASVVCLLNNFYPREAKVQWKVDNALQSGNSQESVTEQD

SKDSTYSLSSTLTLSKADYEKHKVYACEVTHQGLSSPVTKSFN

RGEC

Humanized antibody AS11164
Heavy chain
(SEQ ID NO: 27)
QVQLVQSGAEVKKPGSSVKVSCKTSGNTFTSYGINWVRQAPGQ

GLEWMGEIFPRSGNIYYNEKFKGKVTITADKSTSTAYMELSSL

RSEDTAVYYCAKGGTGDFDYWGQGTLVTVSSASTKGPSVFPLA

PSSKSTSGGTAALGCLVKDYFPEPVTVSWNSGALTSGVHTFPA

VLQSSGLYSLSSVVTVPSSSLGTQTYICNVNHKPSNTKVDKKV

EPKSCDKTHTCPPCPAPELLGGPSVFLFPPKPKDTLMISRTPE

VTCVVVDVSHEDPEVKFNWYVDGVEVHNAKTKPREEQYNSTYR

VVSVLTVLHQDWLNGKEYKCKVSNKALPAPIEKTISKAKGQPR

EPQVYTLPPSRDELTKNQVSLTCLVKGFYPSDIAVEWESNGQP

ENNYKTTPPVLDSDGSFFLYSKLTVDKSRWQQGNVFSCSVMHE

ALHNHYTQKSLSLSPGK

Light chain
(SEQ ID NO: 28)
DVLMTQSPLSLPVTLGQPASISCRSSQNIVHSDGNTYLEWYQQ

RPGQSPKLLIYKVSFRLSGVPDRFSGSGSGTDFTLKISRVEAE

DVGVYYCFQGSHVPWTFGGGTKVEIKRTVAAPSVFIFPPSDEQ

LKSGTASVVCLLNNFYPREAKVQWKVDNALQSGNSQESVTEQD

SKDSTYSLSSTLTLSKADYEKHKVYACEVTHQGLSSPVTKSFN

RGEC

Humanized antibody AS11252
Heavy chain
(SEQ ID NO: 29)
QVQLVQSGAEVKKPGSSVKLSCKTSGNTFTSYGINWVKQAPGQ

GLEWIGEIFPRSGNIYYNEKFKGRVTITADKSTSTAYMELSSL

RSEDTAVYYCAKGGTGDFDYWGQGTLVTVSSASTKGPSVFPLA

PSSKSTSGGTAALGCLVKDYFPEPVTVSWNSGALTSGVHTFPA

VLQSSGLYSLSSVVTVPSSSLGTQTYICNVNHKPSNTKVDKKV

EPKSCDKTHTCPPCPAPELLGGPSVFLFPPKPKDTLMISRTPE

VTCVVVDVSHEDPEVKFNWYVDGVEVHNAKTKPREEQYNSTYR

VVSVLTVLHQDWLNGKEYKCKVSNKALPAPIEKTISKAKGQPR

EPQVYTLPPSRDELTKNQVSLTCLVKGFYPSDIAVEWESNGQP

ENNYKTTPPVLDSDGSFFLYSKLTVDKSRWQQGNVFSCSVMHE

ALHNHYTQKSLSLSPGK

Light chain
(SEQ ID NO: 30)
DVVMTQSPLSLPVTLGQPASISCRSSQNIVHSDGNTYLEWYQQ

RPGQSPRLLIYKVSFRLSGVPDRFSGSGSGTDFTLKISRVEAE

DVGVYYCFQGSHVPWTFGGGTKVEIKRTVAAPSVFIFPPSDEQ

LKSGTASVVCLLNNFYPREAKVQWKVDNALQSGNSQESVTEQD

SKDSTYSLSSTLTLSKADYEKHKVYACEVTHQGLSSPVTKSFN

RGEC

Humanized antibody AS11254
Heavy chain
(SEQ ID NO: 31)
QVQLVQSGAEVKKPGASVKVSCKTSGNTFTSYGINWVKQAPGQ

GLEWMGEIFPRSGNIYYNEKFKGRVTITADKSTSTAYMELSSL

RSEDTAVYYCAKGGTGDFDYWGQGTLVTVSSASTKGPSVFPLA

PSSKSTSGGTAALGCLVKDYFPEPVTVSWNSGALTSGVHTFPA

VLQSSGLYSLSSVVTVPSSSLGTQTYICNVNHKPSNTKVDKKV

EPKSCDKTHTCPPCPAPELLGGPSVFLFPPKPKDTLMISRTPE

VTCVVVDVSHEDPEVKFNWYVDGVEVHNAKTKPREEQYNSTYR

VVSVLTVLHQDWLNGKEYKCKVSNKALPAPIEKTISKAKGQPR

EPQVYTLPPSRDELTKNQVSLTCLVKGFYPSDIAVEWESNGQP

ENNYKTTPPVLDSDGSFFLYSKLTVDKSRWQQGNVFSCSVMHE

ALHNHYTQKSLSLSPGK

Light chain
(SEQ ID NO: 32)
DVVMTQSPLSLPVTLGQPASISCRSSQNIVHSDGNTYLEWYQQ

RPGQSPRLLIYKVSFRLSGVPDRFSGSGSGTDFTLKISRVEAE

DVGVYYCFQGSHVPWTFGGGTKVEIKRTVAAPSVFIFPPSDEQ

LKSGTASVVCLLNNFYPREAKVQWKVDNALQSGNSQESVTEQD

SKDSTYSLSSTLTLSKADYEKHKVYACEVTHQGLSSPVTKSFN

RGEC

Humanized antibody AS11259
Heavy chain
(SEQ ID NO: 33, nucleotide sequence as shown in SEQ ID NO: 36)

QVQLVQSGAEVKKPGSSVKVSCKTSGNTFTSYGINWVKQAPGQ

GLEWIGEIFPRSGNIYYNEKFKGRVTITADKSTSTAYMELSSL

RSEDTAVYYCAKGGTGDFDYWGQGTLVTVSSASTKGPSVFPLA

PSSKSTSGGTAALGCLVKDYFPEPVTVSWNSGALTSGVHTFPA

VLQSSGLYSLSSVVTVPSSSLGTQTYICNVNHKPSNTKVDKKV

EPKSCDKTHTCPPCPAPELLGGPSVFLFPPKPKDTLMISRTPE

VTCVVVDVSHEDPEVKFNWYVDGVEVHNAKTKPREEQYNSTYR

VVSVLTVLHQDWLNGKEYKCKVSNKALPAPIEKTISKAKGQPR

EPQVYTLPPSRDELTKNQVSLTCLVKGFYPSDIAVEWESNGQP

ENNYKTTPPVLDSDGSFFLYSKLTVDKSRWQQGNVFSCSVMHE

ALHNHYTQKSLSLSPGK

Light chain
(SEQ ID NO: 34, nucleotide sequence as shown in SEQ ID NO: 37)

DVVMTQSPLSLPVTLGQPASISCRSSQNIVHSDGNTYLEWYQQ

RPGQSPRLLIYKVSFRLSGVPDRFSGSGSGTDFTLKISRVEAE

DVGVYYCFQGSHVPWTFGGGTKVEIKRTVAAPSVFIFPPSDEQ

LKSGTASVVCLLNNFYPREAKVQWKVDNALQSGNSQESVTEQD

SKDSTYSLSSTLTLSKADYEKHKVYACEVTHQGLSSPVTKSFN

RGEC.

The affinity of the antibody after humanization was tested by the method described in Section 4 of the "Materials and Methods" section. The results are shown in Table 4 below and FIG. 1.

TABLE 4

| Antibody | AS11161 | AS11164 | AS11252 | AS11254 | AS11259 | Chimeric antibody |
|---|---|---|---|---|---|---|
| Analyte | | | CD79b ECD(SEQ ID NO: 35) | | | |
| $K_a$(1/Ms) | 2.02E+06 | 1.91E+06 | 1.48E+06 | 1.53E+06 | 1.68E+06 | 1.62E+06 |
| $K_d$(1/s) | 2.84E−05 | 2.44E−05 | 4.22E−05 | 2.87E−05 | 3.63E−05 | 5.52E−05 |
| $K_D$(M) | 1.40E−11 | 1.28E−11 | 2.85E−11 | 1.87E−11 | 2.16E−11 | 3.41E−11 |
| $R_{max}$(RU) | 52.24 | 60.17 | 59.29 | 62.25 | 48.91 | 63.20 |
| $Chi^2(RU^2)$ | 0.0558 | 0.0448 | 0.0583 | 0.0808 | 0.0757 | 0.0751 |
| U value | 4 | 3 | 2 | 4 | 4 | 2 |

The results showed that the binding KD value of the humanized antibody of the disclosure to CD79b antigen in vitro was about 0.02 nM (measured by Biacore assay, GeneScript) which is comparable to the human-mouse chimeric antibody, the humanization did not make big change in the antibody affinity.

Example 5: Assay for In Vitro Binding Activity of Anti-CD79b Humanized Antibody to Human CD79b Extracellular Domain and the Inhibitory Effect on the Proliferation of Lymphoma Cells of the Drug Conjugate Thereof The in vitro binding activity of the anti-CD79b humanized antibody to the extracellular domain of human CD79b was examined by ELISA as described in Section 1 of the Materials and Methods section. The results are shown in Table 5.

TABLE 5

| Humanized antibody | EC50 by ELISA(ng/ml) |
|---|---|
| AS11161 | 43.1 |
| AS11164 | 64 |
| AS11252 | 49.9 |
| AS11254 | 50.1 |
| AS11259 | 58.3 |

The antibody drug conjugates of the humanized antibody were prepared and the corresponding proliferation inhibition effect on lymphoma cancer cells in vitro (see Example 3 for the method) are shown in Table 6.

TABLE 6

| Humanized ADC | Inhibitory effect on the lymphoma cell proliferation IC$_{50}$(ng/ml) | | | | | | | | |
| --- | --- | --- | --- | --- | --- | --- | --- | --- | --- |
| | BJAB | Ramos | SU_DHL-4 | DoHH2 | U-698-M | Granta-519 | WSU-DLCL2 | Raji | Jurkat |
| AS11161-ADC | 12.2 | 5.04 | 15.9 | 6 | 18.8 | 31.5 | 15.9 | — | — |
| AS11164-ADC | 15.3 | 8.1 | 17.6 | 9.17 | 20.4 | 48.6 | 24.6 | — | — |
| AS11252-ADC | 11.6 | 4.78 | 14.2 | 8.01 | 24.8 | 44.6 | 20.9 | — | — |
| AS11254-ADC | 15.4 | 8.3 | 16.5 | 8.6 | 19.2 | 47.7 | 24 | — | — |
| AS11259-ADC | 10.4 | 4.85 | 16 | 8.9 | 21.5 | 33.4 | 16.5 | — | — |
| Chimeric-104E1-ADC | 8.81 | 4.42 | 9.46 | 4.26 | 15.9 | 29.6 | 16.8 | — | — |

Example 6: Bio-Physical Stability Study of Anti-CD79b Humanized Antibodies

In order to evaluate the stability of the antibodies, five humanized antibodies were stored at different buffers with PH of 4.5, 6.0 or 7.4 at 40° C. for up to 26 days. The properties of the samples were analyzed after storage 1, 6, 12, and 26 days in the above stressed conditions and sample placed at 4° C. as a control. Aliquots are analyzed by ELISA and SEC-HPLC (TOSOH, TSKgel, G3000SWXL).

The results showed that the five humanized antibodies placed at 40° C. for 26 days under three different pH conditions did not have significant difference in the activity determined by ELISA. The purity levels were all above 98% in the SEC assay. No significant aggregates were observed.

Example 7: In Vivo Efficacy Evaluation of Anti-CD79b Humanized Antibody-Drug Conjugates on Lymphoma Tumors in Mice To verify the efficacy of the anti-CD79b humanized antibody, the variant AS11259 was selected and the drug conjugates AS11259-ADCs were prepared according to the method described in Materials and Method 3, then the ability of the ADCs to regress tumors in multiple xenograft models, including Ramos, DoHH2, Granta519 and WSU-DLCL2 was examined.

Linker-Drug Synthesis

Synthesis of Linker-Drug 1:

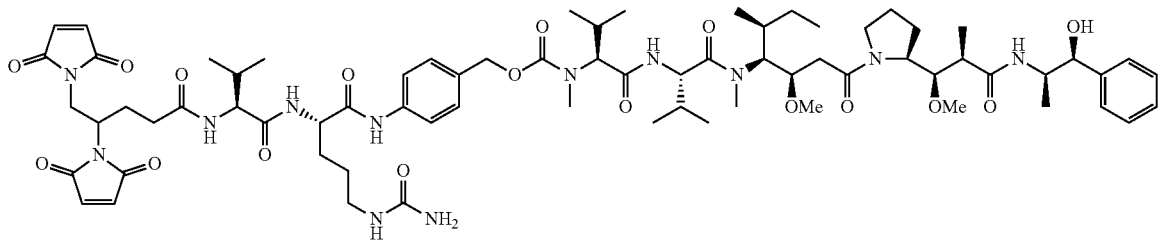 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCC(CN2C(=O)C=CC2=O)N2C(=O)C=CC2=O)C(C)C)cc1)C(C)C]

The linker-drug 1 was prepared as described in WO 2014114207.

Synthesis of Linker-Drug 2

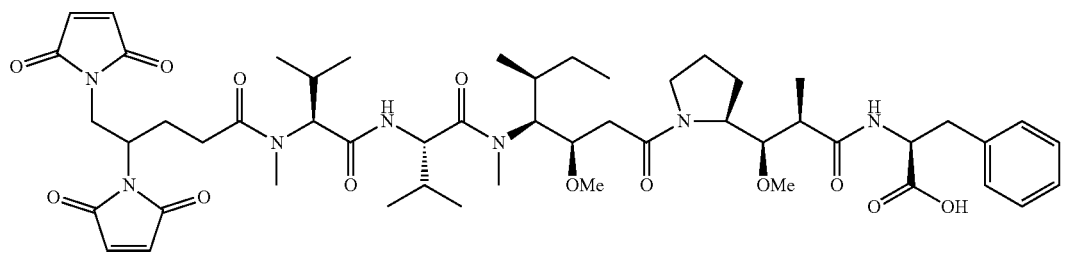 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)CCC(CN1C(=O)C=CC1=O)N1C(=O)C=CC1=O)C(C)C]

The linker-drug 2 was prepared as described in WO 2014114207.

Synthesis of Linker-Drug 3
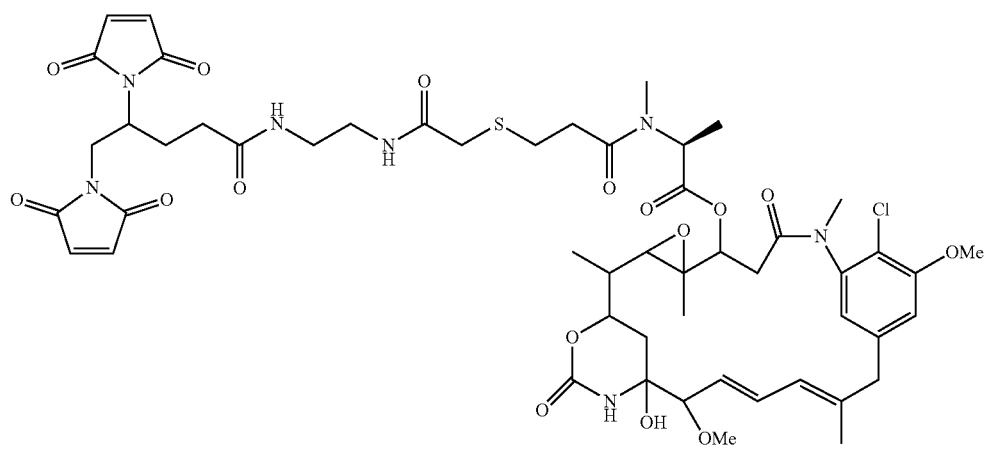 [SMILES: COc1cc2cc(c1Cl)N(C)C(=O)CC(OC(=O)[C@H](C)N(C)C(=O)CCSCC(=O)NCCNC(=O)CCC(CN1C(=O)C=CC1=O)N1C(=O)C=CC1=O)C1(C)OC1C(C)C1CC(O)(NC(=O)O1)C(OC)/C=C/C=C(\C)C2]
Synthesis Scheme:
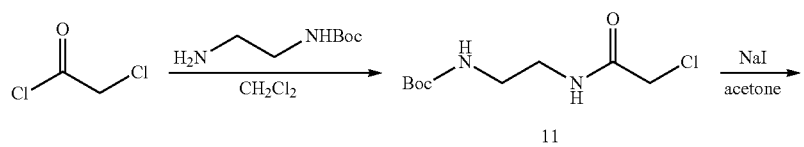
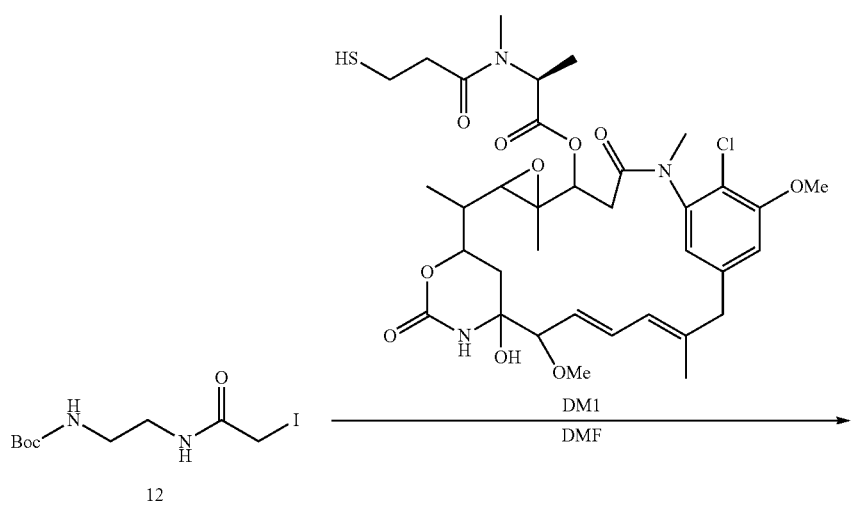

-continued

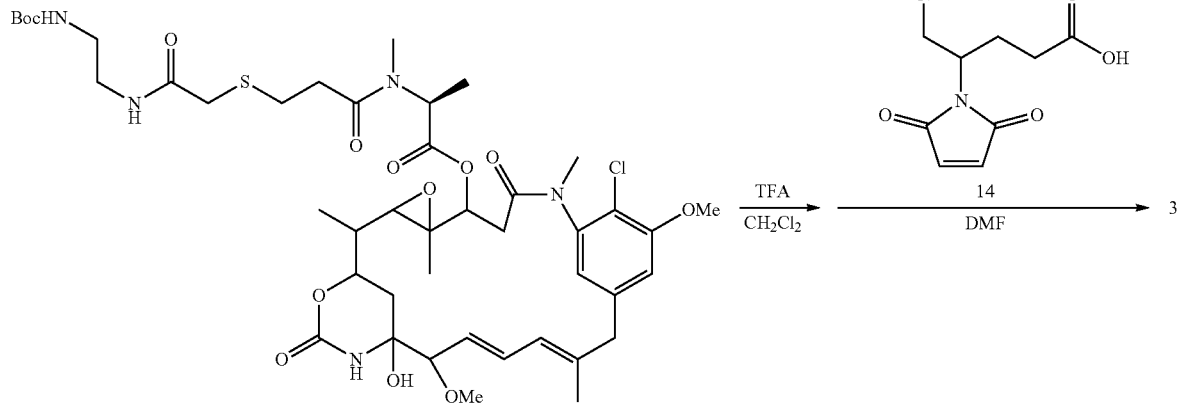

N-tert-butoxycarbonylethylenediamine (710 mg, 4.43 mmol) and diisopropylethylamine (1.55 mL, 8.86 mmol) were dissolved in dichloromethane (10 mL), and then chloroacetyl chloride (500 mg, 4.43 mmol) was added dropwise. The reaction mixture was stirred at room temperature for 16 hours, and then diluted with methylene chloride and washed successively with saturated aqueous ammonium chloride, saturated aqueous ammonium hydrogen carbonate, water and saturated saline. The organic phase was dried with anhydrous sodium sulfate, filtered and concentrated under reduced pressure to obtain the crude compound 11 as a white solid.

The resulting crude 11 was dissolved in acetone (10 mL), and then sodium iodide (3.32 g, 22.2 mmol) was added. The reaction solution was stirred at 50° C. for 16 hours, and then diluted with dichloromethane and washed with water and saturated saline. The organic phase was dried over anhydrous sodium sulfate, filtered and concentrated under reduced pressure. The obtained crude product was purified with silica gel column chromatography (petroleum ether/ethyl acetate 1:1) to obtain the compound 12 (400 mg) as a white solid. (LC-MS (Method 1): retention time 1.61 min; [M+Na]$^+$351.0.

Compound DM1 (40 mg, 0.054 mmol) and compound 12 (35.4 mg, 0.108 mmol) were dissolved in N,N-dimethylformamide (2 mL), and then diisopropylethylamine (29 µL, 0.163 mmol) was added. The reaction mixture was stirred at room temperature for 2 hours and then purified by preparative high-performance liquid chromatography (Method 4: 50%-80% B in 8 min to 95% B in 4 min) to yield the compound 13 (40 mg) as a white solid.

Compound 13 (40 mg, 0.043 mmol) was dissolved in dichloromethane (3 mL), and then trifluoroacetic acid (97 mg, 0.852 mmol) was added. The reaction solution was stirred at room temperature for 3 hours, and then concentrated under reduced pressure. The crude product and compound 14 (18.7 mg, 0.0639 mmol) were dissolved in N,N-dimethylformamide (2 mL), and then HATU (32.4 mg, 0.0852 mmol) and diisopropylethylamine (74 µL, 0.426 mmol) were added sequentially. The reaction solution was stirred at room temperature for 2 hours and then purified by preparative high performance liquid chromatography (Method 4: 50%-80% B in 8 min to 95% B in 4 min) to yield the linker-drug 3 (8.3 mg) as a white solid. LCMS (A018): retention time 1.92 min, [M+Na]$^+$1134.3.

Synthesis of Linker-Drug 4

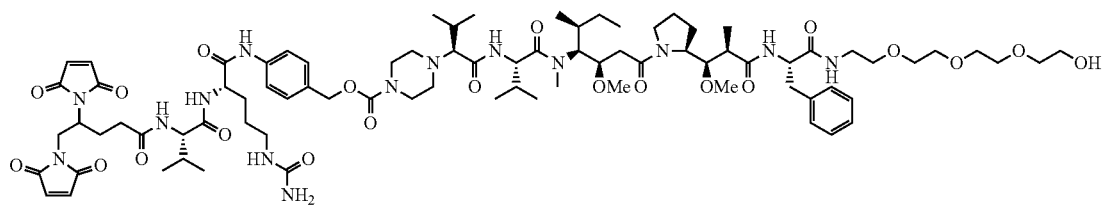 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCOCCOCCOCCO)OC)N(C)C(=O)[C@@H](NC(=O)[C@H](C(C)C)N1CCN(C(=O)OCc2ccc(NC(=O)[C@H](CCCNC(N)=O)NC(=O)[C@@H](NC(=O)CCC(CN3C(=O)C=CC3=O)N3C(=O)C=CC3=O)C(C)C)cc2)CC1)C(C)C]

Synthesizing Scheme:

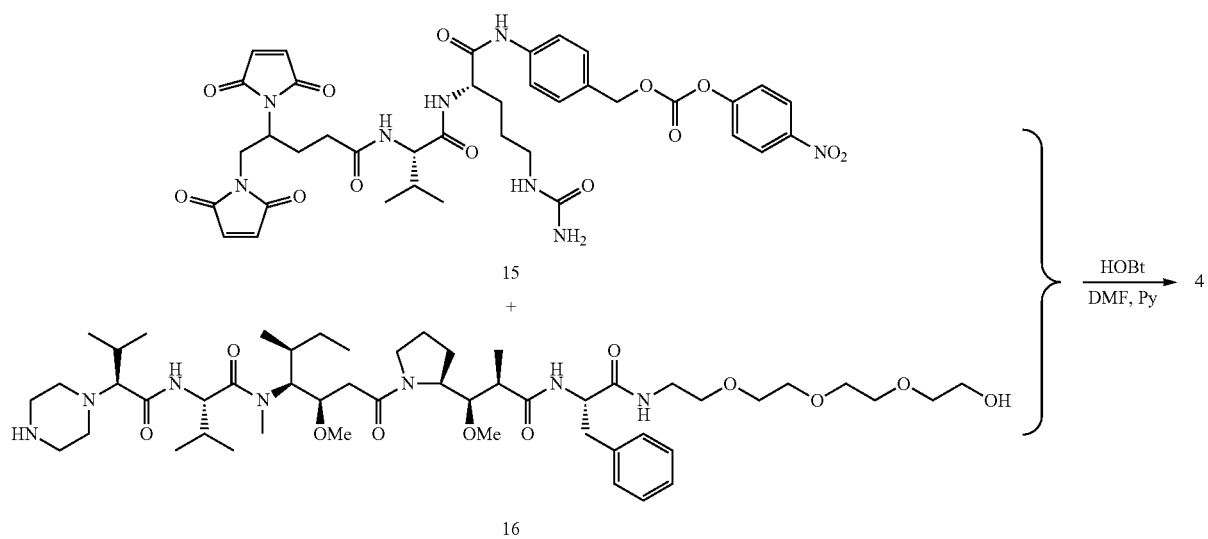 [SMILES: CC(C)[C@H](NC(=O)CCC(CN1C(=O)C=CC1=O)N1C(=O)C=CC1=O)C(=O)N[C@@H](CCCNC(N)=O)C(=O)Nc1ccc(COC(=O)Oc2ccc([N+](=O)[O-])cc2)cc1 ; CC[C@H](C)[C@@H]([C@@H](CC(=O)N1CCC[C@H]1[C@H](OC)[C@@H](C)C(=O)N[C@@H](Cc1ccccc1)C(=O)NCCOCCOCCOCCO)OC)N(C)C(=O)[C@@H](NC(=O)[C@H](C(C)C)N1CCNCC1)C(C)C ; "HOBt"]

Compound 15 (0.25 g, 0.305 mmol, prepared as described in WO2014114207), compound 16 (0.20 g, 0.208 mmol, prepared as described in WO2016192527) and HOBt (28.1 mg, 0.208 mmol) were dissolved in N,N-dimethylformamide (4 mL), and then pyridine (1 mL) was added. The reaction mixture was stirred at room temperature for 16 hours, and then purified by preparative high performance liquid chromatography (Method 5: 50%-80% B in 8 min, then 95% B in 4 min) to yield the linker-drug 4 (45 mg) as a pale pink solid. LCMS (Method 3): retention time 2.127 min, ½ [M+2H]$^{2+}$ 822.0.

Synthesis of Linker-Drug 5

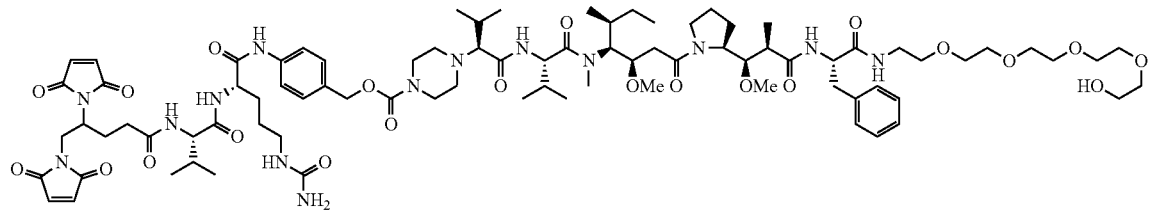 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCOCCOCCOCCOCCO)OC)N(C)C(=O)[C@@H](NC(=O)[C@H](C(C)C)N1CCN(C(=O)OCc2ccc(NC(=O)[C@H](CCCNC(N)=O)NC(=O)[C@@H](NC(=O)CCC(CN3C(=O)C=CC3=O)N3C(=O)C=CC3=O)C(C)C)cc2)CC1)C(C)C]

Synthesizing Scheme:

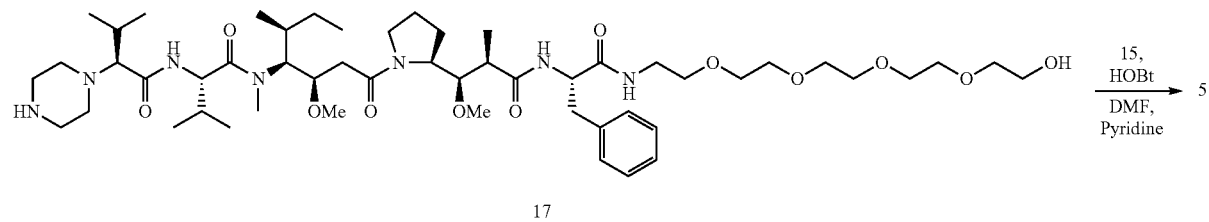 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCOCCOCCOCCOCCO)OC)N(C)C(=O)[C@@H](NC(=O)[C@H](C(C)C)N1CCNCC1)C(C)C ; "15,HOBt"]

Compound 15 (14 mg, 0.017 mmol), compound 17 (14 mg, 0.014 mmol, prepared as described in WO2016192527) and HOBt (3 mg, 0.017 mmol) were dissolved in N,N-dimethylformamide (2 mL), and then pyridine (0.5 mL) was added. The reaction mixture was stirred at room temperature for 16 hours, and then purified by preparative high performance liquid chromatography (Method 5: 45%-75% B in 8 min then 95% B in 4 min) to yield the linker-drug 5 (1.8 mg) as a red solid. LCMS (Method 2): retention time 1.40 min, ½ [M+2H]$^{2+}$ 843.9.

Synthesis of Linker-Drug 6

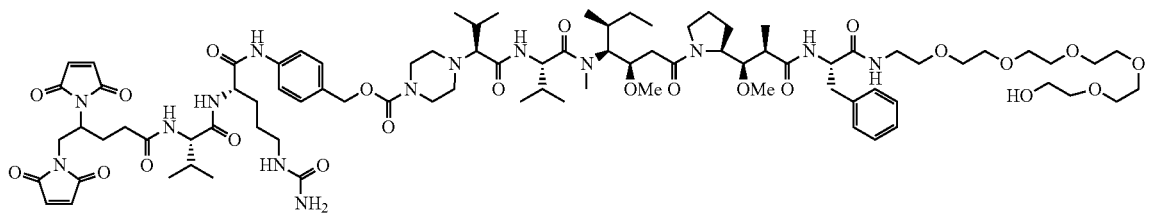

Synthesizing Scheme:

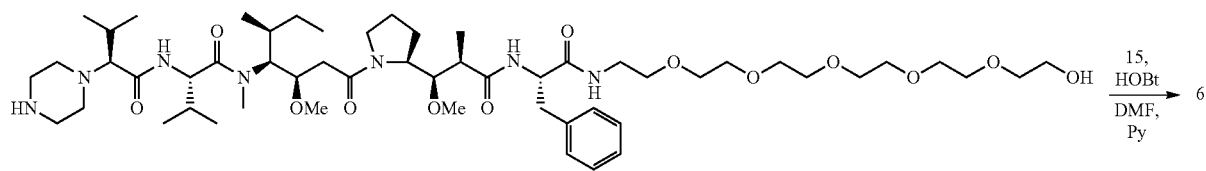

Compound 15 (14 mg, 0.017 mmol), compound 18 (14 mg, 0.013 mmol, prepared as described in WO2016192527) and HOBt (3 mg, 0.017 mmol) were dissolved in N,N-dimethylformamide (2 mL), and then pyridine (0.5 mL) was added. The reaction was stirred at room temperature for 16 hours, and then purified by preparative high performance liquid chromatography (Method 5: 45%-75% B in 8 min then 95% B in 4 min) to yield the linker-drug 6 (2.0 mg) as a red solid. LCMS (Method 2): retention time 1.40 min, ½ [M+2H]$^{2+}$ 865.3.

Synthesis of Linker-Drug 7

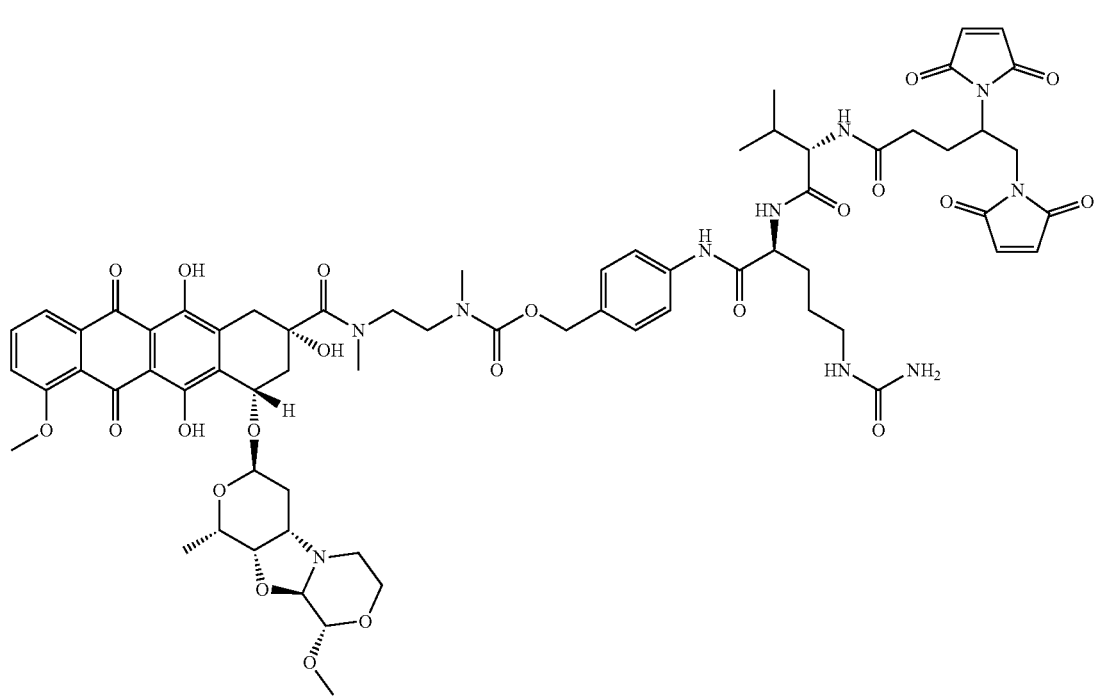

Synthesizing Scheme:

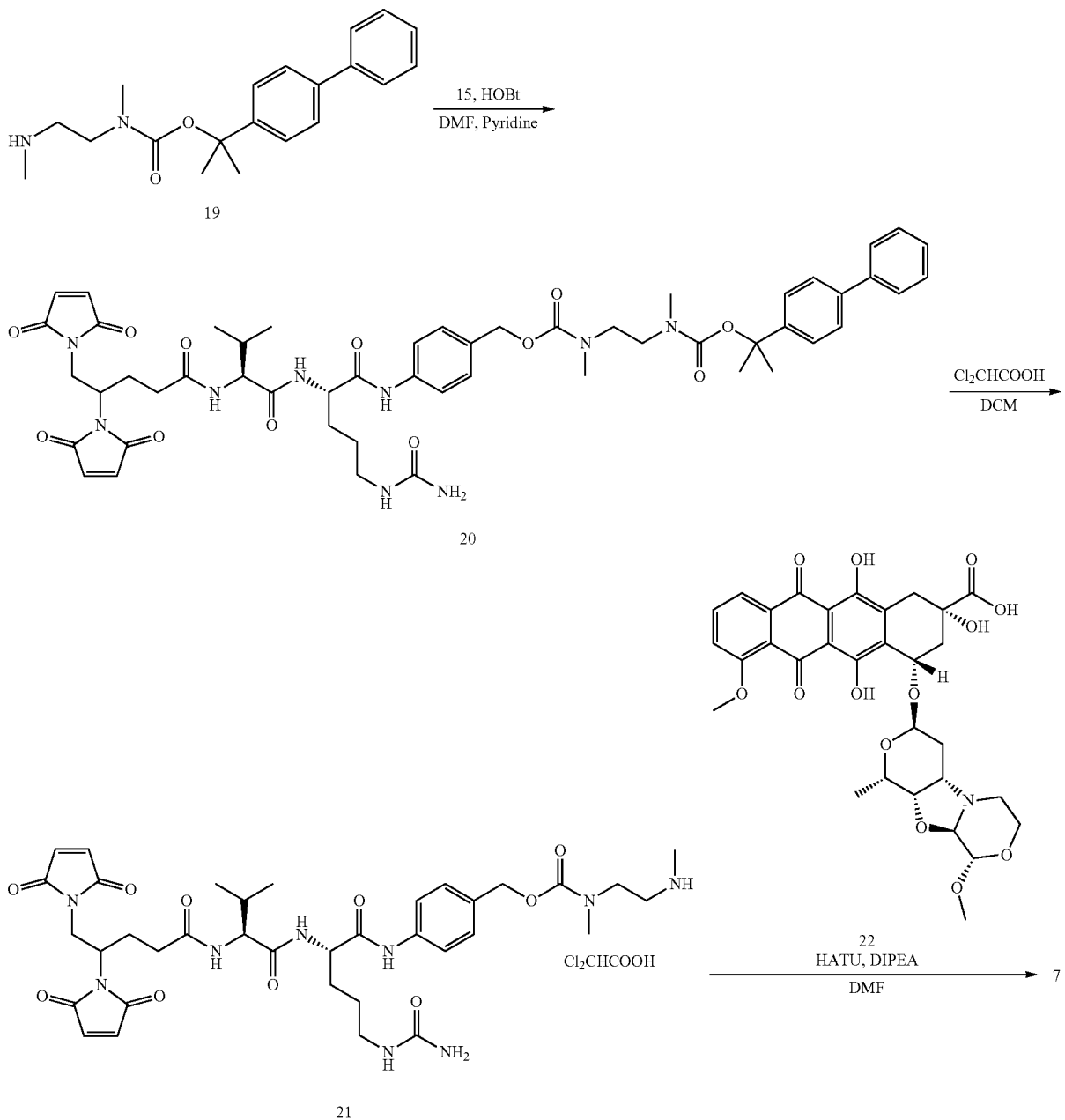

Compound 15 (10 mg, 0.012 mmol) and compound 19 (8 mg, 0.024 mmol, prepared as described in WO2013/149948A1) were dissolved in a mixture of N,N-dimethylformamide (1 mL) and pyridine (0.2 mL), and then HOBt (3.2 mg, 0.024 mmol) was added. The reaction mixture was stirred at room temperature for 2 hours, and then purified using a preparative high-performance liquid chromatography (Method 4: 60%-90% B in 8 min, then 95% B in 4 min) to yield the compound 20 (6.0 mg) as a white solid. LC-MS (Method 3): retention time 2.24 min, [M+Na]$^+$ 1028.3.

Compound 20 (6.0 mg, 0.006 mmol) was dissolved in dichloromethane (1 mL), and then dichloroacetic acid (15 mg, 0.12 mmol) was added. The reaction solution was stirred at room temperature for 2 hours, and then concentrated to remove solvent. The residue was washed with n-hexane/ether (1 ml/ml), filtered and dried to yield the compound 21 (4.5 mg) as a white solid. LC-MS (Method 3): retention time 1.57 min, [M+H]$^+$ 768.3.

Compound 21 (4.5 mg, 0.005 mmol) and compound 22 (5 mg, 0.008 mmol, prepared as described in U.S. Pat. No. 8,389,697 B2) were dissolved in N,N-dimethylformamide (1 mL), and then diisopropylethylamine (2.6 mL, 0.02 mmol) and HATU (3.8 mg, 0.01 mmol) were added. The reaction mixture was stirred at room temperature for 1 hour, and then purified using a preparative high-performance chromatography (Method 5: 50%-80% B in 8 min, then to 95% B in 4 min) to yield the linker-drug 7 (0.9 mg) as a red solid. LCMS (Method 3): retention time 2.05 min, [M+H]$^+$ 1378.3.

Synthesis of Linker-Drug 8

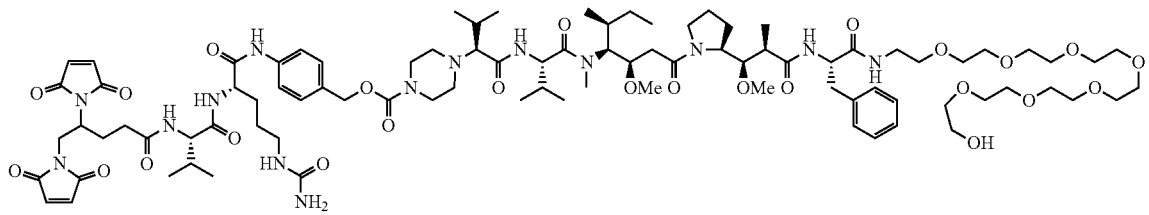 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCOCCOCCOCCOCCOCCOCCOCCO)OC)N(C)C(=O)[C@@H](NC(=O)[C@H](C(C)C)N1CCN(C(=O)OCc2ccc(NC(=O)[C@H](CCCNC(N)=O)NC(=O)[C@@H](NC(=O)CCC(CN3C(=O)C=CC3=O)N3C(=O)C=CC3=O)C(C)C)cc2)CC1)C(C)C]

Synthesizing Scheme:

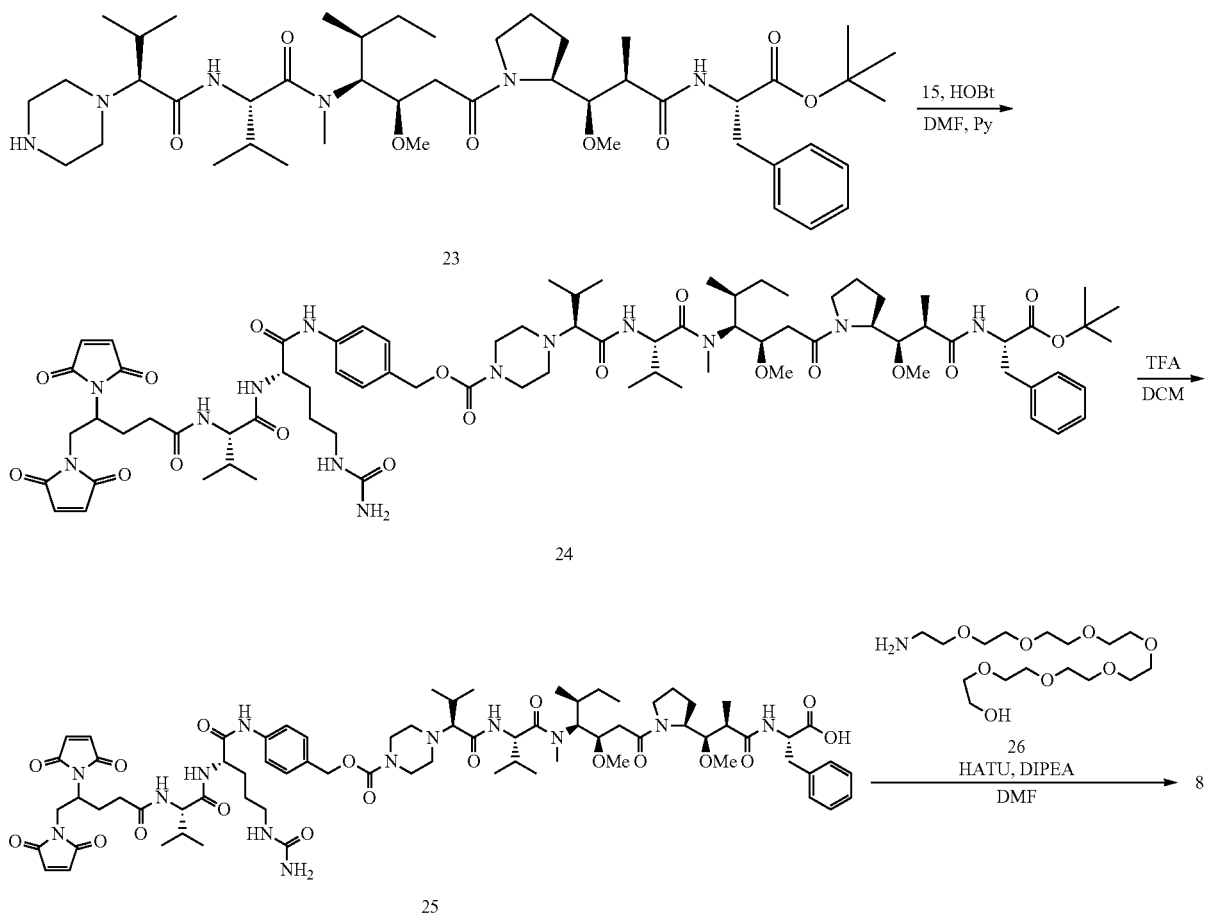

Compound 15 (100 mg, 0.122 mmol), compound 23 (60 mg, 0.071 mmol, prepared as described in WO2016192527) and HOBt (10 mg, 0.071 mmol) were dissolved in dry DMF (2 mL), and then pyridine (0.5 mL) was added. The reaction mixture was stirred at room temperature for 16 hours, and then purified by preparative high-purity liquid chromatography (Method 5: 50%-80% B in 8 min, then to 95% B in 4 min) to yield the compound 24 (30 mg) as a white solid. LCMS (Method 3): retention time 2.41 min, ½ [M+2H]$^{2+}$ 762.0.

Compound 24 (30 mg, 0.0197 mmol) was dissolved in dichloromethane (1.5 mL), and then trifluoroacetic acid (0.5 mL) was added. The reaction mixture was stirred at room temperature for 3 hours, and then concentrated to remove the solvent. The residue was purified by preparative high-performance liquid chromatography (method X) to yield the compound 25 (15 mg) as a white powdery solid.

Compound 25 (15 mg, 0.0197 mmol) and compound 26 (7 mg, 0.0189 mmol, prepared as described in Journal of Organic Chemistry, 2001, 66, 4494-4503) were dissolved in dry DMF (0.4 mL), and then HATU (7.2 mg, 0.0189 mmol) and DIPEA (3.7 mg, 0.0286 mmol) were added. The reaction mixture was stirred at room temperature for 2 hours, and then purified by preparative high performance liquid chromatography (Method 5: 50%-80% B in 8 min, then to 95% B in 4 minutes) to obtain the linker-drug 8 (4.8 mg) as a white powdery solid. LCMS (Method 2): retention time 1.37 minutes, ½ [M+2E1]$^{2+}$ 909.5.

Synthesis of Linker-Drug 9

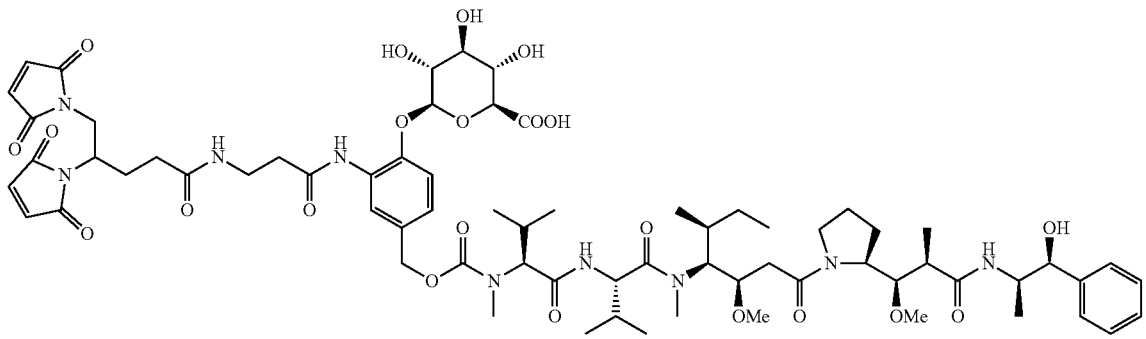 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(O[C@@H]2O[C@H](C(=O)O)[C@@H](O)[C@H](O)[C@H]2O)c(NC(=O)CCNC(=O)CCC(CN2C(=O)C=CC2=O)N2C(=O)C=CC2=O)c1)C(C)C]

Synthesizing Scheme:

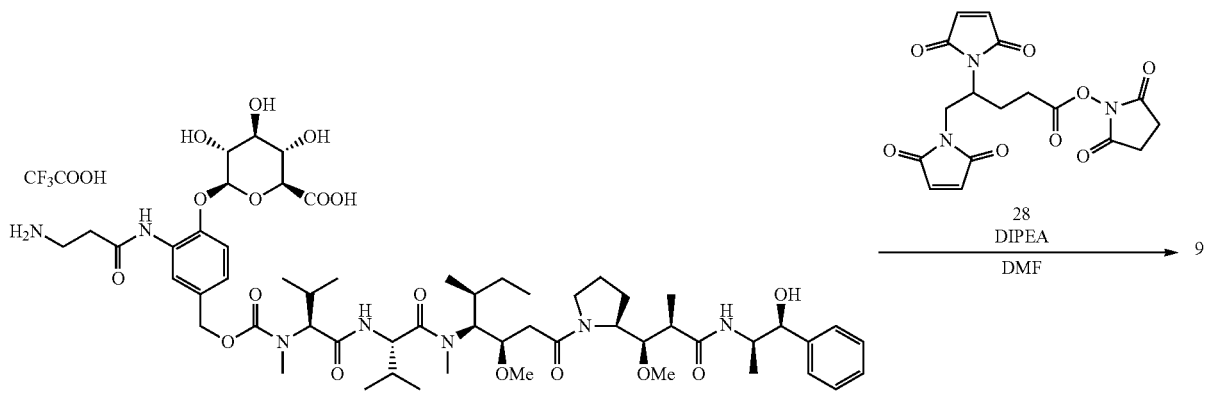

Compound 27 (165 mg, 0.132 mmol, prepared as described in WO2007011968) and compound 28 (90 mg, 0.231 mmol, prepared as described in WO 2014114207) were dissolved in DMF (2 mL), and then DIPEA (51 mg, 0.395 mmol) was added. The reaction mixture was stirred at room temperature for 0.5 hour, and then quenched by addition of glacial acetic acid (50 μL). The mixture was purified by preparative high performance liquid chromatography (method 4: 50%-80% B in 8 minutes, then to 95% B in 4 minutes) to yield the linker-Drug 9 (128 mg) as a white powdery solid. LCMS (Method 2): retention time 1.51 min, ½ $[M+2H]^{2+}$ 702.8.

Synthesis of Linker-Drug 10

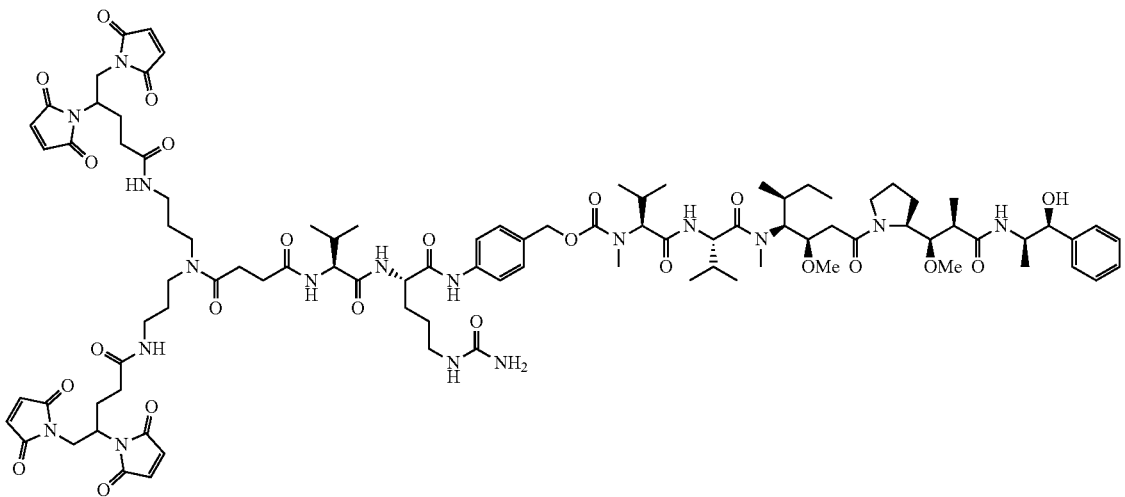 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCC(=O)N(CCCNC(=O)CCC(CN2C(=O)C=CC2=O)N2C(=O)C=CC2=O)CCCNC(=O)CCC(CN2C(=O)C=CC2=O)N2C(=O)C=CC2=O)C(C)C)cc1)C(C)C]

The synthesis of the linker-drug 10 was prepared as described in CN 201710691056.X.

Preparation of Antibody-Drug Conjugates

Tris(2-carboxyethyl)phosphine hydrochloride (TCEP, 10 eq, stock concentration 10 mM) was added to a solution of antibody AS11259 (IgG1) (20 mM sodium dihydrogen phosphate-disodium hydrogen phosphate buffer, 150 mM sodium chloride, pH 7.2). The reaction was incubated for 2 hours in a 37° C. thermostat water bath. The reaction solution was cooled to about room temperature, and then buffer-exchanged by ultrafiltration (Merck Millipore Amicon® Ultra, 50000 MWCO) or gel filtration into buffer (100 mM potassium dihydrogen phosphate-dipotassium hydrogen phosphate, 100 mM sodium chloride, 1 mM Diethylenetriamine pentaacetic acid, pH 7.0-8.0) or buffer (20 mM citric acid-trisodium citrate, 50 mM sodium chloride, 1 mM diethylenetriaminepentaacetic acid, pH 6.0), to which dimethyl sulfoxide and the linker-Drug 1 prepared as described in Example 1 (dimethyl sulfoxide stock solution, 3-10 equivalents relative to the antibody) were added, ensuring that the volume of dimethyl sulfoxide in the reaction solution was about 10-15%. The conjugation reaction was carried out at 10° C. for 0.5 hour.

An excess of cysteine solution was added to the above conjugation solution to quench the unreacted linker-drug 1, and the quenching was carried out at 10° C. for 30 minutes. The reaction solution was first subjected to ultrafiltration (Merck Millipore Amicon® Ultra, 50000 MWCO) or gel filtration to remove the linker-drug 1-cysteine adduct and excess cysteine, and then the sample was buffer-exchanged into a storage buffer (20 mM sodium dihydrogen phosphate-dibasic sodium phosphate buffer, 150 mM sodium chloride, pH 7.2). The obtained solution was sterilized via a 0.22 μm pore size filter (Merck Millex-GV Filter) to obtain an antibody-drug conjugate AS11259-ADC-001, which was stored at 4° C.

Other antibody-drug conjugates of the present invention, AS11259-ADC-002 to AS11259-ADC-011, were prepared according to the above preparation procedure, using linker-drug 2-10 to replace linker-drug 1, respectively. The antibody-drug conjugate AS11259-ADC-0012 was obtained by conjugating the antibody AS11259 with the linker-drug 1, wherein the antibody was reduced via partial reduction mode, with an average of two pairs of disulfide bonds being reduced.

Table 6 shows a summary of the antibody drug conjugates prepared in this disclosure.

TABLE 6

| ADC | Linker-drug | Linker-drug e.q.(to antibody) |
|---|---|---|
| AS11259-ADC-001 | 1 | 6 |
| AS11259-ADC-002 | 2 | 6 |
| AS11259-ADC-003 | 3 | 8 |
| AS11259-ADC-004 | 4 | 7 |
| AS11259-ADC-005 | 5 | 8 |
| AS11259-ADC-006 | 6 | 8 |
| AS11259-ADC-007 | 7 | 8 |
| AS11259-ADC-008 | 8 | 8 |
| AS11259-ADC-010 | 9 | 6.6 |
| AS11259-ADC-011 | 10 | 4 |
| AS11250-ADC-0012* | 1 | 4 |

*The number of equivalent of TCEP relative to antibody is 3.

Characterization of Antibody-Drug Conjugates

1) Determination of Average DAR Value

The average DAR value was calculated using hydrophobic chromatography HIC (see Anal. Chem. 2013, 85, 1699-1704). Hydrophobic interaction chromatography was performed on an Agilent 1100 (Agilent 1100). The stationary phase was a TSKgel butyl-NPR column (4.6×35 mm, 2.5 Tosoh (Shanghai) Biotech Co., Ltd.). The eluting gradient was a linear gradient, displaced from 100% buffer A [50 mM potassium phosphate (pH 7.0)+1.5 M ammonium sulfate] to 100% buffer B [80% v/v 50 mM potassium phosphate (pH) 7.0)+20% v/v isopropanol] in 25 minutes. The flow rate was 0.8 mL/min, the column temperature was set at 30° C., and the detection wavelength was set at 230 nm and 280 nm.

The results of the measurements of the average DAR values of the antibody drug conjugates in the disclosure are shown in Table 7.

TABLE 7

Average DAR results for antibody drug conjugates

| ADC | Average DAR value |
|---|---|
| AS11259-ADC-001 | 4.0 |
| AS11259-ADC-002 | NA |
| AS11259-ADC-003 | NA |
| AS11259-ADC-004 | 4.0 |
| AS11259-ADC-005 | 4.2 |
| AS11259-ADC-006 | 4.1 |
| AS11259-ADC-007 | NA |
| AS11259-ADC-008 | 4.1 |
| AS11259-ADC-010 | 4.0 |
| AS11259-ADC-011 | 2.1 |
| AS11259-ADC-0012 | 1.7 |

NA: Not detected, but based on the commonality of the linkers, the average DAR value should also be close to 4.

Affinity Assay of Antibody-Drug Conjugates to Antigen

Indirect ELISA method was used to determine the binding ability of the antibody or antibody drug conjugate to the corresponding antigen: the CD79b antigen was ligated to the solid phase carrier (96-well ELISA plate) to form a solid phase antigen, and then the unbound antigen was washed and removed; A gradient-diluted antibody drug conjugate prepared by the present invention or a corresponding antibody thereof was added, wherein a specific antibody bound to an antigen to form a solid phase antigen-antibody complex, and an antibody or antibody drug conjugate that did not bind to a solid phase antigen was removed by washing. An ELISA anti-antibody was added to bind with the antibody or ADC antibody bound to the solid phase antigen, and unbound anti-antibody was removed by washing. Substrate solution was added, and then the optical density (OD) value at 450 nm/630 nm was read with a microplate reader T, based on which a curve was plotted, and the $EC_{50}$ was calculated.

The measurements of the affinity of the antibody drug conjugate prepared herein for CD79b antigen are shown in Table 8.

TABLE 8

Affinity results of antibody drug conjugates to CD79b antigen

| ADC | $EC_{50}$(ng/mL) |
|---|---|
| AS11259 | 17.8 |
| AS11259-ADC-001 | 31.7 |
| AS11259-ADC-002 | 24.1 |
| AS11259-ADC-003 | 16.2 |
| AS11259-ADC-004 | 32.2 |
| AS11259-ADC-005 | 46.9 |
| AS11259-ADC-006 | 50.2 |
| AS11259-ADC-007 | 62.9 |
| AS11259-ADC-008 | 29.0 |

TABLE 8-continued

Affinity results of antibody drug conjugates to CD79b antigen

| ADC | $EC_{50}$(ng/mL) |
|---|---|
| AS11259-ADC-010 | 23.2 |
| AS11259-ADC-011 | 23.6 |
| AS11259-ADC-0012 | 31.4 |

As can be seen from the Table 8, the antibody drug conjugates prepared herein have no significant difference in affinity for the antigen compared to the naked antibody AS11259.

Cell Proliferation Inhibition by Antibody-Drug Conjugates

The cytostatic activity of the antibody or antibody drug conjugate was determined by the following method: mammalian cells expressing a tumor-associated antigen or receptor protein (the present assay used a Ramos cell expressing CD79b antigen) were inoculated in a 96-well plate, with each well inoculated with 40,000 cells, which were suspended in 100 µL of RPMI 1640 medium containing 10% FBS (GIBCO); initial concentration of ADC sample was 2 µg/mL, and 3-time serial dilution was performed with RPMI 1640 medium containing 2% FBS (GIBCO); in the original medium, 100 µL of the gradient-diluted ADC sample was added to each well, and the initial concentration of the drug was 1 ug/ml; incubation was continued at 37° C. and 5% $CO_2$ for 72 hours; 50 µL of the original medium was removed, and then 70 µL of CCK-8 developing solution (CCK-8: RPMI 1640=2:5) was added to each well, followed by further culturing for 60-75 minutes; the absorbance at 450 nm/630 nm was read with a ELISA reader, based on which a curve was plotted and the $IC_{50}$ was calculated. The results of inhibition of cell proliferation by the antibody drug conjugate prepared herein are shown in Table 9.

TABLE 9

Results of inhibition of cell proliferation by antibody drug conjugates

| ADC | $IC_{50}$ (ng/mL) |
|---|---|
| AS11259-ADC-001 | 5.5 |
| AS11259-ADC-002 | 14.5 |
| AS11259-ADC-003 | 70.2 |
| AS11259-ADC-004 | 2.9 |
| AS11259-ADC-005 | 5.2 |
| AS11259-ADC-006 | 5.0 |
| AS11259-ADC-007 | 8.1 |
| AS11259-ADC-008 | 2.4 |
| AS11259-ADC-010 | 3.9 |
| AS11259-ADC-011 | 10.2 |
| AS11259-ADC-0012 | 13.2 |

The results showed that the antibody drug conjugates prepared in this disclosure all have good cell proliferation inhibitory effects.

Ramos Model

Ramos cells were cultured in RPMI 1640 medium containing 10% fetal bovine serum at 37° C., 5% $CO_2$. Cells were counted and collected in logarithmic growth phase, resuspended in 1:1 PBS and Matrigel, and subcutaneously inoculated to the right side of the mice (CB17/SCID mice, female, 8-9 weeks, average body weight 18.4 g, purchased from Shanghai Lingchang Biotechnology Co., Ltd., animal certificate number: 2013001832088; feeding environment: SPF level). The volume of cells inoculated per mouse was 0.1 ml, and the amount of cells inoculated was $1\times10^7$ cells per mouse. When average tumor size reached to 197 $mm^3$, the body weights were weighed, and the mice were grouped randomly, followed by the initiation of the administration. The administration was via tail vein, and the administration frequency was one time only.

Result Evaluation Standard

Relative tumor inhibition rate TGI (%): TGI=1−T/C (%). T/C % is the relative tumor growth rate, that is, the percentage ratio of relative tumor volume or tumor weight of the treatment group to the control group at a certain time point. T and C are the relative tumor volumes (RTV) of the treatment group and the control group at a specific time point respectively.

The formula is as follows: T/C %=$T_{RTV}/C_{RTV}$*100% ($T_{RTV}$: mean RTV in the treatment group; $C_{RTV}$: mean RTV in the vehicle control group; RTV=$V_t/V_0$, $V_0$ is the tumor volume of the animal at the time of grouping, $V_t$ is the tumor volume of the animal after treatment).

The tumor volume calculation formula is: long diameter× short $diameter^2/2$. The day of tumor cell inoculation was defined as day 0. Tumors were measured twice weekly after administration.

The mean tumor volume of the vehicle control group reached 3003 $mm^3$ on the 14th day after administration (PG-D14). The euthanasia was performed and the relative tumor inhibition rate of the other drug groups on the 14th day after administration was calculated. On the 45th day after the administration, the experiment was terminated, and all the rest mice that were continuously observed were euthanized, while the number of mice in which tumors were regressed completely in each group was recorded.

Experimental Results

Figure 2:
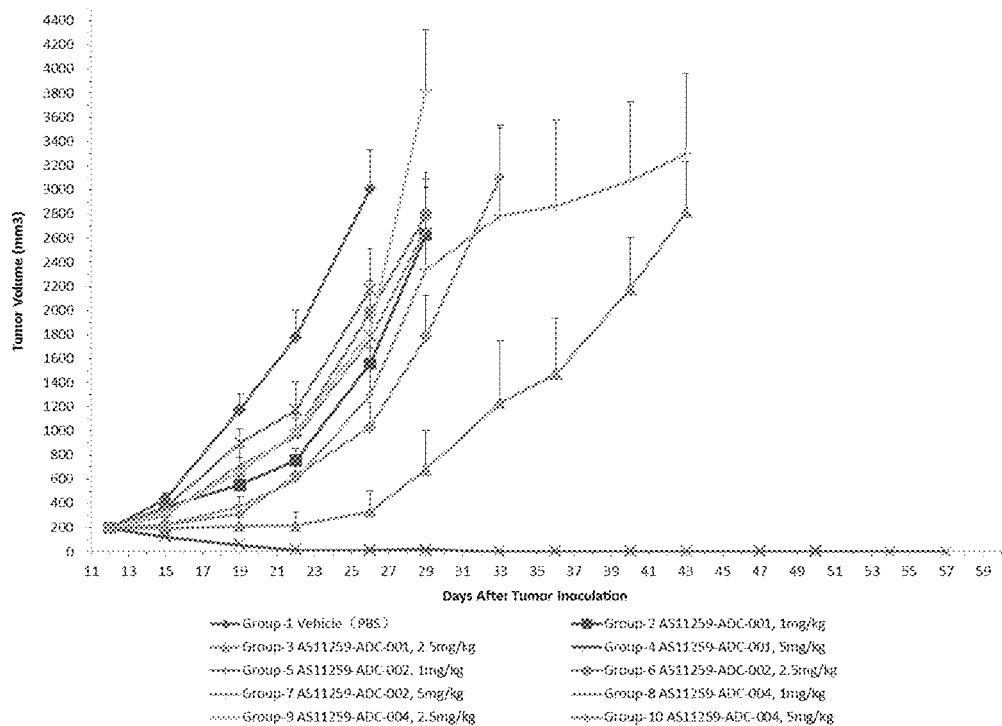
FIG. 2: Therapeutical effect of AS11259-ADC-001, 002, 004 on subcutaneous xenografts of human B-cell lymphoma Ramos in nude mice.
Figure 3:
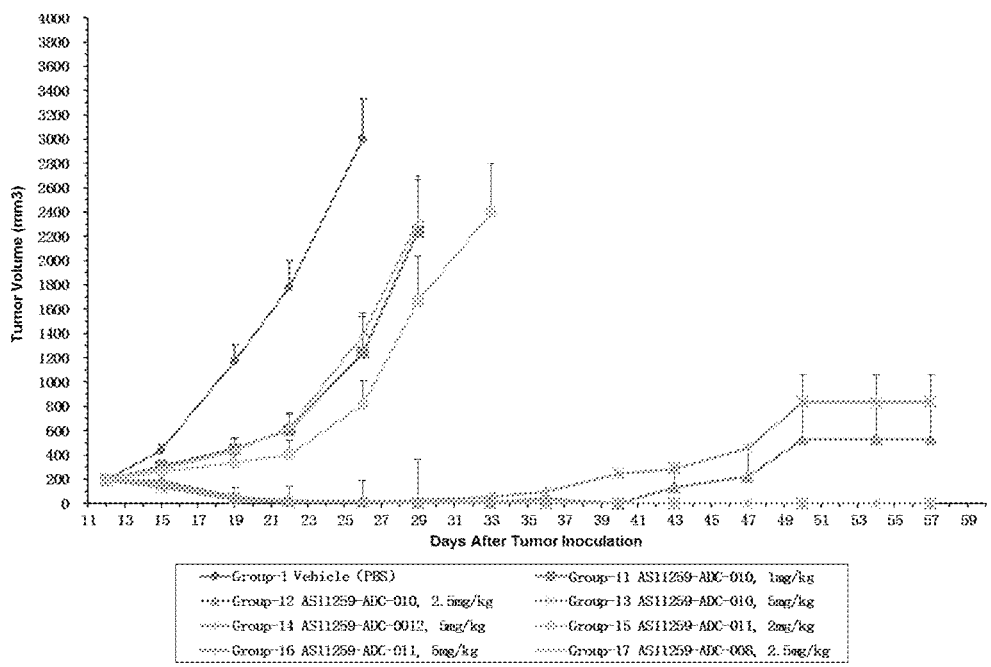
FIG. 3: Therapeutical effect of AS11259-ADC-010, 0012, 011, 008 on subcutaneous xenografts of human B-cell lymphoma Ramos in nude mice.

The experimental results are shown in Table 10 and FIGS. 2 and 3.

TABLE 10

Therapeutical efficacy of AS11259-ADC-001, 002, 004, 008, 010, 011 on the subcutaneous xenografts of nude mice with human B-cell lymphoma Ramos nude mice

| Group | Animals | Test subject | Dosage (mg/kg) | PG-D14 ($mm^3$) | TGI (%) | P | Body weight(g) | PG-D45 Total resolved |
|---|---|---|---|---|---|---|---|---|
| 1 | 6 | Vehicle (PBS) | — | 3003 ± 329 | — | — | 21.3 ± 0.9 | 0 |
| 2 | 6 | AS11259-ADC-001 | 1 | 1558 ± 234 | 48.7 | 0.023 | 21.1 ± 0.8 | 0 |
| 3 | 6 | AS11259-ADC-001 | 2.5 | 333 ± 170 | 90.1 | 0.001 | 20.7 ± 0.4 | 0 |
| 4 | 6 | AS11259-ADC-001 | 5 | 14 ± 6 | 99.6 | 0.001 | 20.4 ± 0.2 | 6 |
| 5 | 6 | AS11259-ADC-002 | 1 | 2171 ± 343 | 28.4 | 0.195 | 22.3 ± 0.7 | 0 |
| 6 | 6 | AS11259-ADC-002 | 2.5 | 1986 ± 259 | 33.2 | 0.126 | 21.0 ± 0.4 | 0 |
| 7 | 6 | AS11259-ADC-002 | 5 | 1294 ± 398 | 60.1 | 0.014 | 21.6 ± 0.5 | 0 |
| 8 | 6 | AS11259-ADC-004 | 1 | 1762 ± 412 | 42.6 | 0.075 | 22.0 ± 0.9 | 0 |

TABLE 10-continued

Therapeutical efficacy of AS11259-ADC-001, 002, 004, 008, 010, 011 on the subcutaneous xenografts of nude mice with human B-cell lymphoma Ramos nude mice

| Group | Animals | Test subject | Dosage (mg/kg) | PG-D14 (mm$^3$) | TGI (%) | P | Body weight(g) | PG-D45 Total resolved |
|---|---|---|---|---|---|---|---|---|
| 9  | 6 | AS11259-ADC-004  | 2.5 | 1835 ± 155 | 41.2 | 0.027 | 21.7 ± 0.5 | 0 |
| 10 | 6 | AS11259-ADC-004  | 5   | 1030 ± 201 | 66.0 | 0.003 | 20.8 ± 0.5 | 0 |
| 11 | 6 | AS11259-ADC-010  | 1   | 1241 ± 295 | 57.8 | 0.014 | 21.2 ± 0.2 | 0 |
| 12 | 6 | AS11259-ADC-010  | 2.5 | 15 ± 6     | 99.5 | 0.001 | 20.4 ± 0.4 | 5 |
| 13 | 6 | AS11259-ADC-010  | 5   | 12 ± 6     | 99.6 | 0.001 | 20.5 ± 0.3 | 6 |
| 14 | 6 | AS11259-ADC-0012 | 5   | 13 ± 6     | 99.6 | 0.001 | 19.5 ± 0.3 | 5 |
| 15 | 6 | AS11259-ADC-011  | 2   | 818 ± 191  | 73.8 | 0.001 | 20.2 ± 0.5 | 0 |
| 16 | 6 | AS11259-ADC-011  | 5   | 17 ± 5     | 99.4 | 0.001 | 19.9 ± 0.5 | 6 |
| 17 | 6 | AS11259-ADC-008  | 2.5 | 1390 ± 179 | 54.8 | 0.009 | 20.4 ± 0.4 | 0 |

The mean tumor volume of the vehicle control group reached 3003 mm$^3$ on the 14th day after administration (PG-D14).

The test drug AS11259-ADC-001 treatment group produced significant anti-tumor effects in three doses (1 mg/kg, 2.5 mg/kg, 5 mg/kg) compared with the vehicle control group, suggesting significant dose-response relationship. The mean tumor volumes on the 14th day after administration (PG-D14) for the 3 dosage groups were 1558 mm$^3$, 337 mm$^3$, and 14 mm$^3$, respectively, and the tumor growth inhibition (TGI) were 48.7%, 90.1%, and 99.6, respectively, which were statistically significantly different from the control group (p values are 0.023, 0.001, 0.001, respectively). In the high-dose (5 mg/kg) group, the tumor growth was significantly inhibited in the mice after administration. On the 10th day after the administration (PG-D10), the tumor in 3 mice out of 6 mice began to disappear, and fully disappeared on the 24th day after the administration (PG-D24) in all 6 mice. At the end of the experiment (PG-D45), there was no regression in the mouse tumor.

The test drug AS11259-ADC-002 treatment group produced a certain anti-tumor effect at the doses of 1 mg/kg and 2.5 mg/kg, compared with the vehicle control group. On the 14th day after administration (PG-D14), the mean tumor volume was 2171 mm$^3$ and 1986 mm$^3$, respectively, and the tumor growth inhibition (TGI) was 28.4% and 33.2%, respectively, but there was no statistically significant difference from the relative vehicle control groups (p values of 0.195 and 0.126, respectively). The AS11259-ADC-002 treatment group produced a significant anti-tumor effect compared to the vehicle control group at a dose of 5 mg/kg, and the mean tumor volume was 1294 mm$^3$ on day 14 after administration (PG-D14). The tumor growth inhibition (TGI) was 60.1%, which was statistically significantly different from the control group (p=0.014). The anti-tumor effect of the test drug AS11259-ADC-002 showed a significant dose-response relationship.

The test drug AS11259-ADC-004 treatment group produced a certain anti-tumor effect compared with the vehicle control group at the dose of 1 mg/kg. The average tumor volume on the 14th day after administration (PG-D14) was 1762 mm$^3$. The relative tumor inhibition rate was 42.6%, but there was no statistically significant difference compared with the vehicle control group (p=0.075). The test drug AS11259-ADC-004 produced significant anti-tumor effect compared with the vehicle control group at the dose of 2.5 mg/kg and 5 mg/kg. On the 14th day after administration (PG-D14), the average tumor volume was 1835 mm$^3$ and 1030 mm$^3$, respectively, and the tumor growth inhibition (TGI) was 41.2% and 66.0% respectively, both had statistically significant differences compared to vehicle control group (p values of 0.027 and 0.003, respectively). The anti-tumor effect of the test drug AS11259-ADC-004 showed a significant dose-response relationship.

The test drug AS11259-ADC-010 treatment group produced significant anti-tumor effects at three concentrations (1 mg/kg, 2.5 mg/kg, 5 mg/kg) compared with the vehicle control group, and showed significant dose-response relationship. The average tumor volume on the 14th day after administration (PG-D14) was 1241 mm$^3$, 15 mm$^3$, and 12 mm$^3$, respectively, and the tumor growth inhibition (TGI) were 57.8%, 99.5%, and 99.6%, respectively. There was a statistically significant difference (p values of 0.014, 0.001, 0.001, respectively) compared with the control group. In the median-dose (2.5 mg/kg) group, the tumor growth was significantly inhibited after administration. On the 10th day after the administration (PG-D10), the tumor of 2 mice out of 6 began to disappear. On the 28th day after administration (PG-D28), all the tumors of 6 mice had disappeared, and then the tumor of one mouse has regressed, while the other 5 mice did not have tumor regression at the end of the experiment (PG-D45). In the high-dose (5 mg/kg) group, the tumor growth was significantly inhibited after administration. On the 10th day after the administration (PG-D10), the tumor of 1 mouse out of 6 began to disappear. On the 24th day after the administration (PG-D24), the tumors of all 6 mice had disappeared. At the end of the experiment (PG-D45), the tumors of the mice showed no regression.

The test drug AS11259-ADC-0012 treatment group produced a significant anti-tumor effect at the dose of 5 mg/kg compared with the vehicle control group, and the average tumor volume on the 14th day after administration (PG-D14) was 13 mm$^3$. The tumor growth inhibition (TGI) was 99.6%, which was statistically significantly different from the control group (p=0.001). Tumor growth was significantly inhibited in the mice of this treatment group after administration, and on the 10th day after administration (PG-D10), the tumor in 2 out of 6 mice began to disappear, on the 31st day after administration (PG-D31) the tumor in 5 out of 6 mice had disappeared. At the end of the experiment (PG-D45), the tumors of the 5 mice showed no regression.

The test drug AS11259-ADC-011 treatment group produced significant anti-tumor effects at the doses of 2 mg/kg and 5 mg/kg compared with the vehicle control group, and the anti-tumor effect showed a significant dose-response relationship. On the 14th day after administration (PG-D14), the mean tumor volumes were 818 mm$^3$ and 17 mm$^3$, respectively. The relative tumor inhibition rates were 73.8% and 99.4%, respectively, and there were statistically significant differences from the control group (both p value is 0.001). In the high-dose (5 mg/kg) group, the tumor growth was significantly inhibited after administration. On the 10th day after the administration (PG-D10), the tumor in 1 out of 6 mice began to disappear. On the 28th day after the administration (PG-D28), the tumors of all 6 mice had disappeared. At the end of the experiment (PG-D45), the tumors of the mice showed no regression.

The test drug AS11259-ADC-008 treatment group produced a significant anti-tumor effect compared with the vehicle control group at a dose of 2.5 mg/kg, and the average tumor volume was 1390 mm$^3$ on the 14th day after administration (PG-D14). The tumor growth inhibition (TGI) was 54.8%, which was statistically significantly different from the control group (p=0.009).

Granta-519 Model

Granta-519 cells were cultured in RPMI 1640 medium containing 10% fetal bovine serum at 37° C., 5% CO$_2$. Cells in logarithmic growth phase were counted and collected, resuspended in 1:1 PBS and Matrigel, and subcutaneously inoculated to right side of the mice NOD/SCID mice (female, 8-9 weeks, average body weight 20.5 g, purchased from Beijing Ankai Yibo Biotechnology Co., Ltd., animal certificate number: 11402400012442; feeding environment: SPF level). The volume of cells inoculated per mouse was 0.1 ml, and the amount of cells inoculated was 1×10$^7$ cells per mouse. When average tumor size reached to 200 mm$^3$, the body weights were weighed, and the mice were grouped randomly, followed by the initiation of administration. The administration was via tail vein, and the administration frequency was one time only.

Result Evaluation Standard

The mean tumor volume of the vehicle control group of the first batch of experiments reached 2744 mm$^3$ on the 17th day after administration (PG-D17). The euthanasia was performed on the control group and the TGI of the drug treatment groups was calculated on the 17th day. On the 45th day after the administration, the experiment was terminated, and all the rest mice were euthanized, while the number of mice in which tumors were regressed completely in each group was recorded.

Experimental Results

Figure 4:
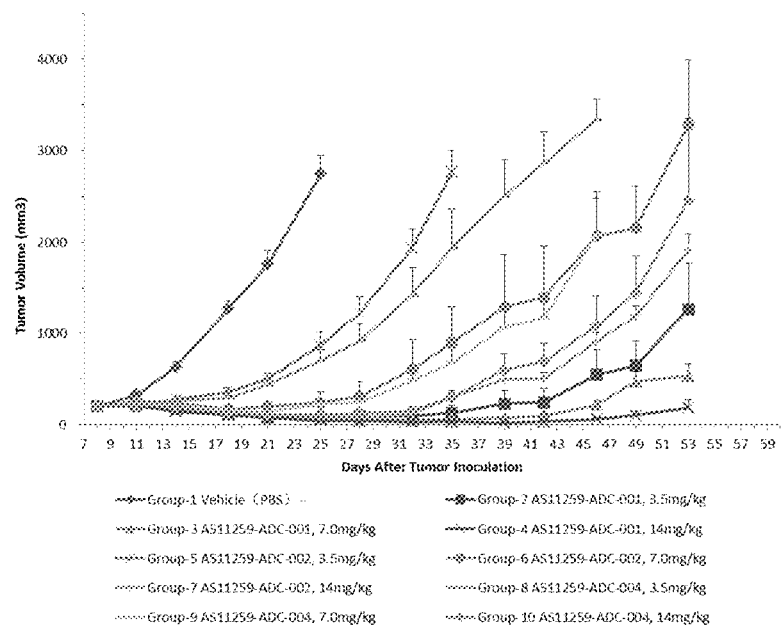
FIG. 4: Therapeutical effect of AS11259-ADC-001, 002, 004 on subcutaneous xenografts of human lymphoma Granta-519 in nude mice.
Figure 5:
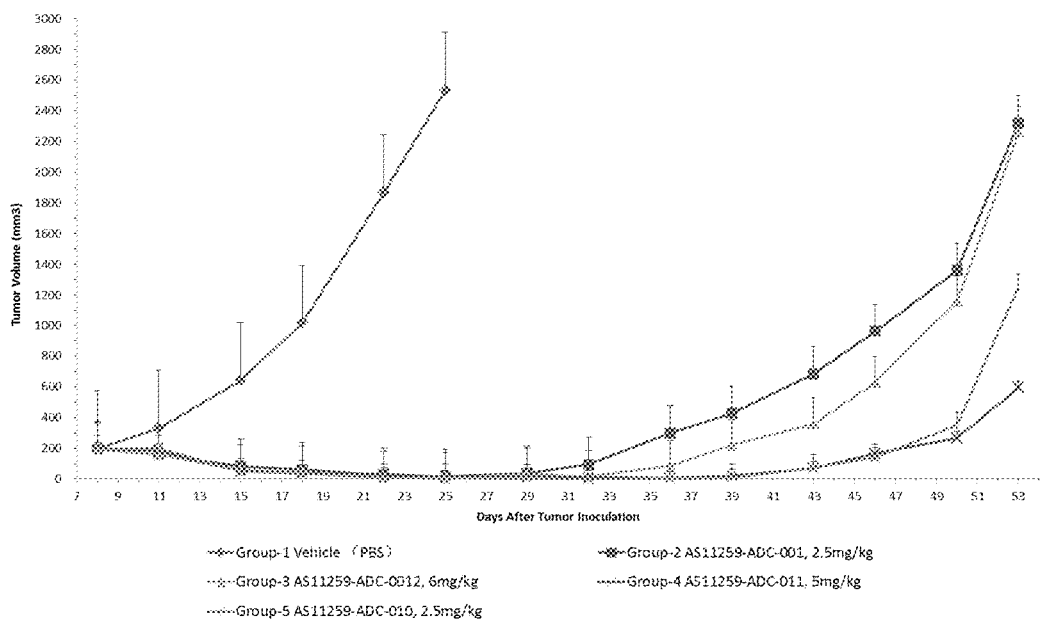
FIG. 5: Therapeutical effect of AS11259-ADC-001, 0012, 011, 010 on subcutaneous xenografts of human lymphoma Granta-519 in nude mice.

The results are shown in Tables 11 and 12 and FIGS. 4 and 5 below.

TABLE 11

Effect of AS11259-ADC-001, 002 and 004 on subcutaneous xenografts of nude mice with human lymphoma Granta-519

| Group | Animals | Test subject | Dosage (mg/kg) | PG-D17 (mm$^3$) | TGI (%) | P | Body weight(g) | PG-D46 Total resolved |
|---|---|---|---|---|---|---|---|---|
| 1 | 6 | Vehicle(PBS) | — | 2744 ± 208 | — | — | 23.8 ± 0.3 | 0 |
| 2 | 6 | AS11259-ADC-001 | 3.5 | 68 ± 22 | 97.5 | <0.001 | 22.3 ± 0.5 | 0 |
| 3 | 6 | AS11259-ADC-001 | 7.0 | 68 ± 11 | 97.6 | <0.001 | 21.9 ± 0.6 | 1 |
| 4 | 6 | AS11259-ADC-001 | 14 | 49 ± 9 | 98.2 | <0.001 | 21.6 ± 0.5 | 2 |
| 5 | 6 | AS11259-ADC-002 | 3.5 | 871 ± 148 | 68.5 | <0.001 | 22.7 ± 0.6 | 0 |
| 6 | 6 | AS11259-ADC-002 | 7.0 | 246 ± 114 | 90.8 | <0.001 | 22.8 ± 0.5 | 0 |
| 7 | 6 | AS11259-ADC-002 | 14 | 101 ± 9 | 96.3 | <0.001 | 22.0 ± 0.5 | 0 |
| 8 | 6 | AS11259-ADC-004 | 3.5 | 703 ± 116 | 74.3 | <0.001 | 22.4 ± 0.3 | 0 |
| 9 | 6 | AS11259-ADC-004 | 7.0 | 222 ± 46 | 92.1 | <0.001 | 22.0 ± 0.4 | 0 |
| 10 | 6 | AS11259-ADC-004 | 14 | 117 ± 14 | 95.7 | <0.001 | 20.5 ± 1.0 | 1 |

TABLE 12

Effect of AS11259-ADC-001, 0012, 0011 and 010 on subcutaneous xenografts of nude mice with human lymphoma Granta-519

| Group | Animals | Test subject | Dosage (mg/kg) | PG-D17 (mm$^3$) | TGI (%) | P | Body weight(g) | PG-D45 Total resolved |
|---|---|---|---|---|---|---|---|---|
| 1 | 6 | Vehicle(PBS) | — | 2535 ± 481 | — | — | 24.8 ± 0.6 | 0 |
| 2 | 6 | AS11259-ADC-001 | 2.5 | 17 ± 8 | 99.3 | 0.001 | 22.6 ± 0.2 | 0 |
| 3 | 6 | AS11259-ADC-0012 | 6 | 6 ± 4 | 99.8 | 0.001 | 22.0 ± 0.6 | 0 |
| 4 | 6 | AS11259-ADC-011 | 5 | 11 ± 8 | 99.6 | 0.001 | 22.3 ± 0.3 | 0 |
| 5 | 6 | AS11259-ADC-010 | 2.5 | 9 ± 6 | 99.6 | 0.001 | 22.2 ± 0.3 | 0 |

In the first batch of vehicle control groups, the average tumor volume reached 2744 mm³ on day 17 after administration (PG-D17).

The test drug AS11259-ADC-001 treatment group produced significant anti-tumor effects at three concentrations (3.5 mg/kg, 7 mg/kg, 14 mg/kg) compared with the vehicle control group. In the three administration groups, the average tumor volume on the 17th day after administration (PG-D17) was 68 mm³, 68 mm³, and 49 mm³, respectively, and the tumor growth inhibition (TGI) were 97.5%, 97.6%, and 98.2%, respectively, statistically extremely significantly different from the control group (p values are less than 0.001). On the 45th day after administration (PG-D45), the average tumor volume of the three administration groups reached 1268 mm³, 536 mm³ and 184 mm³, respectively, indicating that the test substance showed significant dose-response relationship in anti-tumor effect.

The test drug AS11259-ADC-002 treatment group produced significant anti-tumor effects at three concentrations (3.5 mg/kg, 7 mg/kg, 14 mg/kg) compared with the vehicle control group, and presented significant dose-response relationship. In the low dosing (3.5 mg/kg) group, the average tumor volume was 871 mm³ on the 17th day after administration (PG-D17), and the tumor growth inhibition (TGI) was 68.5%, with statistically extremely significant difference compared to the vehicle control group (p<0.001). In the medium dosing (7 mg/kg) group, the average tumor volume was 246 mm³ on the 17th day after administration (PG-D17), and the tumor growth inhibition (TGI) was 90.8%, with statistically significant difference compared to the vehicle control group (p<0.001). In the high dosing (14 mg/kg) group, the average tumor volume was 101 mm³ on the 17th day after administration (PG-D17), and the tumor growth inhibition (TGI) was 96.3% with statistically significant difference compared to the vehicle control group (p<0.001).

The test drug AS11259-ADC-004 treatment group produced significant anti-tumor effects at three dosing (3.5 mg/kg, 7 mg/kg, 14 mg/kg) compared with the vehicle control group, and showed significant dose-response relationship. In the low-dosing (3.5 mg/kg) group, the average tumor volume was 703 mm³ on the 17th day after administration (PG-D17), and the tumor growth inhibition (TGI) was 74.3%, with statistically extremely significant difference compared to the vehicle control group (p<0.001). In the medium dosing (7 mg/kg) group, the average tumor volume was 222 mm³ on the 17th day after administration (PG-D17), and the tumor growth inhibition (TGI) was 92.1% with statistically significant difference compared to the vehicle control group (p<0.001). In the high dosing (14 mg/kg) group, the average tumor volume was 117 mm³ on the 17th day after administration (PG-D17), and the tumor growth inhibition (TGI) was 95.7%, with statistically significant difference compared to the vehicle control group (p<0.001).

In the second batch of the experiment, the average tumor volume of the vehicle control group reached 2535 mm³ on the 17th day after administration (PG-D17).

Test drug AS11259-ADC-001 (2.5 mg/kg), AS11259-ADC-0012 (6 mg/kg), AS11259-ADC-011 (5 mg/kg) and AS11259-ADC-010 (2.5 mg/kg) treatment groups significantly inhibited tumor growth after administration. On the 17th day after administration (PG-D17), the average tumor volume was 17 mm³, 6 mm³, 11 mm³ and 9 mm³, respectively. The tumor growth inhibition (TGI) was 99.3%, 99.8%, 99.6%, and 99.6%, with statistically significant difference compared to the vehicle control group (all p values are 0.001).

WSU-DLCL2 Model

WSU-DLCL2 cells were cultured in RPMI 1640 medium containing 10% fetal calf serum at 37° C., 5% $CO_2$. Cells in logarithmic growth phase were collected and were inoculated subcutaneously by injection into the right flanks of NOD/SCID mice (female, 8-9 weeks of age from Beijing Ankai Yibo Biotechnology Co., Ltd., animal certificate number: 11402400012441; feeding environment: SPF level), The volume of cells inoculated per mouse was 0.1 ml, and the amount of cells inoculated was $1\times10^7$. When average tumor size reached to 200 mm³, weigh the body weight, and the mice were grouped randomly, and the administration was initiated. The administration was via tail vein, and the administration frequency was one time only.

Result Evaluation Standard

In the vehicle control group of the first batch, the average tumor volume reached 2146 mm³ on the 32th day after administration (PG-D32). The euthanasia was performed on the control group and the TGI of the drug treatment groups was calculated on the 32th day. On the 43th day after the administration, the experiment was terminated, and all the rest mice were euthanized, while the number of mice in which tumors were regressed completely in each group was recorded.

For the vehicle control group of the second batch, the average tumor volume reached 2360 mm³ on the 35th day after administration (PG-D35). The euthanasia was performed on the control group and the TGI of the drug treatment groups was calculated on the 35th day. On the 42th day after the administration, the experiment was terminated, and all the rest mice were euthanized, while the number of mice in which tumors were regressed completely in each group was recorded.

Experimental Result

Figure 6:
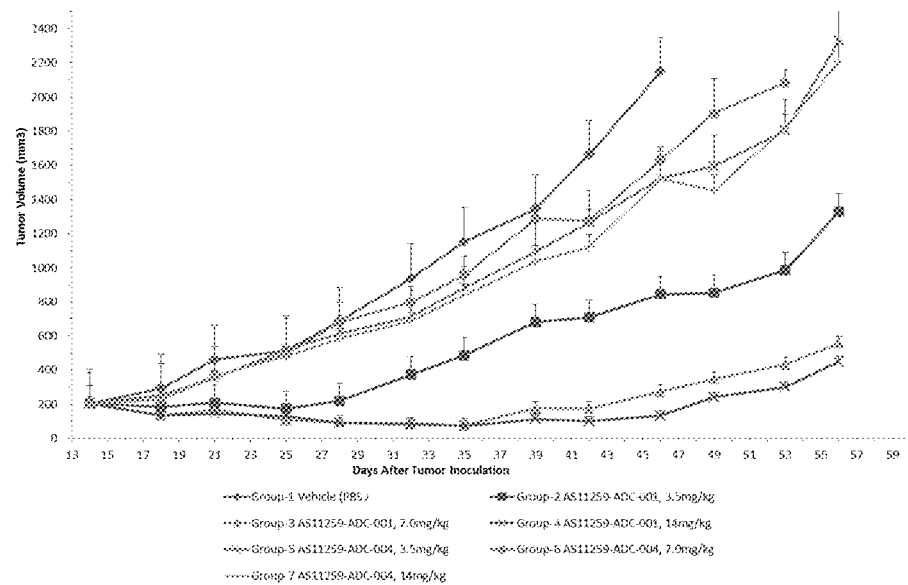
FIG. 6: Therapeutical effect of AS11259-ADC-001, 004 on subcutaneous xenografts of human lymphoma WSU-DLCL2 in nude mice.
Figure 7:
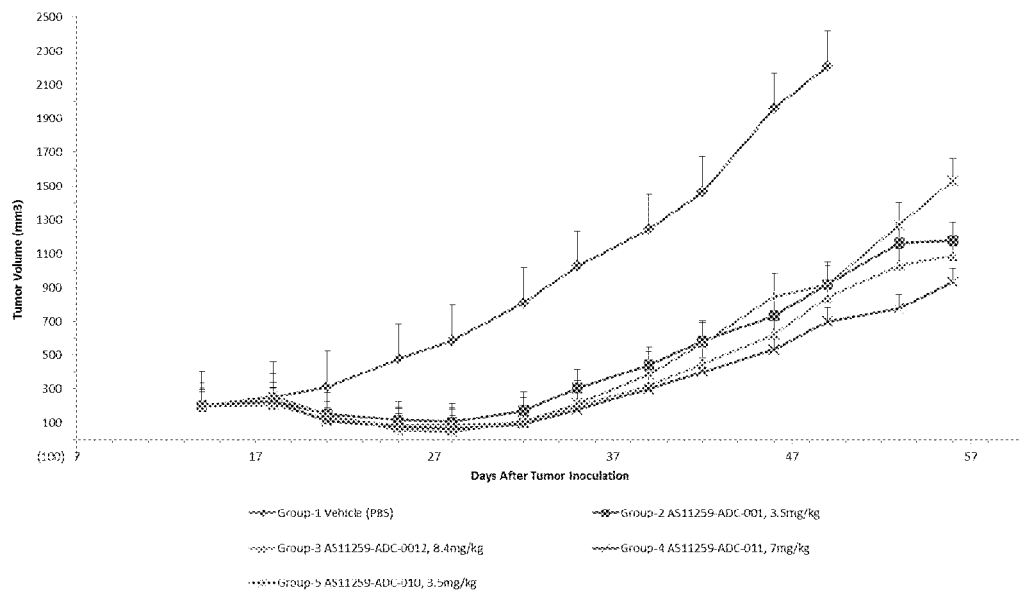
FIG. 7: Therapeutic effect of AS11259-ADC-001, 0012, 011, 010 on subcutaneous xenografts of human lymphoma WSU-DLCL2 in nude mice.

The experimental results are shown in Tables 13, 14 and FIGS. 6 and 7 below.

TABLE 13

Therapeutical effect of AS11259-ADC-001, 004 on subcutaneous xenografts of nude mice with human lymphoma WSU-DLCl2

| Group | Animals | Test subject | Dosage (mg/kg) | PG-D32 (mm³) | TGI (%) | P | Body weight(g) | PG-D43 Total resolved |
|---|---|---|---|---|---|---|---|---|
| 1 | 6 | Vehicle(PBS) | — | 2146 ± 293 | — | — | 23.2 ± 0.7 | 0 |
| 2 | 6 | AS11259-ADC-001 | 3.5 | 845 ± 86 | 60.4 | 0.004 | 22.9 ± 0.3 | 0 |
| 3 | 6 | AS11259-ADC-001 | 7.0 | 273 ± 74 | 87.6 | 0.001 | 22.2 ± 0.4 | 1 |
| 4 | 6 | AS11259-ADC-001 | 14 | 132 ± 18 | 93.7 | 0.001 | 21.8 ± 0.1 | 0 |
| 5 | 6 | AS11259-ADC-004 | 3.5 | 1526 ± 73 | 28.3 | 0.080 | 22.3 ± 0.4 | 0 |
| 6 | 6 | AS11259-ADC-004 | 7.0 | 1632 ± 51 | 24.0 | 0.123 | 22.4 ± 0.5 | 0 |
| 7 | 6 | AS11259-ADC-004 | 14 | 1521 ± 91 | 28.6 | 0.080 | 22.8 ± 0.4 | 0 |

TABLE 14

Therapeutical effect of AS11259-ADC-001, 0012, 011, and 010 on subcutaneous xenografts of nude mice with human lymphoma WSU-DLCl2

| Group | Animals | Test subject | Dosage (mg/kg) | PG-D35 (mm$^3$) | TGI (%) | P | Body weight(g) | PG-D42 Total resolved |
|---|---|---|---|---|---|---|---|---|
| 1 | 6 | Vehicle(PBS) | — | 2360 ± 164 | — | — | 23.7 ± 0.6 | 0 |
| 2 | 6 | AS11259-ADC-001 | 3.5 | 919 ± 127 | 61.0 | <0.001 | 22.1 ± 0.5 | 0 |
| 3 | 6 | AS11259-ADC-0012 | 8.4 | 840 ± 125 | 64.4 | <0.001 | 22.7 ± 0.3 | 0 |
| 4 | 6 | AS11259-ADC-011 | 7.0 | 700 ± 61 | 71.4 | <0.001 | 21.1 ± 0.3 | 0 |
| 5 | 6 | AS11259-ADC-010 | 3.5 | 913 ± 248 | 62.0 | 0.001 | 22.1 ± 0.3 | 0 |

In the first batch xenograft model, the test drug AS11259-ADC-001 treatment group produced significant anti-tumor effects at three dosing (3.5 mg/kg, 7 mg/kg, 14 mg/kg) compared with the vehicle control group, and presented significant dose-response relationship. In the low dosing (3.5 mg/kg) group, the average tumor volume was 845 mm$^3$ on the 32nd day after administration (PG-D32), and the tumor growth inhibition (TGI) was 60.4%, with statistically significant difference compared to the vehicle control group (p=0.004). In the medium dosing (7 mg/kg) group, the average tumor volume was 273 mm$^3$ on the 32nd day after administration (PG-D32), and the tumor growth inhibition (TGI) was 87.6%, with statistically significant difference compared to the vehicle control group (p=0.001). In the high dosing (14 mg/kg) group, the average tumor volume was 132 mm$^3$ on the 32nd day after administration (PG-D32), and the tumor growth inhibition (TGI) was 93.7%, with statistically extremely significant difference compared to the vehicle control group (p=0.001).

The test drug AS11259-ADC-004 treatment group produced a slight anti-tumor effect at three dosing groups (3.5 mg/kg, 7 mg/kg, 14 mg/kg) compared with the vehicle control group, but without significant statistical differences.

In the three dosing groups, the average tumor volume on the 32nd day after administration (PG-D32) was 1526 mm$^3$, 1632 mm$^3$, and 1521 mm$^3$, respectively, and the tumor growth inhibition (TGI) were 28.3%, 24.0%, and 28.6, respectively. The p values were 0.080, 0.123, and 0.080, respectively.

In the second batch xenograft model, the test drug AS11259-ADC-001 (3.5 mg/kg), AS11259-ADC-0012 (8.4 mg/kg), AS11259-ADC-011 (7 mg/kg) and AS11259-ADC-010 (3.5 mg/kg) treatment group all significantly inhibited tumor growth after administration. On the 35th day after administration (PG-D35), the average tumor volumes were 912 mm$^3$, 840 mm$^3$, 700 mm$^3$ and 913 mm$^3$, respectively. The tumor growth inhibition (TGI) were 61.0%, 64.4%, 71.4%, and 62.0%, with p values <0.001, <0.001, <0.001, and 0.001 respectively. The test drug was well tolerated by the mice of all dosing groups.

All documents mentioned in the present application are hereby incorporated by reference in their entirety, as if any single document is referenced in its entirety. In addition, it should be understood that various modifications and changes may be made by those skilled in the art, which shall all fall within the scope of the appended claims.

The invention claimed is:

1. An anti-CD79b antibody or antigen-binding fragment thereof, wherein the anti-CD79b antibody or antigen-binding fragment thereof comprises: HCDR1 comprising the amino acid sequence set forth in SEQ ID NO: 1; HCDR2 comprising the amino acid sequence set forth in SEQ ID NO: 2; HCDR3 comprising the amino acid sequence set forth in SEQ ID NO:3; LCDR1 comprising the amino acid sequence set forth in SEQ ID NO:4; LCDR2, comprising the amino acid sequence set forth in SEQ ID NO: 5; and LCDR3, comprising the amino acid sequence set forth in SEQ ID NO: 6.

2. The anti-CD79b antibody or antigen-binding fragment thereof according to claim 1, wherein the amino acid sequence of the HCDR1 of the anti-CD79b antibody or antigen-binding fragment thereof consists of SEQ ID NO: 1, the amino acid sequence of HCDR2 consists of SEQ ID NO: 2, the amino acid sequence of HCDR3 consists of SEQ ID NO: 3, the amino acid sequence of LCDR1 consists of SEQ ID NO: 4, the amino acid sequence of LCDR2 consists of SEQ ID NO: 5, and the amino acid sequence of LCDR3 consists of SEQ ID NO: 6.

3. The anti-CD79b antibody or antigen-binding fragment thereof according to claim 1, wherein the anti-CD79b antibody is a monoclonal antibody, and/or the anti-CD79b antibody is a humanized antibody or a chimeric antibody.

4. The anti-CD79b antibody or antigen-binding fragment thereof according to claim 1, wherein the amino acid sequence of the heavy chain variable region of the anti-CD79b antibody is set forth in SEQ ID NO: 7 or 11, and/or the amino acid sequence of the light chain variable region of the anti-CD79b antibody is set forth in SEQ ID NO: 8 or 12; or the amino acid sequence of the heavy chain variable region of the anti-CD79b antibody is selected from the amino acid sequence set forth in any one of SEQ ID NOs: 13-17, and/or the amino acid sequence of the light chain variable region of the anti-CD79b antibody is selected from the amino acid sequence set forth in any one of SEQ ID NOs: 18-22.

5. The anti-CD79b antibody or antigen-binding fragment thereof according to claim 1, wherein the amino acid sequence of the heavy chain of the anti-CD79b antibody is selected from amino acid sequences that have at least 90% sequence identity to any one of the group consisting of the amino acid sequences set forth in SEQ ID NOs: 25, 27, 29, 31 and 33; and the amino acid sequence of the light chain of the anti-CD79b antibody is selected from amino acid sequences that have at least 90% sequence identity to any one of the group consisting of the amino acid sequences set forth in SEQ ID NOs: 26, 28, 30, 32 and 34.

6. The anti-CD79b antibody or antigen-binding fragment thereof according to claim 1, wherein the anti-CD79b antibody is selected from the group consisting of:

(1) an antibody of which the amino acid sequence of the heavy chain is set forth in SEQ ID NO: 25, and the amino acid sequence of the light chain is set forth in SEQ ID NO: 26;

(2) an antibody of which the amino acid sequence of the heavy chain is set forth in SEQ ID NO: 27, and the amino acid sequence of the light chain is set forth in SEQ ID NO: 28;

(3) an antibody of which the amino acid sequence of the heavy chain is set forth in SEQ ID NO: 29, and the amino acid sequence of the light chain is set forth in SEQ ID NO: 30;

(4) an antibody of which the amino acid sequence of the heavy chain is set forth in SEQ ID NO: 31, and the amino acid sequence of the light chain is set forth in SEQ ID NO: 32;

(5) an antibody of which the amino acid sequence of the heavy chain is set forth in SEQ ID NO: 33, and the amino acid sequence of the light chain is set forth in SEQ ID NO: 34.

7. An antibody-drug conjugate, characterized in that the conjugate is a conjugate of the antibody or antigen-binding fragment thereof according to claim 1 with a cytotoxic agent.

8. The antibody-drug conjugate according to claim 7, wherein the structure of the conjugate is as follows:

$A\text{-}(V\text{-}L\text{-}D)_n$ wherein:
A is an antibody;
V-L is a linker, V may or may not be present and is a bismaleimide or tetramaleimide type linker member;
L may or may not be present, and can be a cleavable linker or a non-cleavable linker;
at least one of V and L is present;
D is a cytotoxic agent of interest; and
n is an integer from 1 to 4.

9. The antibody-drug conjugate according to claim 7, wherein the cytotoxic agent is a chemotherapeutic drug, a growth inhibitor, a toxin or a radioisotope.

10. A pharmaceutical composition comprising the antibody of claim 1 or an antibody-drug conjugate thereof comprising the antibody or antibody fragment thereof of claim 1 conjugated with a drug, and a pharmaceutically acceptable carrier.

11. The pharmaceutical composition according to claim 10, wherein the pharmaceutical composition comprises the antibody-drug conjugate.

12. A polynucleotide selected from the group consisting of:
(1) a polynucleotide encoding the amino acid sequence of any one set forth in SEQ ID NOs: 7-8, 11-22, and 25-34;
(2) a polynucleotide encoding the antibody or antigen-binding fragment thereof according to claim 1; and
(3) complement of the polynucleotide of (1) or (2).

13. The polynucleotide according to claim 12, wherein the polynucleotide is selected from the group consisting of:
(a) the polynucleotide set forth in any one of SEQ ID NOs: 36-39; and
(b) the complement of the polynucleotide of (a).

14. A vector comprising a polynucleotide encoding the antibody or an antigen-binding fragment thereof according to claim 1, or the complement thereof, wherein the vector is a cloning vector or an expression vector.

15. A method for treating a CD79b-mediated disease comprising administering to a subject in need thereof a therapeutically effective amount of the anti-CD79b antibody or antigen-binding fragment thereof according to claim 1, or a conjugate of the antibody or an antigen-binding fragment thereof of claim 1 with a drug.

16. The method according to claim 15, wherein the disease is a cancer of the hematopoietic system.

17. The method according to claim 15, wherein the disease is a B cell proliferative disorder.

18. The method according to claim 15, wherein the disease is lymphoma or leukemia.

19. The method according to claim 15, wherein the disease is selected from non-Hodgkin's lymphoma (NHL), aggressive NHL, recurrent aggressive NHL, recurrent painless NHL, refractory NHL, refractory painless NHL, small lymphocytic lymphoma, mantle cells lymphoma, chronic lymphocytic leukemia (CLL), hairy cell leukemia (HCL) or acute lymphocytic leukemia (ALL).

20. A method of detecting a presence of a cell proliferative disorder associated with increased expression of CD79b, comprising:
contacting test cells in a biological sample and control cells with the anti-CD79b antibody or antigen-binding fragment thereof according to claim 1;
determining a level of the antibody bound to the test cells in the biological sample and a level of the antibody bound to the control cells by testing the binding of the said antibody to CD79b; and
comparing the level of the antibody bound to the test cells in the sample with the level of the antibody bound to the control cells;
wherein the level of bound antibody is normalized by relating the number of cells expressing CD79b in test and control samples, and wherein a higher level of antibody bound in the test sample than the control sample indicates a presence of a cell proliferative disorder associated with increased expression of CD79b.

21. An article comprising a first container, wherein the first container comprises a composition, comprising the anti-CD79b antibody or antigen-binding fragment thereof according to claim 1, or the conjugate of the anti-CD79b antibody or antigen-binding fragment thereof with a drug, or a pharmaceutical composition of the anti-CD79b antibody or antigen-binding fragment thereof or the conjugate.

22. The article according to claim 21, wherein the article further includes a second container comprising a pharmaceutically acceptable buffer; or the composition comprises an anti-CD79b antibody or antigen-binding fragment thereof, wherein the anti-CD79b antibody or antigen-binding fragment thereof comprises: HCDR1 comprising the amino acid sequence set forth in SEQ ID NO: 1; HCDR2 comprising the amino acid sequence set forth in SEQ ID NO: 2; HCDR3 comprising the amino acid sequence set forth in SEQ ID NO:3; LCDR1 comprising the amino acid sequence set forth in SEQ ID NO:4; LCDR2, comprising the amino acid sequence set forth in SEQ ID NO: 5; and LCDR3, comprising the amino acid sequence set forth in SEQ ID NO: 6,
wherein the article further comprises a container containing a diluent, buffer or control antibody for detection.

* * * * *